United States Patent
Beswick et al.

(10) Patent No.: US 8,759,348 B2
(45) Date of Patent: Jun. 24, 2014

(54) USE OF 4-(PYRROLIDIN-1-YL)QUINOLINE COMPOUNDS TO KILL CLINICALLY LATENT MICROORGANISMS

(75) Inventors: Mandy Christine Beswick, Barcelona (GB); Susan Mary Cramp, Harlow (GB); Yanmin Hu, London (GB); Thomas David Pallin, London (GB); Hazel Joan Dyke, Harlow (GB); Anthony Coates, London (GB)

(73) Assignee: Helperby Therapeutics Limited, Selby (GB)

( * ) Notice: Subject to any disclaimer, the term of this patent is extended or adjusted under 35 U.S.C. 154(b) by 559 days.

(21) Appl. No.: 12/600,470

(22) PCT Filed: May 16, 2008

(86) PCT No.: PCT/GB2008/001694
§ 371 (c)(1),
(2), (4) Date: Aug. 20, 2010

(87) PCT Pub. No.: WO2008/142384
PCT Pub. Date: Nov. 27, 2008

(65) Prior Publication Data
US 2010/0305065 A1    Dec. 2, 2010

(30) Foreign Application Priority Data

May 17, 2007  (GB) .................................. 0709489.9
Apr. 25, 2008  (GB) .................................. 0807591.3

(51) Int. Cl.
| | | |
|---|---|---|
| A61K 31/4709 | (2006.01) | |
| A61K 31/497 | (2006.01) | |
| A61K 31/501 | (2006.01) | |
| C07D 401/14 | (2006.01) | |
| C07D 403/14 | (2006.01) | |
| C07D 401/04 | (2006.01) | |

(52) U.S. Cl.
CPC ........... *A61K 31/4709* (2013.01); *A61K 31/497* (2013.01); *A61K 31/501* (2013.01); *C07D 401/04* (2013.01); *C07D 403/14* (2013.01)
USPC ................. 514/252.04; 514/255.05; 544/238; 544/405; 546/171; 546/178

(58) Field of Classification Search
None
See application file for complete search history.

(56) References Cited

U.S. PATENT DOCUMENTS

| | | | |
|---|---|---|---|
| 6,818,767 B2 * | 11/2004 | Mueller et al. ................. | 544/128 |
| 7,074,801 B1 | 7/2006 | Yoshida et al. | |
| 2002/0198194 A1 * | 12/2002 | Mueller et al. ........... | 514/217.07 |
| 2004/0248890 A1 | 12/2004 | Gonzalez | |

FOREIGN PATENT DOCUMENTS

| | | | | |
|---|---|---|---|---|
| WO | WO 2002/094789 A1 | 11/2002 | | |
| WO | WO 03/028726 | * 4/2003 | ......... | A61K 31/4709 |
| WO | WO 2004/002960 A1 | 1/2004 | | |
| WO | WO 2006/070284 A1 | 7/2006 | | |
| WO | WO 2006/071875 A1 | 7/2006 | | |

OTHER PUBLICATIONS

"Guidance for Industry: Q3C—Tables and List." US DHHS, FDA, CDER, CBER, Nov. 2003, Revision 1.*
Wolf et al. J. Org. Chem. 2003, 68, pp. 7077-7084.*
Huff J. Med. Chem. 34(8) 1991, p. 2305-2314.*
Howson, "Alpha 1 Anti-Trypsin Deficiency," NYU 2012.*
"Cystic Fibrosis: Prevention." emedicinehealth, Accessed Jul. 17, 2012. <http://www.emedicinehealth.com/cystic_fibrosis-health/page8_em.htm>.*
Snyder et al., J. Med. Liban 48(4): 208-214, 2000 (PubMed Abstract provided.*
The Merck Manual (16th Ed., 1999, pp. 52-55).*
Miles, Medline Abstract (Community Pract, vol. 78, Issue 8, pp. 292-294) Aug. 2005.*
Li, Guang-yun et al., "Studies on antimalarials. VII. Synthesis and antimalarial activites of some derivatives of 2, 4-dipiperidino- or 2, 4-dipyrrolidino-6-(substituted) aminoquinazolines," *Yaoxue Xuebao* [*Acta Pharmaceutical Sinica*], vol. 17, No. 11 (1982), pp. 827-834. XP-002491844.

* cited by examiner

*Primary Examiner* — Alicia L Otton
(74) *Attorney, Agent, or Firm* — Steptoe & Johnson LLP

(57) ABSTRACT

There is provided the use of compounds of formula wherein $R^1$, $R^2$, $R^3$ and E have meanings given in the description, for the preparation of a medicament for killing clinically latent microorganisms. There is also provided the use of compounds of formula I for treating microbial infections, as well as certain compounds of formula (I) per se.

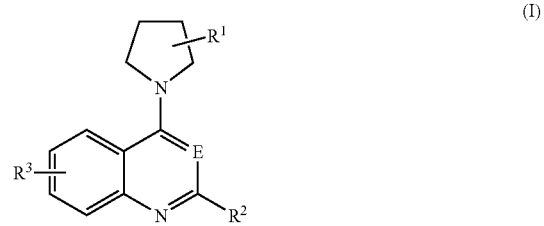

(I)

18 Claims, 3 Drawing Sheets

USE OF 4-(PYRROLIDIN-1-YL)QUINOLINE COMPOUNDS TO KILL CLINICALLY LATENT MICROORGANISMS

CLAIM OF PRIORITY

This application claims priority to PCT application No. PCT/GB2008/001694, filed May 16, 2008, which claims priority to British Application No. 0709489.9, filed May 17, 2007 and British Application No. 0807591.3, filed Apr. 25, 2008, each of which is incorporated by reference in its entirety.

This invention relates to the use of compounds based upon the 4-(pyrrolidin-1-yl)quinoline ring system to kill clinically latent microorganisms. The invention further relates to the use of such compounds to treat microbial infections, as well as, inter alia, certain of the compounds per se.

The listing or discussion of a prior-published document in this specification should not necessarily be taken as an acknowledgement that the document is part of the state of the art or is common general knowledge.

Before the introduction of antibiotics, patients suffering from acute bacterial infections (e.g. tuberculosis or pneumonia) had a low chance of survival. For example, mortality from tuberculosis was around 50%.

Although the introduction of antibacterial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (see *Nature Reviews, Drug Discovery* 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (see *Lancet* 357, 1179 (2001) and *Lancet* 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics.

Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, for example, with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps.

Nevertheless, the rate that resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (see Science 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many bacterial infections include sub-populations of bacteria that are phenotypically resistant to antimicrobials (see, for example: *J. Antimicrob. Chemother.* 4, 395-404 (1988); *J. Med. Microbiol.* 38, 197-202 (1993); *J. Bacteriol.* 182, 1794-1801 (2000); ibid. 182, 6358-6365 (2000); ibid. 183, 6746-6751 (2001); *FEMS Microbiol. Lett.* 202, 59-65 (2001); and *Trends in Microbiology* 13, 34-40 (2005)). There appear to be several types of such phenotypically resistant bacteria, including persisters, stationary-phase bacteria, as well as those in the depths of biofilms. However, each of these types is characterised by its low rate of growth (compared to log-phase bacteria under the same conditions). Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (see, for example: *Proc. Natl. Acad. Sci. USA* 92, 11736-11740 (1995); *J. Bacteriol.* 179, 6688-6691 (1997); and *Antimicrob. Agents Chemother.* 44, 1771-1777 (2000)). For example, non-dividing *E. coli* continually mutates to ciprofloxacin resistance during a seven-day exposure to the agent. Thus, "latent" bacteria might be one of the sources of genotypically resistant bacteria.

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

Certain compounds containing the 4-(pyrrolidin-1-yl) quinoline skeleton are disclosed in: WO 92/17452; WO 98/05644; WO 02/094789; and WO 2006/070284. None of these documents disclose that compounds based upon the 4-(pyrrolidin-1-yl)quinoline ring system to kill clinically latent microorganisms.

Further compounds containing the 4-(pyrrolidin-1-yl) quinoline skeleton are disclosed in: US 2006/217,377 and WO 2006/071875. These documents disclose compounds based upon the 4-(pyrrolidin-1-yl)quinoline ring system for use only as inhibitors of voltage gated (potassium or sodium) ion channels or as antagonists of chemokine receptors.

Activity against malaria parasites for certain 6-substituted (2,4-dipyrrolidin-1-yl)quinazoline compounds is mentioned in *Yao Xue Xue Bao* 827-834 (1982).

We have now found, surprisingly, that certain 4-(pyrrolidin-1-yl)quinolines may be used to kill clinically latent microorganisms.

According to a first aspect of the invention, there is provided the use of a compound of formula I, or a pharmaceutically-acceptable derivative thereof, for the preparation of a medicament for killing clinically latent microorganisms, wherein the compound of formula I is represented by the structure

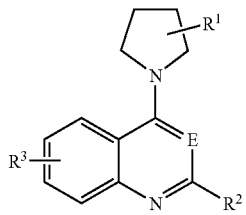

I wherein
E represents CH or N;
$R^1$ represents one to four substituents on the pyrrolidinyl ring, each substituent independently representing the group —X—$R^{4a}$;
X represents
(a) a direct bond,
(b) —O— or
(c) —N($R^{4b}$)—;
$R^{4a}$ and $R^{4b}$ independently represent
(a) H,
(b) $C_{1-12}$ alkyl, $C_{3-12}$ cycloalkyl, $C_{3-12}$ cycloalkenyl (which latter three groups are optionally substituted by one or more substituents selected from halo, nitro, CN, $C_{1-6}$ alkyl, $C_{2-6}$ alkenyl, $C_{2-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{5a}$, $S(O)_nR^{5b}$, $S(O)_2N(R^{5c})(R^{5d})$, $N(R^{5e})S(O)_2R^{5f}$, $N(R^{5g})(R^{5h})$, $B^1$—C(O)—$B^2$—$R^{5i}$, aryl and $Het^1$, and which $C_{3-12}$ cycloalkyl or $C_{4-12}$ cycloalkenyl groups may additionally be substituted by =O),
(c) aryl or
(d) $Het^2$;
$R^2$ represents
(a) H,
(b) $C_{1-12}$ alkyl, $C_{2-12}$ alkenyl, $C_{2-12}$ alkynyl, $C_{3-12}$ cycloalkyl, $C_{4-12}$ cycloalkenyl, which latter five groups are optionally substituted by one or more substituents selected from halo, nitro, CN, $C_{1-6}$ alkyl, $C_{2-6}$ alkenyl, $C_{2-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{6a}$, $S(O)_pR^{6b}$, $S(O)_2N(R^{6c})(R^{6d})$, $N(R^{6e})S(O)_2R^{6f}$, $N(R^{6g})(R^{6h})$, $B^3$—C(O)—$B^4$—$R^{6i}$, aryl and $Het^3$, and which $C_{3-12}$ cycloalkyl or $C_{4-12}$ cycloalkenyl groups may additionally be substituted by =O,
(c) aryl or
(d) $Het^4$;
$R^3$ represents H or one to four substituents on the fused benzene ring selected from
(a) halo,
(b) CN,
(c) $C_{1-12}$ alkyl, $C_{2-12}$ alkenyl, $C_{2-12}$ alkynyl, $C_{3-12}$ cycloalkyl, $C_{4-12}$ cycloalkenyl, which latter five groups are optionally substituted by one or more substituents selected from halo, nitro, CN, $C_{1-6}$ alkyl, $C_{2-6}$ alkenyl, $C_{2-6}$ alkynyl, $C_{3-8}$ cycloalkyl (which latter three groups are optionally substituted by one or more substituents selected from OH, =O, halo, $C_{1-4}$ alkyl and $C_{1-4}$alkoxy), $OR^{7a}$, $S(O)_qR^{7b}$, $S(O)_2N(R^{7c})(O)$, $N(R^{7e})S(O)_2R^{7f}$, $N(R^{7g})(R^{7h})$, $B^5$—C(O)—$B^6$—$R^{7i}$, aryl and $Het^5$, and which $C_{3-12}$ cycloalkyl or $C_{4-12}$ cycloalkenyl groups may additionally be substituted by =O,
(d) $OR^{8a}$,
(e) $S(O)_rR^{8b}$,
(f) $S(O)_2N(R^{8c})(R^{8d})$,
(g) $N(R_{8e})S(O)_2R^{8f}$,
(h) $N(R^{8g})(R^{8h})$,
(i) $B^7$—C(O)—$B^8$—$R^{8i}$,
(j) aryl or
(k) Hee;
$R^{5a}$ to $R^{5i}$, $R^{6a}$ to $R^{6i}$, $R^{7a}$ to $R^{7i}$ and $R^{8a}$ to $R^{8i}$ independently represent, at each occurrence,
(a) H,
(b) $C_{1-10}$ alkyl, $C_{2-10}$ alkenyl, $C_{2-10}$ alkynyl (which latter three groups are optionally substituted by one or more substituents selected from halo, OH, $C_{1-6}$ alkoxy, aryl and $Het^7$),
(c) $C_{3-10}$ cycloalkyl, $C_{4-10}$ cycloalkenyl (which latter two groups are optionally substituted by one or more substituents selected from halo, OH, =O, $C_{1-6}$ alkyl, $C_{1-6}$ alkoxy, aryl and $Het^8$),
(d) aryl or
(e) $Het^9$,
provided that $R^{5b}$, $R^{6b}$, $R^{7b}$ or $R^{8b}$ does not represent H when n, p, q or r, respectively is 1 or 2;
each aryl independently represents a $C_{6-10}$ carbocyclic aromatic group, which group may comprise either one or two rings and may be substituted by one or more substituents selected from
(a) halo,
(b) CN,
(c) $C_{1-12}$ alkyl, $C_{2-12}$ alkenyl, $C_{2-12}$ alkynyl, $C_{3-12}$ cycloalkyl, $C_{4-12}$ cycloalkenyl, which latter five groups are optionally substituted by one or more substituents selected from halo, nitro, CN, $C_{1-6}$ alkyl, $C_{2-6}$ alkenyl, $C_{2-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{9a}$, $S(O)_tR^{9b}$, $S(O)_2N(R^{9c})(R^{9d})$, $N(R^{9e})S(O)_2R^{9f}$, $N(R^{9g})(R^{9h})$, $B^9$—C(O)—$B^{10}$—$R^{9i}$, phenyl, naphthyl (which latter two groups are optionally substituted by one or more substituents selected from OH, halo, $C_{1-4}$ alkyl and $C_{1-4}$ alkoxy) and $Het^{10}$, and which $C_{3-12}$ cycloalkyl or $C_{4-12}$ cycloalkenyl groups may additionally be substituted by =O, (d) $OR^{10a}$,
(e) $S(O)_uR^{10b}$,
(f) $S(O)_2N(R^{10c})(R^{10d})$,
(g) $N(R^{10e})S(O)_2R^{10f}$,
(h) $N(R^{10g})(R^{10h})$,
(i) $B^{11}$—C(O)—$B^{12}$—$R^{10i}$,
(j) phenyl (which latter group is optionally substituted by one or more substituents selected from OH, halo, $C_{1-4}$ alkyl and $C_{1-4}$ alkoxy) or
(k) $Het^{11}$;

$R^{9a}$ to $R^{9i}$ and $R^{10a}$ to $R^{10i}$ independently represent, at each occurrence,
(a) H,
(b) $C_{1-12}$ alkyl, $C_{2-12}$ alkenyl, $C_{2-12}$ alkynyl, $C_{3-12}$ cycloalkyl, $C_{4-12}$ cycloalkenyl (which latter five groups are optionally substituted by one or more substituents selected from halo, OH, $C_{1-6}$ alkyl, $C_{3-12}$ cycloalkyl, $C_{4-12}$ cycloalkenyl (which latter two groups are optionally substituted by one or more substituents selected from OH, =O, halo, $C_{1-4}$ alkyl and $C_{1-4}$ alkoxy), $C_{1-6}$ alkoxy, $NH_2$, N(H)—$C_{1-6}$ alkyl, $N(C_{1-6}$ alkyl$)_2$, phenyl (which latter group is optionally substituted by one or more substituents selected from OH, halo, $C_{1-4}$ alkyl and $C_{1-4}$ alkoxy) and $Het^{12}$, and which $C_{3-12}$ cycloalkyl or $C_{4-12}$ cycloalkenyl groups may additionally be substituted by =O),
(c) phenyl (which latter group is optionally substituted by one or more substituents selected from OH, CN, halo, $C_{1-6}$ alkyl and $C_{1-6}$ alkoxy) or
(e) $Het^{13}$,
provided that $R^{9b}$ or $R^{10b}$ does not represent H when t or u, respectively is 1 or 2;

$Het^1$ to $Het^{13}$ independently represent 4- to 14-membered heterocyclic groups containing one or more heteroatoms selected from oxygen, nitrogen and/or sulfur, which heterocyclic groups may comprise one, two or three rings and may be substituted by one or more substituents selected from
(a) halo,
(b) CN,
(c) $C_{1-12}$ alkyl, $C_{2-12}$ alkenyl, $C_{2-12}$ alkynyl, $C_{3-12}$ cycloalkyl, $C_{4-12}$ cycloalkenyl, which latter five groups are optionally substituted by one or more substituents selected from halo, nitro, CN, $C_{1-6}$ alkyl, $C_{2-6}$ alkenyl, $C_{2-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{11a}$, $S(O)_vR^{11b}$, $S(O)_2N(R^{11c})(R^{11d})$, $N(R^{11e})S(O)_2R^{11f}$, $N(R^{11g})(R^{11h})$, $B^{13}$—C(O)—$B^{14}$—$R^{11i}$, phenyl, naphthyl (which latter two groups are optionally substituted by one or more substituents selected from OH, halo, $C_{1-4}$ alkyl and $C_{1-4}$ alkoxy) and $Het^a$, and which $C_{3-12}$ cycloalkyl or $C_{4-12}$ cycloalkenyl groups may additionally be substituted by =O,
(d) $OR^{12a}$,
(e) =O,
(f) $S(O)_wR^{12b}$,
(g) $S(O)_2N(R^{12c})(R^{12d})$,
(h) $N(R^{12e})S(O)_2R^{12f}$,
(i) $N(R^{12g})(R^{12h})$,
(j) $B^{15}$—C(O)—$B^{16}$—$R^{12i}$,
(k) phenyl (which latter group is optionally substituted by one or more substituents selected from OH, halo, $C_{1-4}$ alkyl and $C_{1-4}$ alkoxy) or
(l) $Het^b$;

$R^{11a}$ to $R^{11i}$ and $R^{12a}$ to $R^{12i}$ independently represent, at each occurrence,
(a) H,
(b) $C_{1-12}$ alkyl, $C_{2-12}$ alkenyl, $C_{2-12}$ alkynyl, $C_{3-12}$ cycloalkyl, $C_{4-12}$ cycloalkenyl (which latter five groups are optionally substituted by one or more substituents selected from halo, OH, $C_{1-6}$ alkyl, $C_{3-12}$ cycloalkyl, $C_{4-12}$ cycloalkenyl (which latter two groups are optionally substituted by one or more substituents selected from OH, =O, halo, $C_{1-4}$ alkyl and $C_{1-4}$ alkoxy), $C_{1-6}$ alkoxy, phenyl (which latter group is optionally substituted by one or more substituents selected from OH, halo, $C_{1-4}$ alkyl and $C_{1-4}$ alkoxy) and $Het^c$, and which $C_{3-12}$ cycloalkyl or $C_{4-12}$ cycloalkenyl groups may additionally be substituted by =O),
(c) phenyl (which latter group is optionally substituted by one or more substituents selected from OH, halo, $C_{1-4}$ alkyl and $C_{1-4}$ alkoxy) or
(e) $Het^d$,
provided that $R^{11b}$ or $R^{12b}$ does not represent H when v or w, respectively is 1 or 2;

$B^1$ to $B^{16}$ independently represent a direct bond, O, S, NH or $N(R^{13})$;

n, p, q, r, s, t, u, v and w independently represent 0, 1 or 2;

$R^{13}$ represents
(a) $C_{1-6}$ alkyl,
(b) phenyl (which latter group is optionally substituted by one or more substituents selected from OH, halo, $C_{1-4}$ alkyl and $C_{1-4}$ alkoxy),
(c) $C_{3-7}$ cycloalkyl (which latter group is are optionally substituted by one or more substituents selected from OH, =O, halo, $C_{1-4}$ alkyl and $C_{1-4}$ alkoxy) or
(e) $Het^e$;

$Het^a$ to $Het^e$ independently represent 5- or 6-membered heterocyclic groups containing one to four heteroatoms selected from oxygen, nitrogen and/or sulfur, which heterocyclic groups may be substituted by one or more substituents selected from halo, =O and $C_{1-6}$ alkyl; and unless otherwise specified
(i) alkyl, alkenyl, alkynyl, cycloalkyl, and cycloalkenyl groups, as well as the alkyl part of alkoxy groups, may be substituted by one or more halo atoms, and
(ii) cycloalkyl and cycloalkenyl groups may comprise one or two rings and may additionally be ring-fused to one or two benzene rings.

For the avoidance of doubt, each —X—$R^{4a}$ substituent is attached to the pyrrolidinyl ring via the X moiety.

When used herein, the term "pharmaceutically-acceptable derivative" includes references to:
(a) pharmaceutically-acceptable salts with either acids or bases (e.g. acid addition salts); and/or
(b) solvates (e.g. hydrates)

Acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalenesulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

The term "pharmaceutically-acceptable derivative" also includes references to:

(a) $C_{1-4}$ alkyl quaternary ammonium salts; or
(b) N-oxides, at either of the two tertiary N-atoms of the 4-(pyrrolidin-1-yl)quinoline ring system, or at a tertiary N-atom that may be present in any of substituents $R^1$, $R^2$ and $R^3$.

For the avoidance of doubt, the definitions of the terms aryl, alkyl, alkenyl, alkynyl, cycloalkyl, cycloalkenyl and alkoxy groups provided above apply, unless otherwise stated, at each usage of such terms herein. Further, the one or two benzene rings that may be fused to cycloalkyl groups may bear one or more of the substituents defined in respect of the relevant cycloalkyl group.

The term "halo", when used herein, includes fluoro, chloro, bromo and iodo.

Heterocyclic ($Het^1$ to $Het^{13}$ and $Het^a$ to $Het^e$) groups may be fully saturated, partly unsaturated, wholly aromatic or partly aromatic in character. Values of heterocyclic ($Het^1$ to $Het^{13}$ and $Het^a$ to $Het^e$) groups that may be mentioned include 1-azabicyclo-[2.2.2]octanyl, benzimidazolyl, benzo[c]isoxazolidinyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazolidinyl, benzoxazolyl, benzopyrazolyl, benzo[e]-pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo-[b]furanyl, 1,3-dihydrobenzo-[c]furanyl, 1,3-dihydro-2,1-benzisoxazolyl 2,3-dihydro-pyrrolo[2,3-b]pyridinyl, dioxanyl, furanyl, hexahydropyrimidinyl, hydantoinyl, imidazolyl, imidazo[1,2-a]pyridinyl, imidazo[2,3-b]thiazolyl, indolyl, isoquinolinyl, isoxazolidinyl, isoxazolyl, maleimido, morpholinyl, naphtho[1,2-b]furanyl, oxadiazolyl, 1,2- or 1,3-oxazinanyl, oxazolyl, phthalazinyl, piperazinyl, piperidinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]pyrimidine, tetrahydro-furanyl, tetrahydropyranyl, 3,4,5,6-tetrahydro-pyridinyl, 1,2,3,4-tetrahydropyrimidinyl, 3,4,5,6-tetrahydro-pyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl, xanthenyl and the like.

Values of $Het^2$ that may be mentioned include benzimidazolyl (e.g. benzimidazol-2-yl), piperidinyl (e.g. piperidin-4-yl), pyridinyl (e.g. pyridin-3-yl) and pyrrolidinyl (e.g. pyrrolidin-3-yl).

Values of $Het^6$ that may be mentioned include morpholinyl (e.g. morpholin-4-yl), piperidinyl (e.g. piperidin-4-yl) or, particularly, pyrrolidinonyl (e.g. 1-pyrrolidin-2-one).

Values of $Het^7$ that may be mentioned include isoxazolyl (e.g. isoxazol-3-yl) and pyridinyl (e.g. pyridin-3-yl).

Values of $Het^9$ that may be mentioned include piperidinyl (e.g. piperidin-1-yl) or, particularly, furanyl (e.g. furan-2-yl), imidazolyl (e.g. imidazol-5-yl), isoxazolyl (e.g. isoxazol-3-yl, isoxazol-4-yl or isoxazol-5-yl), pyrazinyl (e.g. pyrazin-2-yl), pyrazolyl (e.g. pyrazol-3-yl or pyrazol-4-yl), pyridazinyl (e.g. pyridazin-4-yl) or pyridinyl (e.g. pyridin-2-yl or pyridin-3-yl).

Values of $Het^{11}$ that may be mentioned include piperazinyl (e.g. piperazin-1-yl), piperidinyl (e.g. piperidin-1-yl) and pyridinyl (e.g. pyridin-3-yl).

Values of $Het^{13}$ that may be mentioned include pyridinyl (e.g. pyridin-3-yl).

When used herein, the term "microorganisms" means:
(a) fungi (as defined below); and, particularly
(b) bacteria (as defined below).

References herein to the terms "microbial", "antimicrobial" and "antimicrobially" shall be interpreted in accordance with the definition of "microorganisms". For example, the term "microbial" means fungal or, particularly, bacterial.

When used herein, the term "clinically latent" includes references to microorganisms that are viable but non-culturable (e.g. bacteria that cannot be detected by standard culture techniques but that are detectable and quantifiable by techniques such as broth dilution counting, microscopy, or molecular techniques such as polymerase chain reaction).

The term "clinically latent" also includes references to microorganisms that are phenotypically tolerant, for example microorganisms that:

(a) are sensitive (e.g. in log phase) to the biostatic (e.g. bacteriostatic) effects of conventional antimicrobial agents (i.e. microorganisms for which the minimum inhibitory concentration (MIC) of a conventional antimicrobial is substantially unchanged); but
(b) possess drastically decreased susceptibility to drug-induced killing (e.g. microorganisms for which, with any given conventional antimicrobial agent, the ratio of minimum microbicidal concentration (e.g. minimum bactericidal concentration, MBC) to MIC is 10 or more).

In relation to point (a) above, "substantially unchanged" refers to MIC values that are anywhere from 50 to 200% (e.g. 90 to 110%) of the value determined under standard conditions for the microorganism and conventional antimicrobial agent concerned.

For the avoidance of doubt, the term "clinically latent" excludes references to microorganisms that are genotypically resistant to conventional antimicrobial agents (i.e. microorganisms that differ genetically from antimicrobial-sensitive members of the same genus and that display an increased MIC (e.g. in log phase) for one or more conventional antimicrobial agents compared to said antimicrobial-sensitive microorganisms).

The term "clinically latent" further includes references to microorganisms that:
(i) are metabolically active; but
(ii) have a growth rate that is below the threshold of infectious disease expression.

The term "threshold of infectious disease expression" will be understood by those skilled in the art to include references to the growth rate threshold below which the symptoms of infectious disease (in a patient infected with the relevant microorganism) are absent.

In relation to point (i) above, metabolic activity of latent microorganisms can be determined by several methods known to those skilled in the art, for example by measuring mRNA levels in the microorganisms or by determining their rate of uridine uptake. In this respect, the term "clinically latent" further includes references to microorganisms that, compared to the same number of microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

When used herein, the term "conventional antimicrobial agent(s)" means:
(a) conventional antifungal agents; and, particularly
(b) conventional antibacterial agents,
wherein each of (a) and (b) is as defined below.

When used herein, the term "conventional antibacterial agent(s)" include references to bactericidal and bacteristatic agents that are known in the prior art (i.e. agents that have been selected and developed on the basis of their MICs—namely their ability to inhibit the growth of bacteria). In this respect, particular conventional antibacterial agents that may be mentioned include any one or more of the following.

(a) β-Lactams, including:
  (i) penicillins, such as
    (I) benzylpenicillin, procaine benzylpenicillin, phenoxy-methylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, azlocillin, carbenicillin, cloxacillin, D-(−)-penicillamine, dicloxacillin, nafcillin and oxacillin,
    (II) penicillinase-resistant penicillins (e.g. flucloxacillin),
    (III) broad-spectrum penicillins (e.g. ampicillin, amoxicillin, metampicillin and bacampicillin),
    (IV) antipseudomonal penicillins (e.g. carboxypenicillins such as ticarcillin or ureidopenicillins such as piperacillin),
    (V) mecillinams (e.g. pivmecillinam), or
    (VI) combinations of any two or more of the agents mentioned at (I) to (V) above, or combinations of any of the agents mentioned at (I) to (V) above with a β-lactamase inhibitor such as tazobactam or, particularly, clavulanic acid (which acid is optionally in metal salt form, e.g. in salt form with an alkali metal such as sodium or, particularly, potassium);
  (ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxil, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefinetazole, cefoperazone, cefsulodin, cephalosporin C zinc salt, cephalothin, cephapirin; and
  (iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and RO4908463 (CS-023)), penems (e.g. faropenem) and 1-oxa-β-lactams (e.g. moxalactam).

(b) Tetracyclines, such as tetracycline, demeclocycline, doxycycline, lymecycline, minocycline, oxytetracycline, chlortetracycline, meclocycline and methacycline, as well as glycylcyclines (e.g. tigecycline).

(c) Aminoglycosides, such as amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.

(d) (i) Macrolides, such as azithromycin, clarithromycin, erythromycin, roxithromycin, spiramycin, amphotericins B (e.g. amphotericin B), bafilomycins (e.g. bafilomycin A1), brefeldins (e.g. brefeldin A), concanamycins (e.g. concanamycin A), filipin complex, josamycin, mepartricin, midecamycin, nonactin, nystatin, oleandomycin, oligomycins (e.g. oligomycin A, oligomycin B and oligomycin C), pimaricin, rifampicin, rifamycin, rosamicin, tylosin, virginiamycin and fosfomycin.
(ii) Ketolides such as telithromycin and cethromycin (ABT-773).
(iii) Lincosamines, such as lincomycin.

(e) Clindamycin and clindamycin 2-phosphate.

(f) Phenicols, such as chloramphenicol and thiamphenicol.

(g) Steroids, such as fusidic acid (optionally in metal salt form, e.g. in salt form with an alkali metal such as sodium).

(h) Glycopeptides such as vancomycin, teicoplanin, bleomycin, phleomycin, ristomycin, telavancin, dalbavancin and oritavancin.

(i) Oxazolidinones, such as linezolid and AZD2563.

(j) Streptogramins, such as quinupristin and dalfopristin, or a combination thereof.

(k) (i) Peptides, such as polymyxins (e.g. colistin and polymyxin B), lysostaphin, duramycin, actinomycins (e.g. actinomycin C and actinomycin D), actinonin, 7-aminoactinomycin D, antimycin A, antipain, bacitracin, cyclosporin A, echinomycin, gramicidins (e.g. gramicidin A and gramicidin C), myxothiazol, nisin, paracelsin, valinomycin and viomycin.
(ii) Lipopeptides, such as daptomycin.
(iii) Lipoglycopeptides, such as ramoplanin.

(l) Sulfonamides, such as sulfamethoxazole, sulfadiazine, sulfaquinoxaline, sulfathiazole (which latter two agents are optionally in metal salt form, e.g. in salt form with an alkali metal such as sodium), succinylsulfathiazole, sulfadimethoxine, sulfaguanidine, sulfamethazine, sulfamonomethoxine, sulfanilamide and sulfasalazine.

(m) Trimethoprim, optionally in combination with a sulfonamide, such as sulfamethoxazole (e.g. the combination cotrimoxazole).

(n) Antituberculous drugs, such as isoniazid, rifampicin, rifabutin, pyrazinamide, ethambutol, streptomycin, amikacin, capreomycin, kanamycin, quinolones (e.g. those at (q) below), para-aminosalicylic acid, cycloserine and ethionamide.

(o) Antileprotic drugs, such as dapsone, rifampicin and clofazimine.

(p) (i) Nitroimidazoles, such as metronidazole and timidazole.
(ii) Nitrofurans, such as nitrofurantoin.

(q) Quinolones, such as nalidixic acid, norfloxacin, ciprofloxacin, ofloxacin, levofloxacin, moxifloxacin, gatifloxacin, gemifloxacin, garenoxacin, DX-619, WCK 771 (the arginine salt of S-(−)-nadifloxacin), 8-quinolinol, cinoxacin, enrofloxacin, flumequine, lomefloxacin, oxolinic acid and pipemidic acid.

(r) Amino acid derivatives, such as azaserine, bestatin, D-cycloserine, 1,10-phenanthroline, 6-diazo-5-oxo-L-norleucine and L-alanyl-L-1-aminoethyl-phosphonic acid.

(s) Aureolic acids, such as chromomycin A3, mithramycin A and mitomycin C.

(t) Benzochinoides, such as herbimycin A.
(u) Coumarin-glycosides, such as novobiocin.
(v) Diphenyl ether derivatives, such as irgasan.
(w) Epipolythiodixopiperazines, such as gliotoxin from *Gliocladium fimbriatum*.
(x) Fatty acid derivatives, such as cerulenin.
(y) Glucosamines, such as 1-deoxymannojirimycin, 1-deoxynojirimycin and N-methyl-1-deoxynojirimycin.
(z) Indole derivatives, such as staurosporine.
(aa) Diaminopyrimidines, such as iclaprim (AR-100).
(ab) Macrolactams, such as ascomycin.
(ac) Taxoids, such as paclitaxel.
(ad) Statins, such as mevastatin.
(ae) Polyphenolic acids, such as (+)-usnic acid.
(af) Polyethers, such as lasalocid A, lonomycin A, monensin, nigericin and salinomycin.
(ag) Picolinic acid derivatives, such as fusaric acid.
(ah) Peptidyl nucleosides, such as blasticidine S, nikkomycin, nourseothricin and puromycin.
(ai) Nucleosides, such as adenine 9-β-D-arabinofuranoside, 5-azacytidine, cordycepin, formycin A, tubercidin and tunicamycin.
(aj) Pleuromutilins, such as GSK-565154, GSK-275833 and tiamulin.
(ak) Peptide deformylase inhibitors, such as LBM415 (NVP PDF-713) and BB 83698.
(al) Antibacterial agents for the skin, such as fucidin, benzamycin, clindamycin, erythromycin, tetracycline, silver sulfadiazine, chlortetracycline, metronidazole, mupirocin, framycitin, gramicidin, neomycin sulfate, polymyxins (e.g. polymixin B) and gentamycin;
(am) Miscellaneous agents, such as methenamine (hexamine), doxorubicin, piericidin A, stigmatellin, actidione, anisomycin, apramycin, coumermycin A1, L(+)-lactic acid, cytochalasins (e.g. cytochalasin B and cytochalasin D), emetine and ionomycin.

Particular conventional antibacterial agents that may be mentioned include those listed at (a) to (q) above, such as:
the -cillins listed at (a)(i) above (e.g. amoxicillin, ampicillin, phenoxymethylpenicillin or, particularly, co-amoxiclav (co-amoxicillin));
the cephalosporins listed at (a)(ii) above (e.g. cefuroxime, cefaclor or cefalexin);
the carbapenems listed at (a)(iii) above (e.g. ertapenem);
the tetracyclines listed at (b) above (e.g. doxycycline or minocycline);
the macrolides listed at (d)(i) above (e.g. clarithromycin, erythromycin, roxithromycin or, particularly, azithromycin);
the ketolides listed at (d) (ii) above (e.g. telithromycin);
the oxazolidinones listed at (i) above (e.g. linezolid);
the lipopeptides listed at (k)(ii) above (e.g. daptomycin) trimethoprim and the combinations therewith (e.g. co-trimoxazol) listed at (m) above;
the nitrofurans listed at (p) above (e.g. nitrofurantoin); and
the quinolones listed at (q) above (e.g. norfloxacin, ciprofloxacin, ofloxacin, or, particularly, levofloxacin or moxifloxacin).

When used herein, the term "conventional antifungal agent(s)" include references to fungicidal and fungistatic agents that are known in the prior art (i.e. agents that have been selected and developed on the basis of their MICs—namely their ability to inhibit the growth of fungi). In this respect, particular conventional antifungal agents that may be mentioned include any one or more of the following.

(a) azole antifungals, such as imidazoles (e.g. clotrimazole, econazole, fenticonazole, ketoconazole, miconazole, sulconazole, and tioconazole) or triazoles (e.g. fluconazole, itraconazole and voriconazole);
(b) polyene antifungals, such as amphotericin and nystatin;
(c) miscellaneous antifungal agents such as griseofulvin, caspofungin or flucytosine, which latter two agents are optionally employed in combination;
(d) allylamine antifungals, such as terbinafine.

Embodiments of the compounds of formula I that may be mentioned include those in which:
(1) $R^1$ represents one to four substituents (e.g. two substituents or, particularly, one substituent), in at least one of which $R^{4a}$ and/or $R^{4b}$ is other than H;
(2) $R^{4a}$ represents
  (a) $C_{1-12}$ alkyl, $C_{3-12}$ cycloalkyl, $C_{3-12}$ cycloalkenyl (which latter three groups are substituted by an aryl or $Het^1$ group and are optionally further substituted by one or more substituents selected from halo, nitro, CN, $C_{1-6}$ alkyl, $C_{2-8}$ alkenyl, $C_{2-6}$ alkynyl, cycloalkyl (which latter three groups are optionally substituted by one or more substituents selected from OH, =O, halo, $C_{1-4}$ alkyl and $C_{1-4}$ alkoxy), $OR^{5a}$, $S(O)_nR^{5b}$, $S(O)_2N(R^{5c})(R^{5d})$, $N(R^{5e})S(O)_2R^{5f}$, $N(R^{5g})(R^{5h})$, $B^1$—C(O)—$B^2$—$R^{5i}$, aryl and $Het^1$, and which $C_{3-12}$ cycloalkyl or $C_{4-12}$ cycloalkenyl groups may additionally be substituted by =O),
  (c) aryl or
  (d) $Het^2$;
(3) $R^2$ is other than H.

Further embodiments of the compounds of formula I that may be mentioned include those in which:
(1) $R^1$ represents two substituents or, particularly, one substituent on the pyrrolidinyl ring, each substituent independently representing the group —X—$R^{4a}$;
(2) X represents a direct bond, —O— or —N(H)— (e.g. a direct bond or —N(H)—);
(3) $R^{4a}$ represents
  (a) $C_{1-8}$ alkyl (e.g. $C_{1-6}$ or $C_{1-4}$ alkyl, such as methyl) or $C_{4-6}$ cycloalkyl, which alkyl or cycloalkyl group is optionally substituted by one or more substituents selected from halo, nitro, CN, $C_{1-2}$ alkyl, $C_{4-6}$ cycloalkyl (which latter group is optionally substituted by one or more substituents selected from =O, halo, methyl and methoxy), $OR^{5a}$, phenyl, naphthyl (which latter two groups are optionally substituted by one or more (e.g. one to four) substituents selected from halo, CN, $C_{1-6}$ alkyl, $C_{2-6}$ alkenyl, $C_{2-6}$ alkynyl or $C_{3-6}$ cycloalkyl, $OR^{10a}$, $S(O)_2R^{10b}$ and —C(O)$R^{10i}$), or
  (b) phenyl or naphthyl (which latter two groups are optionally substituted by one or more (e.g. one to four) substituents selected from halo, CN, $C_{1-6}$ alkyl, $C_{2-6}$ alkenyl, $C_{2-6}$ alkynyl or $C_{3-6}$ cycloalkyl, $OR^{10a}$, $S(O)_2R^{10b}$ and —C(O)$R^{10i}$);
(4) $R^2$ represents
  (a) H,
  (b) $C_{1-8}$ alkyl (e.g. $C_{1-6}$ alkyl, such as $C_{1-4}$ alkyl or, particularly, methyl), $C_{2-8}$ alkenyl, $C_{2-8}$ alkynyl, $C_{3-6}$ cycloalkyl, which latter four groups are optionally substituted by one or more substituents selected from halo, methyl and methoxy;
(5) $R^3$ represents H or one to four (e.g. two or, particularly, one) substituents on the fused benzene ring (e.g. one to four substituents including at least one substituent at the 6-position of the quinoline or quinazoline ring system) selected from
  (a) halo,
  (b) CN, (c) $C_{1-6}$ alkyl, $C_{2-6}$ alkenyl, $C_{2-6}$ alkynyl, $C_{4-6}$ cycloalkyl, which latter four groups are optionally substituted by one or more substituents selected from halo, nitro, CN, $C_{1-3}$ alkyl, $C_{2-3}$ alkenyl, $C_{2-3}$ alkynyl, $C_{4-6}$ cycloalkyl $OR^{7a}$, $N(H)S(O)_2R^{7f}$, $N(H)(R^{7h})$, —$C(O)R^{7i}$, aryl and $Het^5$,
(d) $OR^{8a}$,
(e) $S(O)_2R^{8b}$,
(f) $S(O)_2N(R^{8c})(R^{8d})$,
(g) $N(R^{8e})S(O)_2R^{8f}$,
(h) $N(R^{8g})(R^{8h})$,
(i) —$C(O)R^{8i}$, —$N(R^{13})C(O)R^{8i}$, $OC(O)R^{8i}$, $C(O)N(H)R^{8i}$, $C(O)OR^{8i}$,
(j) aryl or
(k) $Het^6$;

(6) $R^{5a}$ represents, at each occurrence,
  (a) $C_{1-6}$ alkyl, $C_{2-6}$ alkenyl, $C_{2-6}$ alkynyl (which latter three groups are optionally substituted by one or more substituents selected from halo, alkoxy, phenyl and naphthyl, which latter two groups are optionally substituted by one or more (e.g. one to four) substituents selected from halo, CN, $C_{1-6}$ alkyl, $C_{2-6}$ alkenyl, $C_{2-6}$ alkynyl or $C_{3-6}$ cycloalkyl, $OR^{10a}$, $S(O)_2R^{10b}$ and —$C(O)R^{10i}$),
  (b) $C_{3-6}$ cycloalkyl (which latter group is optionally substituted by one or more substituents selected from halo, =O, methyl, methoxy and phenyl),
  (c) phenyl or naphthyl (which latter two groups are optionally substituted by one or more (e.g. one to four) substituents selected from halo, CN, $C_{1-6}$ alkyl, $C_{2-6}$ alkenyl, $C_{2-6}$ alkynyl or $C_{3-6}$ cycloalkyl, $OR^{10a}$, $S(O)_2R^{10b}$ and —$C(O)R^{10i}$);

(7) $R^{7a}$ to $R^{7i}$ and $R^{8a}$ to $R^{8i}$ independently represent, at each occurrence,
  (a) H,
  (b) $C_{1-6}$ alkyl, $C_{2-6}$ alkenyl, $C_{2-6}$ alkynyl (which latter three groups are optionally substituted by one or more substituents selected from halo, OH, methoxy, aryl and $Het^7$),
  (c) $C_{4-6}$ cycloalkyl (which latter group is optionally substituted by one or more substituents selected from halo, OH, =O, methyl, methoxy, aryl and $Het^8$),
  (d) aryl or
  (e) $Het^9$,
  provided that $R^{7b}$ or $R^{6b}$ does not represent H when q or r, respectively is 1 or 2;

(8) $R^{10a}$, $R^{10b}$ and $R^{10i}$ independently represent, at each occurrence,
  (a) $C_{1-6}$ alkyl, $C_{2-6}$ alkenyl, $C_{2-6}$ alkynyl, $C_{4-6}$ cycloalkyl (which latter four groups are optionally substituted by one or more substituents selected from halo, methyl and methoxy) or
  (c) phenyl (which latter group is optionally substituted by one or more substituents selected from CN, halo, $C_{1-2}$ alkyl and $C_{1-2}$ alkoxy);

(9) $Het^6$ represents a 4- to 7-membered aromatic, partially unsaturated or, particularly, fully saturated heterocyclic group containing one nitrogen atom (which atom may form the point of attachment of the $Het^6$ group to the rest of the molecule) and, optionally, one or two further heteroatoms selected from oxygen, nitrogen and/or sulfur, which heterocyclic group may be substituted by one or more substituents selected from halo, methyl, methoxy and =O;

(10) $Het^7$ to $Het^9$ independently represent 5- to 10-membered aromatic heterocyclic groups containing one or more (e.g. one to three) heteroatoms selected from oxygen, nitrogen and/or sulfur, which heterocyclic groups may comprise one or two rings and may be substituted by one or more (e.g. one or two) substituents selected from
  (a) halo,
  (b) CN,
  (c) $C_{1-8}$ alkyl (e.g. $C_{1-6}$ alkyl, such as $C_{1-4}$ alkyl or, particularly, methyl), $C_{2-8}$ alkenyl, $C_{2-8}$ alkynyl, $C_{4-6}$ cycloalkyl, which latter four groups are optionally substituted by one or more substituents selected from halo, methyl and methoxy,
  (d) $OR^{12a}$,
  (i) $N(H)(R^{12h})$,
  (j) —$C(O)R^{12i}$, —$N(H)C(O)R^{12i}$, —$OC(O)R^{12i}$, —$C(O)N(H)R^{12i}$, —$C(O)OR^{12i}$,
  (k) phenyl (which latter group is optionally substituted by one or more substituents selected from OH, halo, methyl and methoxy) or
  (l) $Het^b$;

(11) $R^{12a}$, $R^{12h}$ and $R^{12i}$ independently represent, at each occurrence, H, $C_{1-2}$ alkyl or phenyl (which latter group is optionally substituted by one or more substituents selected from OH, halo, methyl and methoxy);

(12) $R^{13}$ represents $C_{1-3}$ alkyl (e.g. methyl) or, particularly, H;

(13) $Het^b$ represents a 5- or 6-membered aromatic heterocycle containing one to three heteroatoms selected from nitrogen and oxygen, which heterocyclic group is optionally substituted by one to three substituents selected from halo and methyl;

(14) unless otherwise specified, alkyl, alkenyl, alkynyl, cycloalkyl, and cycloalkenyl groups, as well as the alkyl part of alkoxy groups, are unsubstituted;

(15) unless otherwise specified, cycloalkyl groups comprise one or (if sufficient number of C-atoms is present) two rings and are optionally ring-fused to a benzene ring (so as to form a group such as, for example, 1,2,3,4-tetrahydronaphthyl or, particularly, indanyl).

Further embodiments of the compounds of formula I that may be mentioned include those in which:

(1) E represents CH;
(2) $R^1$ represents one —X—$R^{4a}$ substituent on the pyrrolidinyl ring (e.g. a substituent at the 3-position of the ring);
(3) X represents a direct bond or —N(H)—;
(4) $R^{4a}$ represents
  (a) $C_{1-2}$ alkyl (such as methyl), which alkyl group is substituted by one or more substituents selected from phenyl (which latter group is optionally substituted by one or more (e.g. two or, particularly, one) substituents selected from halo (e.g. chloro), CN, $C_{1-3}$ alkyl and $OR^{10a}$), or
  (b) phenyl (which latter group is optionally substituted by one or more (e.g. two or, particularly, one) substituents selected from halo (e.g. chloro), CN, $C_{1-3}$ alkyl and $OR^{10a}$);
(5) $R^2$ represents $C_{1-2}$ alkyl, such as methyl;
(6) $R^3$ represents one to four substituents on the fused benzene ring including at least one substituent at the 6-position of the quinoline or quinazoline ring system, wherein each substituent is independently selected from
  (a) halo (e.g. chloro),
  (b) $OR^{8a}$,
  (c) $N(H)S(O)_2R^{8f}$,
  (d) $N(H)(R^{8h})$,
  (e) —$N(H)C(O)R^{8i}$, $C(O)N(H)R^{8i}$ or
  (f) $Het^6$;
(7) $R^{8a}$ to $R^{8i}$ independently represent, at each occurrence,
  (a) $C_{1-4}$ alkyl (e.g. methyl or ethyl) optionally substituted by phenyl (which latter group is optionally substituted by one or more substituents selected from halo, CN, $C_{1-2}$ alkyl, methoxy, ethoxy and $S(O)_2$—($C_{1-2}$ alkyl)) or Het$^7$,
(b) phenyl (which latter group is optionally substituted by one or more substituents selected from halo, CN, $C_{1-2}$ alkyl, methoxy, ethoxy and $S(O)_2$—($C_{1-2}$ alkyl)) or
(e) Het$^9$;
(8) $R^{10a}$ represents $C_{1-4}$ alkyl (e.g. methyl);
(9) Het$^6$ represents a 5- or 6-membered, fully saturated heterocyclic group containing one nitrogen atom (which atom forms the point of attachment of the Het$^6$ group to the rest of the molecule) and, optionally, one further heteroatom selected from oxygen and nitrogen, which heterocyclic group may be substituted by one or more substituents selected from halo, methyl, and =O;
(10) Het$^7$ to Het$^9$ independently represent 5- or 6-membered aromatic heterocyclic groups containing one to three (e.g. one or two) heteroatoms selected from oxygen, nitrogen and/or sulfur (e.g. selected from oxygen and/or nitrogen), which heterocyclic groups may be substituted by one or more (e.g. one or two) substituents selected from halo, CN and $C_{1-2}$ alkyl (e.g. methyl).

In particular embodiments of the invention, the compound of formula I is a compound of formula Ia,

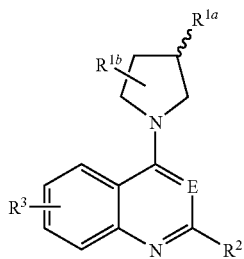

Ia wherein $R^{1a}$ represents —X—$R^{4a}$;
$R^{1b}$ represents H or one or two substituents on the pyrrolidinyl ring, each substituent independently representing the group —X—$R^{4a}$;
and E, X, $R^2$, $R^3$ and $R^{4a}$ are as hereinbefore defined.

Hereinafter, references to compounds of formula I are, unless the context indicates otherwise, intended to include references to compounds of formula Ia. Conversely, where reference is made to particular embodiments of the compounds of formula Ia, these embodiments apply equally, where relevant, to compounds of formula I.

Embodiments of the compounds of formula Ia that may be mentioned include those in which the structural fragment

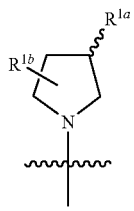

is in the:
(a) R— configuration at the C-atom to which $R^{1a}$ is attached; or
(b) S— configuration at the C-atom to which $R^{1a}$ is attached.

Further embodiments of the compounds of formula Ia that may be mentioned include those in which:
(1) E represents CH;
(2) $R^{1b}$ represents H;
(3) —X—$R^{4a}$ represents
  (a) phenyl (which latter group is optionally substituted by one or more (e.g. two or, particularly, one) substituents selected from halo (e.g. chloro) and methoxy),
  (b) $CH_2$-phenyl (the phenyl part of which group is optionally substituted by one or more (e.g. two or, particularly, one) substituents selected from halo (e.g. chloro) and methoxy, but, in a particular embodiment, is unsubstituted) or
  (c) NH-phenyl (the phenyl part of which group is optionally substituted by one or more (e.g. two or, particularly, one) substituents selected from halo (e.g. chloro) and methoxy, but, in a particular embodiment, is unsubstituted);
(4) $R^2$ represents methyl;
(5) $R^3$ represents one or two substituents (e.g. one substituent) on the fused benzene ring including at least one substituent at the 6-position of the quinoline or quinazoline ring system, wherein each substituent is independently selected from halo (e.g. chloro), $OR^{8a}$, $N(H)S(O)_2R^{8f}$, $N(H)(R^{8h})$, —$N(H)C(O)R^{8i}$ or Het$^6$ (e.g. each substituent is independently selected from $OR^{8a}$, $N(H)(R^{8h})$, —$N(H)C(O)R^{8i}$ or Het$^6$);
(6) $R^{8a}$ represents
  (a) phenyl optionally substituted by one to three substituents (e.g. one substituent, such as one substituent at the 2- or, particularly the 4-position) selected from halo, CN, methyl, methoxy and $S(O)_2CH_3$ (e.g. selected from methoxy and $S(O)_2CH_3$),
  (b) $C_{1-2}$ alkyl substituted by phenyl, which latter group is optionally substituted by one to three substituents (e.g. one substituent, such as one substituent at the 2- or, particularly the 4-position) selected from halo, CN, methyl, methoxy and $S(O)_2CH_3$ (e.g. selected from methoxy and $S(O)_2CH_3$) or
  (c) $C_{1-2}$ alkyl substituted by Het$^7$;
(7) $R^{8f}$ represents phenyl optionally substituted by one to three substituents (e.g. one substituent, such as one substituent at the 2- or, particularly the 4-position) selected from halo, CN, methyl, methoxy and $S(O)_2CH_3$;
(8) $R^{8h}$ represents $C_{1-2}$ alkyl (e.g. methyl) substituted by phenyl, which latter group is optionally substituted by one to three substituents (e.g. one substituent, such as one substituent at the 2- or, particularly the 4-position) selected from halo, CN, methyl, methoxy and $S(O)_2CH_3$ (e.g. selected from CN and methoxy);
(6) $R^{8i}$ represents
  (a) phenyl optionally substituted by one to three substituents (e.g. one substituent, such as one substituent at the 2- or, particularly the 4-position) selected from halo, CN, methyl, methoxy and $S(O)_2CH_3$ (e.g. selected from chloro, methyl and methoxy),
  (b) $C_{1-3}$ alkyl (e.g. methyl or ethyl) substituted by phenyl, which latter group is optionally substituted by one to three substituents (e.g. one substituent, such as one substituent at the 2- or, particularly the 4-position) selected from halo, CN, methyl, methoxy and $S(O)_2CH_3$ (e.g. selected from chloro, methyl and methoxy),
  (c) $C_{1-2}$ alkyl substituted by Het$^7$ or
  (d) Het$^9$;

(9) Het⁶ represents pyrrolidin-1-yl substituted by one to three substituents (e.g. one substituent, such as a single substituent at the 2-position) selected from halo, methyl, and =O (e.g. an =O substituent);

(10) Het⁷ and Het⁹ independently represent 5- or 6-membered aromatic heterocyclic groups containing one to three (e.g. one or two) heteroatoms selected from oxygen and/or nitrogen, which heterocyclic groups may be substituted by one or more (e.g. one or two) substituents selected from halo and methyl (e.g. substituted by two or, particularly, one methyl group).

Specific values of $R^{1a}$ that may be mentioned in relation to compounds of formula Ia include phenyl, 4-methoxyphenyl, 4-chlorophenyl, benzyl and phenylamino.

Specific values of $R^3$ (e.g. as a single substituent at the 6-position of the quinoline or quinazoline ring system) that may be mentioned in relation to compounds of formula I include:
chloro;
phenoxy;
benzyloxy; 4-methanesulfonylbenzylm; 4-methoxybenzyloxy;
2-phenylethoxy;
5-methylisoxazol-3-ylmethoxy;
benzylamino; (4-cyanobenzyl)amino; (4-methoxybenzyl)amino;
phenylcarbonylamino; (4-chlorophenyl)carbonylamino; (4-methoxy-phenyl)carbonylamino; (2-methylphenyl)carbonylamino;
phenylmethylcarbonylamino; (4-chlorophenyl)methylcarbonylamino;
(4-methoxyphenyl)methylcarbonylamino;
furan-2-ylcarbonylamino;
3-methyl-3H-imidazole-4-ylcarbonylamino;
5-methyl-isoxazole-3-ylcarbonylamino; 3,5-dimethyl-isoxazole-4-yl-carbonylamino;
2-phenylethylcarbonylamino;
pyrazine-2-ylcarbonylamino;
5-methyl-1H-pyrazole-3-ylcarbonylamino; 1H-pyrazole-4-ylcarbonyl-amino;
pyridazine-4-ylcarbonylamino;
pyridine-2-ylcarbonylamino; pyridin-3-ylcarbonylamino;
2-(3-methyl-isoxazol-5-yl)methylcarbonylamino;
benzenesulfonylamino; and
2-oxopyrrolidin-1-yl.

Embodiments of the invention that may be mentioned include those in which the compound of formula I is a compound of Examples 1 to 39 below, such as:
2-methyl-6-phenethyloxy-4-(3-phenylpyrrolidin-1-yl)quinoline;
4-(3-benzylpyrrolidin-1-yl)-2-methyl-6-phenoxyquinoline;
4-[3-(4-methoxyphenyl)pyrrolidin-1-yl]-2-methyl-6-phenoxyquinoline hydrochloride;
5-methyl-1H-pyrazole-3-carboxylic acid [2-methyl-4-(3-phenylpyrrolidin-1-yl)-quinolin-6-yl]amide; or
N-[4-(3-benzylpyrrolidin-1-yl)-2-methylquinolin-6-yl]benzamide,
or a pharmaceutically-acceptable derivative thereof.

Further embodiments of the invention that may be mentioned include those in which the compound of formula I is a compound of formula Ia wherein the compound is in the R— configuration at the C-atom to which $R^{1a}$ is attached, and is selected from:
(i) 4-((R)-3-benzylpyrrolidin-1-yl)-2-methyl-6-phenoxyquinoline;
(ii) 4-[(R)-3-(4-methoxyphenyl)pyrrolidin-1-yl]-2-methyl-6-phenoxyquinoline;
(iii) 5-methyl-1H-pyrazole-3-carboxylic acid [2-methyl-4-((R)-3-phenyl-pyrrolidin-1-yl)-quinolin-6-yl]amide; and
(iv) N-[4-((R)-3-benzylpyrrolidin-1-yl)-2-methylquinolin-6-yl]benzamide,
or a pharmaceutically-acceptable derivative thereof.

Particular compounds that may be mentioned in this respect include compounds (i) and (iv) above, and pharmaceutically-acceptable derivatives thereof.

Still further embodiments of the invention that may be mentioned include those in which the compound of formula I is a compound of formula Ia wherein the compound is in the S— configuration at the C-atom to which $R^{1a}$ is attached, and is selected from:
(I) 4-((S)-3-benzylpyrrolidin-1-yl)-2-methyl-6-phenoxyquinoline;
(II) 4-[(S)-3-(4-methoxyphenyl)pyrrolidin-1-yl]-2-methyl-6-phenoxyquinoline;
(III) 5-methyl-1H-pyrazole-3-carboxylic acid [2-methyl-4-((S)-3-phenyl-pyrrolidin-1-yl)-quinolin-6-yl]amide; and
(IV) N-[4-((S)-3-benzylpyrrolidin-1-yl)-2-methylquinolin-6-yl]benzamide,
or a pharmaceutically-acceptable derivative thereof.

Particular compounds that may be mentioned in this respect include compounds (I) and (IV) above, and pharmaceutically acceptable derivatives thereof.

The medicament mentioned in the first aspect of the invention may be utilised in a method of medical treatment. Thus, according to a second aspect of the invention, there is provided:

(i) a method of killing clinically latent microorganisms in a mammal infected with such latent microorganisms, the method comprising administering to said mammal a microbicidally effective amount of compound of formula I, as hereinbefore defined; and (ii) a compound of formula I, as hereinbefore defined, for use in the killing of clinically latent microorganisms in a mammal infected with such latent microorganisms.

Furthermore, the compound of formula I may be used to kill clinically latent microorganisms. Thus, according to a third aspect of the invention, there is provided the use of a compound of formula I, as hereinbefore defined, to kill clinically latent microorganisms. In one embodiment, the use according to this aspect of the invention is an ex vivo use.

In addition to killing clinically latent microorganisms, the inventors have discovered that compounds of formula I are able to kill microorganisms of many different phenotypes, including growing microorganisms.

In this respect, fourth, fifth, sixth and seventh aspects of the invention provide, respectively:

(a) the use of a compound of formula I, as hereinbefore defined, for the preparation of a medicament for the treatment or prevention of a microbial infection;

(b) a method of treating or preventing a microbial infection in a mammal, the method comprising administering to said mammal an antimicrobially effective amount of a compound of formula I, as hereinbefore defined;

(c) use (e.g. ex vivo use) of a compound of formula I to kill microorganisms;

(d) a compound of formula I, as hereinbefore defined for use in the treatment or prevention of a microbial infection in a mammal.

For the avoidance of doubt, as used herein, the term "treatment" includes therapeutic and/or prophylactic treatment.

As mentioned above, the uses according to the third and sixth aspects of the invention may be ex vivo uses, such as the use of a compound of formula I, as hereinbefore defined:

(a) as a sterilising agent; or
(b) as a preservative.

Conversely, the compounds of formula I may be employed in methods of sterilisation or preservation, such as:
(i) a method of sterilising an object, the method comprising applying to said object a compound of formula I, as hereinbefore defined; or
(ii) a method of preserving an inorganic or, preferably, an organic material, said method comprising contacting, combining or mixing said material with a compound of formula I, as hereinbefore defined.

In relation to the method described at (i) above, the object is preferably other than a human or animal body. Further, the materials that may be preserved according to the method described at (ii) above include polymers, lubricants, paints, fibres, leather, paper, foodstuffs, water and aqueous mixtures and solutions.

When used to kill clinically latent microorganisms or to treat a microbial infection, the compounds of formula I may be used either alone (i.e. as sole microbicidal or antimicrobial agents) or in combination with any one or more of the conventional antimicrobial agents described above.

Further, when used as a sterilising agent, the compounds of formula I may be used either alone or in combination with a conventional sterilising agent. The term "conventional sterilising agent", when used herein, includes references to alcohols (e.g. industrial methylated spirits or ethanol), sodium chloride, thymol, chlorhexidine, cationic surfactants (e.g. cetrimide), iodine (optionally combined with povidone), phenolics (e.g. triclosan), oxidants (e.g. hydrogen peroxide, potassium permanganate or sodium hypochlorite) and any one or more of the conventional antimicrobial agents described above.

Thus, according to eighth and ninth aspects of the invention, there is provided, respectively:
(i) a combination product comprising
    (A) a compound of formula I, as hereinbefore defined, and
    (B) a conventional antimicrobial agent, as hereinbefore defined, wherein each of components (A) and (B) is formulated in admixture with a pharmaceutically-acceptable adjuvant, diluent or carrier; and
(b) a formulation comprising a compound of formula I, as hereinbefore defined and a conventional sterilising agent, as hereinbefore defined, or a salt and/or solvate thereof.

The combination product according to the eighth aspect of the invention provides for the administration of component (A) in conjunction with component (B), and may thus be presented either as separate formulations, wherein at least one of those formulations comprises component (A) and at least one comprises component (B), or may be presented (i.e. formulated) as a combined preparation (i.e. presented as a single formulation including component (A) and component (B)).

Thus, there is further provided:
(1) a pharmaceutical formulation including a compound of formula I, as hereinbefore defined and a conventional antimicrobial agent, as hereinbefore defined, or a pharmaceutically-acceptable derivative thereof, in admixture with a pharmaceutically-acceptable adjuvant, diluent or carrier (which formulation is hereinafter referred to as a "combined preparation"); and
(2) a kit of parts comprising components:
    (I) a pharmaceutical formulation including a compound of formula I, as hereinbefore defined, in admixture with a pharmaceutically-acceptable adjuvant, diluent or carrier; and
    (II) a pharmaceutical formulation including a conventional antimicrobial agent, as hereinbefore defined, or a pharmaceutically-acceptable derivative thereof, in admixture with a pharmaceutically-acceptable adjuvant, diluent or carrier,
    which components (I) and (II) are each provided in a form that is suitable for administration in conjunction with the other.

Component (I) of the kit of parts is thus component (A) in admixture with a pharmaceutically-acceptable adjuvant, diluent or carrier. Similarly, component (II) is component (B) in admixture with a pharmaceutically-acceptable adjuvant, diluent or carrier.

According to a tenth aspect of the invention, there is provided a method of making a kit of parts as defined above, which method comprises bringing a component (I), as defined above, into association with a component (II), as defined above, thus rendering the two components suitable for administration in conjunction with each other.

By bringing the two components "into association with" each other, we include that components (I) and (II) of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(1) one of components (I) and (II) as defined herein; together with
(2) instructions to use that component in conjunction with the other of the two components.

The kits of parts described herein may comprise more than one formulation including an appropriate quantity/dose of component (A), and/or more than one formulation including an appropriate quantity/dose of component (B), in order to provide for repeat dosing. If more than one formulation (comprising either active compound) is present, such formulations may be the same, or may be different in terms of the dose of component (A) or component (B), chemical composition and/or physical form.

The combination product according to the eighth aspect of the invention may be used to kill clinically latent microorganisms and/or treat a microbial infection. Thus, further aspects of the invention provide:
(i) the use of a combination product according to the eighth aspect of the invention for the preparation of a medicament for killing clinically latent microorganisms;
(ii) a method of killing clinically latent microorganisms in a mammal infected with such latent microorganisms, the method comprising administering to said mammal a microbicidally effective amount of a combination product according to the eighth aspect of the invention;
(iii) a combination product according to the eighth aspect of the invention for use in the killing of clinically latent microorganisms in a mammal infected with such latent microorganisms;
(iv) the use of a combination product according to the eighth aspect of the invention for the preparation of a medicament for treating or preventing a microbial infection;
(v) a method of treating or preventing a microbial infection in a mammal, the method comprising administering to said mammal an antimicrobially effective amount of a combination product according to the eighth aspect of the invention; and (vi) a combination product according to the eighth aspect of the invention for use in the treatment or prevention of a microbial infection in a mammal.

The method of (v) above provides for the advantage that the amount of conventional antimicrobial agent required to treat the microbial infection is reduced compared to that required in the absence of a compound of formula I.

When used herein, the terms "bacteria" (and derivatives thereof, such as "bacterial infection") includes references to organisms (or infections due to organisms) of the following classes and specific types:

Gram-positive cocci, such as
  Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*) and
  Streptococci (e.g.
    beta-haemolytic, pyogenic streptococci (such as *Strept. agalactiae, Strept. canis, Strept. dysgalactiae dysgalactiae, Strept dysgalactiae equisimilis, Strept equi equi, Strept equi zooepidemicus, Strept. iniae, Strept porcinus* and *Strept pyogenes*),
    microaerophilic, pyogenic streptococci (*Streptococcus* "milleri", such as *Strept anginosus, Strept constellatus constellatus, Strept constellatus pharyngidis* and *Strept. intermedius*),
    oral streptococci of the "mitis" (alpha-haemolytic—*Streptococcus* "viridans", such as *Strept. mitis, Strept. oxalis, Strept. sanguinis, Strept. cristatus, Strept. gordonii* and *Strept. parasanguinis*), "salivarius" (non-haemolytic, such as *Strept salivarius* and *Strept vestibularis*) and "mutans" (tooth-surface streptococci, such as *Strept. criceti, Strept. mutans, Strept ratti* and *Strept sobrinus*) groups,
    *Strept. acidominimus, Strept. bovis, Strept. faecalis, Strept. equinus, Strept pneumoniae* and *Strept suis*,
    or Streptococci alternatively classified as Group A, B, C, D, E, G, L, P, U or V *Streptococcus*);
Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri;*
Bacillaceae, such as *Bacillus anthracis, Bacillus subtilis, Bacillus thuringiensis, Bacillus stearothermophilus* and *Bacillus cereus;*
Enterobacteriaceae, such as
  *Escherichia coli,*
  Enterobacter (e.g. *Enterobacter aerogenes, Enterobacter agglomerans* and *Enterobacter cloacae*)
  Citrobacter (such as *Citrob. freundii* and *Citrob. divernis*),
  Hafnia (e.g. *Hafnia alvei*),
  Erwinia (e.g. *Erwinia persicinus*),
  Morganella morganii,
  Salmonella (*Salmonella enterica* and *Salmonella typhi*),
  Shigella (e.g. *Shigella dysenteriae, Shigella flexneri, Shigella boydii* and *Shigella sonnei*),
  Klebsiella (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*),
  Proteus (e.g. *Pr. mirabilis, Pr. rettgeri* and *Pr. vulgaris*),
  Providencia (e.g. *Providencia alcalifaciens, Providencia rettgeri* and *Providencia stuartii*),
  Serratia (e.g. *Serratia marcescens* and *Serratia liquifaciens*), and
  Yersinia (e.g. *Yersinia enterocolitica, Yersinia pestis* and *Yersinia pseudotuberculosis*);
Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);
Helicobacter (e.g. *Helicobacter pylori, Helicobacter cinaedi* and *Helicobacter fennelliae*);
Acinetobacter (e.g. *A. baumanii, A. calcoaceticus, A. haemolyticus, A. johnsonii, A. junii, A. Iwoffi* and *A. radioresistens*);
Pseudomonas (e.g. *Ps. aeniginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*);
Bacteriodes fragilis;
Peptococcus (e.g. *Peptococcus niger*);
Peptostreptococcus;
Clostridium (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C.septicum, C. sordelii, C. sphenoides, C. sporogenes, C. subterminale, C. symbiosum* and *C. tertium*);
Mycoplasma (e.g. *M. pneumoniae, M. hominis, M. genitalium* and *M. urealyticum*);
Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celaturn, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacte-* rium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi and Mycobacterium xenopi);

Haemophilus (e.g. Haemophilus influenzae, Haemophilus ducreyi, Haemophilus aegyptius, Haemophilus parainfluenzae, Haemophilus haemolyticus and Haemophilus parahaemolyticus);

Actinobacillus (e.g. Actinobacillus actinomycetemcomitans, Actinobacillus equuli, Actinobacillus hominis, Actinobacillus lignieresii, Actinobacillus suis and Actinobacillus ureae);

Actinomyces (e.g. Actinomyces israelii);

Propionibacteria (e.g. Propionibacterium acnes);

Brucella (e.g. Brucella abortus, Brucella canis, Brucella melintensis and Brucella suis);

Campylobacter (e.g. Campylobacter jejuni, Campylobacter coli, Campylobacter lari and Campylobacter fetus);

Listeria monocytogenes;

Vibrio (e.g. Vibrio cholerae and Vibrio parahaemolyticus, Vibrio alginolyticus, Vibrio carchariae, Vibrio fluvialis, Vibrio fumissii, Vibrio hollisae, Vibrio metschnikovii, Vibrio mimicus and Vibrio vulnificus);

Erysipelothrix rhusopathiae;

Corynebacteriaceae (e.g. Corynebacterium diphtheriae, Corynebacterium jeikeium and Corynebacterium urealyticum);

Spirochaetaceae, such as Borrelia (e.g. Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae and Borrelia venezuelensis) and Treponema (Treponema pallidum ssp. pallidum, Treponema pallidum ssp. endemicum, Treponema pallidum ssp. pertenue and Treponema carateum);

Pasteurella (e.g. Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica and Pasteurella stomatis);

Bordetella (e.g. Bordetella bronchiseptica, Bordetella hinzii, Bordetella holmsefi, Bordetella parapertussis, Bordetella pertussis and Bordetella trematum);

Nocardiaceae, such as Nocardia (e.g. Nocardia asteroides and Nocardia brasiliensis);

Rickettsia (e.g. Ricksettsii or Coxiella bumetii);

Legionella (e.g. Legionalla anisa, Legionalla birminghamensis, Legionalla bozemanii, Legionalla cincinnatiensis, Legionalla dumoffli, Legionalla feelefi, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis and Legionalla wadsworthii);

Moraxella catarrhalis;

Stenotrophomonas maltophifia;

Burkholderia cepacia;

Francisella tularensis;

Gardnerella (e.g. Gardneralla vaginalis and Gardnerella mobiluncus);

Streptobacillus moniliformis;

Flavobacteriaceae, such as Capnocytophaga (e.g. Capnocytophaga canimorsus, Capnocytophaga cynodegmi, Capnocytophaga gingivalis, Capnocytophaga granulosa, Capnocytophaga haemolytica, Capnocytophaga ochracea and Capnocytophaga sputigena);

Bartonella (Bartonella bacilliformis, Bartonella clarridgeiae, Bartonella elizabethae, Bartonella henselae, Bartonella quintana and Bartonella vinsonii arupensis);

Leptospira (e.g. Leptospira biflexa, Leptospira borgpetersenii, Leptospira inadai, Leptospira interrogans, Leptospira kirschneri, Leptospira noguchii, Leptospira santarosai and Leptospira weilii);

Spirillium (e.g. Spirillum minus);

Bacteroides (e.g. Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus and Bacteroides vulgatus);

Prevotella (e.g. Prevotella bivia, Prevotella buccae, Prevotella corporis, Prevotella dentalis (Mitsuokella dentalis), Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis and Prevotella zoogleoformans);

Porphyromonas (e.g. Porphyromonas asaccharolytica, Porphyromonas cangingivalis, Porphyromonas canons, Porphyromonas cansulci, Porphyromonas catoniae, Porphyromonas circumdentaria, Porphyromonas crevioncanis, Porphyromonas endodontalis, Porphyromonas gingivalis, Porphyromonas gingivicanis, Porphyromonas levii and Porphyromonas macacae);

Fusobacterium (e.g. F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans and F. varium);

Chlamydia (e.g. Chlamydia trachomatis);

Chlamydophila (e.g. Chlamydophila abortus (Chlamydia psittaci), Chlamydophila pneumoniae (Chlamydia pneumoniae) and Chlamydophila psittaci (Chlamydia psittaci));

Leuconostoc (e.g. Leuconostoc citreum, Leuconostoc cremoris, Leuconostoc dextranicum, Leuconostoc lactis, Leuconostoc mesenteroides and Leuconostoc pseudomesenteroides);

Gemella (e.g. Gemella bergeri, Gemella haemolysans, Gemella morbillorum and Gemella sanguinis); and Ureaplasma (e.g. Ureaplasma parvum and Ureaplasma urealyticum).

In one embodiment of the invention, the term "bacteria" includes references to any of the above classes or specific types of organisms, except for Shigella (e.g. Shigella flexneri) or Salmonella (e.g. Salmonella typhi).

When used herein, the terms "fungi" (and derivatives thereof, such as "fungal infection") includes references to organisms (or infections due to organisms) of the following classes and specific types:

*Absidia* (e.g. *Absidia corymbifera*);
*Ajellomyces* (e.g. *Ajellomyces capsulatus* and *Ajellomyces dermatitidis*);
*Arthroderma* (e.g. *Arthroderma benhamiae*, *Arthroderma fulvum*, *Arthroderma gypseum*, *Arthroderma incurvatum*, *Arthroderma otae* and *Arthroderma vanbreuseghemii*);
*Aspergillus* (e.g. *Aspergillus flavus*, *Aspergillus fumigatus*, *Aspergillus niger* and *Aspergillus terreus*);
*Blastomyces* (e.g. *Blastomyces dermatitidis*);
*Candida* (e.g. *Candida albicans*, *Candida glabrata*, *Candida guilliermondii*, *Candida krusei*, *Candida parapsilosis*, *Candida tropicalis*, *Candida pelliculosa* and *Candida lusitaniae*);
*Cladophialophora* (e.g. *Cladophialophora carrionii*);
*Coccidioides* (e.g. *Coccidioides immitis*);
*Cryptococcus* (e.g. *Cryptococcus neoformans*);
*Cunninghamella* (e.g. *Cunninghamella* sp.)
*Epidermophyton* (e.g. *Epidermophyton floccosum*);
*Exophiala* (e.g. *Exophiala dermatitidis*);
*Filobasidiella* (e.g. *Filobasidiella neoformans*);
*Fonsecaea* (e.g. *Fonsecaea pedrosoi*);
*Fusarium* (e.g. *Fusarium solani* and *Fusarium oxysporum*);
*Geotrichum* (e.g. *Geotrichum candidum*);
*Histoplasma* (e.g. *Histoplasma capsulatum*);
*Hortaea* (e.g. *Hortaea werneckii*);
*Issatchenkia* (e.g. *Issatchenkia orientalis*);
*Madurella* (e.g. *Madurella grisae*);
*Malassezia* (otherwise known as *Pityrosporum*) (e.g. *Malassezia furfur*, *Malassezia globosa*, *Malassezia obtusa*, *Malassezia pachydermatis*, *Malassezia restricta*, *Malassezia slooffiae*, *Malassezia sympodialis*, *Malassezia dermatis*, *Malassezia nana* and *Malassezia yamatoensis*);
*Microsporum* (e.g. *Microsporum canis*, *Microsporum fulvum*, *Microsporum gypseum*, *Microsporum audouinii* and *Microsporum ferrugineum*);
*Mucor* (e.g. *Mucor circinelloides*);
*Nectria* (e.g. *Nectria haematococca*);
*Paecilomyces* (e.g. *Paecilomyces variotii*);
*Paracoccidioides* (e.g. *Paracoccidioides brasiliensis*);
*Penicillium* (e.g. *Penicillium mameffei*);
*Pichia* (e.g. *Pichia anomala* and *Pichia guilliermondii*);
*Pneumocystis* (e.g. *Pneumocystis jiroveci* (*Pneumocystis carinii*));
*Pseudallescheria* (e.g. *Pseudallescheria boydii*);
*Rhizopus* (e.g. *Rhizopus oryzae* and *Rhizopus oligosporus*);
*Rhodotorula* (e.g. *Rhodotorula rubra*);
*Scedosporium* (e.g. *Scedosporium apiospermum*);
*Schizophyllum* (e.g. *Schizophyllum commune*);
*Sporothrix* (e.g. *Sporothrix schenckii*);
*Trichophyton* (e.g. *Trichophyton mentagrophytes*, *Trichophyton rubrum*, *Trichophyton verrucosum*, *Trichophyton violaceum*, *Trichophyton schoenleinii*, *Trichophyton tonsurans*, *Trichophyton concentricum*, *Trichophyton gourvilii*, *Trichophyton interdigitale*, *Trichophyton megninii*, *Trichophyton soudanense*); and
*Trichosporon* (e.g. *Trichosporon asahii*, *Trichosporon cutaneum*, *Trichosporon inkin* and *Trichosporon mucoides*).

Thus, compounds of formula I, or combination products comprising compounds of formula I, may be used to kill any of the above-mentioned bacterial or fungal organisms (clinically latent or otherwise).

Particular bacteria that may be mentioned in this respect include:
(i) Staphylococci, such as *Staph. aureus* (either Methicillin-sensitive (i.e. MSSA) or Methicillin-resistant (i.e. MRSA)), *Staph. epidermidis*, *Staphylococcus haemolyticus*, *Staphylococcus hominis* and *Staphylococcus lugdunensis*);
(ii) Streptococci, such as *Strept. agalactiae*, *Strept. pyogenes*; *Strept. pneumoniae*, and *Strept.* Group C);
(iii) Bacillaceae, such as *Bacillus anthracis* or, particularly, *Bacillus cereus*;
(iv) Enterobacteriaceae, such as *Escherichia coli*, Klebsiella (e.g. *Klebs. pneumoniae* and *Klebs. oxytoca*) and Proteus (e.g. *Pr. mirabilis*, *Pr. rettgeri* and *Pr. vulgaris*);
(v) *Haemophilus influenzae*;
(vi) Enterococci, such as *Enterococcus faecalis*, *Enterococcus faecium*, *Enterococcus gallinarum* and *Enterococcus casseliflavus*;
(vii) Mycobacteria, such as *Mycobacterium tuberculosis*;
(viii) Propionibacteria, such as *Propionibacterium acnes*;
(ix) Corynebacteriaceae such as *Corynebacterium jeikeium*;
(x) *Stenotrophomonas maltophilia*; and
(xi) Mycoplasma such as *M. pneumoniae*.

Certain bacteria that may be mentioned include those at (i), (ii) and (viii) above.

Particular fungi that may also be mentioned in this respect include:
(I) *Aspergillus* (e.g. *Aspergillus fumigatus*; *Aspergillus niger*, *Aspergillus flavus* or *Aspergillus terreus*);
(II) *Candida* (e.g. *Candida albicans*, *Candida tropicalis*, *Candida parapsilosis*, *Candida glabrata* or *Candida lusitaniae*);
(III) *Cryptococcus neoformans*;
(IV) *Histoplasma capsulatum*;
(V) *Pneumocystis jiroveci*;
(VI) *Issatchenkia orientalis*;
(VII) *Rhizopus oligosporus*;
(VIII) *Fusarium oxysporum*;
(IX) *Microsporum* (e.g. *Microsporum audouinii*, *Microsporum ferrugineum* or *Microsporum canis*);
(X) *Epidermophyton floccosum*;
(XI) *Malassezia* (e.g. *Malassezia furfur*); and
(XII) *Trichophyton* (e.g. *Trichophyton mentagrophytes*, *Trichophyton rubrum*, *Trichophyton verrucosum*, *Trichophyton violaceum*, *Trichophyton schoenleinii*, *Trichophyton tonsurans*, *Trichophyton concentricum*, *Trichophyton gourvilii*, *Trichophyton interdigitale*, *Trichophyton megninii*, *Trichophyton soudanense* (such as *Trichophyton violaceum*, *Trichophyton mentagrophytes* or, particularly, *Trichophyton rubrum*)).

Certain fungi that may be mentioned include those at (I), (II), (X), (XI) and (XII) above.

Particular bacterial or fungal infections that may be mentioned in relation to
(i) the use according to the first or fourth aspect of the invention,
(ii) the method according to the second or sixth aspect of the invention,
(iii) the compound for use according to the second or seventh aspect of the invention, and
(iii) the above-described uses, methods or combination products for use involving the combination product according to the eighth aspect of the invention (i.e. uses (i) or (iv) above, method (ii) or (v) above or combination product for use (iii) or (vi) above), include infections with Staph. aureus (either Methicillin-sensitive (i.e. MSSA) or Methicillin-resistant (i.e. MRSA)) and Staph. epidermidis, Streptococci, such as Strept. agalactiae and Strept. pyogenes, Bacillaceae, such as Bacillus anthracis or, particularly, Bacillus cereus, Enterobacteriaceae, such as Escherichia coli, Klebsiella (e.g. Klebs. pneumoniae and Klebs. oxytoca) and Proteus (e.g. Pr. mirabilis, Pr. rettgeri and Pr. vulgaris), Haemophilus influenzae, Enterococci, such as Enterococcus faecalis and Enterococcus faecium, Mycobacteria, such as Mycobacterium tuberculosis, Propionibacteria, such as Propionibacterium acnes or fungi such as Aspergillus fumigatus, Candida albicans, Cryptococcus neoformans, Histoplasma capsulatum, Pneumocystis jiroveci, Epidermophyton floccosum, Malassezia (e.g. Malassezia furfur) or, particularly, Trichophyton (e.g. Trichophyton violaceum, Trichophyton mentagrophytes or, particularly, Trichophyton rubrum).

In this respect, particular conditions that the compounds of formula I, or combination products comprising compounds of formula I, can be used to treat include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, acne rosacea, rosacea (including erythematotelangiectatic rosacea, papulopustular rosacea, phymatous rosacea and ocular rosacea), actinomycosis, bacilliary dysentry, bacterial conjunctivitis, bacterial keratitis, botulism, Buruli ulcer, bone and joint infections, bronchitis (acute or chronic), brucellosis, burn wounds, cat scratch fever, cellulitis, folliculitis (including hot tub folliculitis), chancroid, cholangitis, cholecystitis, cutaneous diphtheria, cystic fibrosis, cystitis, diffuse pan-bronchiolitis, diphtheria, dental caries, diseases of the upper respiratory tract, empyema, endocarditis, endometritis, enteric fever, enteritis, epididymitis, epiglottitis, erysipelas, erysipeloid, erythrasma, eethyma, eethyma gangrenosum, eye infections, furuncles, Gardnerella vaginitis, gastrointestinal infections (gastroenteritis), genital infections, gingivitis, gonorrhoea, granuloma inguinale, Haverhill fever, atopic eczma with staphylococcal carriage, infected eczma, infected burns, infected abrasions, infected skin wounds, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), furunculosis, carbunculosis, staphylococcal scalded skin syndrome, surgical scarlet fever, streptococcal peri-anal disease, streptococcal toxic shock syndrome, pitted keratolysis, trichomycosis axillaris, external canal ear infections, green nail syndrome, spirochetes, necrotizing fasciitis, Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous M. kansasii, M. malmoense, M. szulgai, M. simiae, M. gordonae, M. haemophilum, M. avium, M. intracellulare, M. chelonae (including M. abscessus) or M. fortuitum infections, swimming pool (or fish tank) granuloma, lymphadenitis and Buruli ulcer (Baimsdale ulcer, Searles' ulcer, Kakerifu ulcer or Toro ulcer)), Q fever, rat-bite fever, reticulosis, Ritter's disease, salmonellosis, salpingitis, septic arthritis, septic infections, septicemia, sinusitis, skin infections (e.g. skin granulomas), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis.

Further conditions that may be mentioned in this respect include infections with MSSA, MRSA, Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilus influenzae, Enterococcus faecalis or Enterococcus faecium.

Specific compounds of formula I that may be mentioned in relation to the above-described aspects of the invention include compounds of Examples 1 to 43 (e.g. 1 to 39) below.

The use of certain compounds of formula I in medicine, including compounds of formula I (and Ia), as hereinbefore defined, is, to the knowledge of the inventors, novel.

For the avoidance of doubt, references herein to compounds of formula I include references to all embodiments described above in relation to compounds of formulae I and Ia.

In this respect, a further aspect of the invention provides a compound of formula Ib for use in medicine, wherein compounds of formula Ib take the same definition as compounds of formula I, as hereinbefore defined, except that:

$R^{4a}$ represents (a) $C_{1-12}$ alkyl, $C_{3-12}$ cycloalkyl, $C_{3-12}$ cycloalkenyl (which latter three groups are substituted an aryl or $Het^1$ group and are optionally further substituted by one or more substituents selected from halo, nitro, CN, $C_{1-6}$ alkyl, $C_{2-6}$ alkenyl, $C_{2-6}$ alkynyl, $C_{3-8}$ cycloalkyl (which latter three groups are optionally substituted by one or more substituents selected from OH, =O, halo, $C_{1-4}$ alkyl and $C_{1-4}$ alkoxy), $OR^{5a}$, $S(O)_nR^{5b}$, $S(O)_2N(R^{5c})(R^{5d})$, $N(R^{5e})S(O)_2R^{5f}$, $N(R^{5g})(R^{5h})$, $B^1—C(O)—B^2—R^{5i}$, aryl and $Het^1$, and which $C_{3-12}$ cycloalkyl or $C_{4-12}$ cycloalkenyl groups may additionally be substituted by =O), (c) aryl or (d) $Het^2$, and provided that:

(a) when E represents CH, then $R^3$ does not represent one or more (e.g. one or two) substituents that include one $OR^{8a}$ substituent in the 7-position of the quinoline ring system; and (b) when E represents N and $R^2$ represents H, then $R^1$ does not represent an $—O—R^{4a}$ substituent at the 3-position of the pyrrolidine ring, in which $R^{4a}$ represents aryl or $Het^2$.

Compounds of formula Ib that may be mentioned include those in which:

(i) $R^3$ does not represent one or more (e.g. one or two) substituents that include one $OR^{8a}$ substituent in the 7-position of the quinoline ring system;

(ii) $R^1$ does not (e.g. when $R^2$ represents H) represent an —O—$R^{4a}$ substituent at the 3-position of the pyrrolidine ring (e.g. an —O—$R^{4a}$ substituent in which $R^{4a}$ represents aryl or $Het^2$);

(iii) $R^2$ does not represent aryl or $Het^4$ when E represents N; and/or (iv) $R^1$ does not represent piperazin-1-yl.

The use of compounds of formula Ib in medicine includes their use as pharmaceuticals. The invention therefore further provides for the use of a compound of formula Ib as a pharmaceutical.

Compounds of formula Ib are, to the knowledge of the inventors, novel per se. Thus, in a still further aspect of the invention, there is provided a compound of formula Ib.

When used herein, the term "compounds of Examples 1 to 43 below" refers to the title compounds of those examples, namely:

(1) 6-chloro-2-methyl-4-(3-phenylpyrrolidin-1-yl)quinoline;
(2) 6-benzyloxy-2-methyl-4-(3-phenylpyrrolidin-1-yl) quinoline;
(3) 2-methyl-4-(3-phenylpyrrolidin-1-yl)-6-(pyridin-3-ylmethoxy)quinoline;
(4) 6-(4-methanesulfonylbenzyloxy)-2-methyl-4-(3-phenylpyrrolidin-1-yl)quinoline;
(5) 6-(4-methoxybenzyloxy)-2-methyl-4-(3-phenylpyrrolidin-1-yl)quinoline
(6) 2-methyl-6-phenethyloxy-4-(3-phenylpyrrolidin-1-yl) quinoline;
(7) 2-methyl-6-(5-methylisoxazol-3-ylmethoxy)-4-(3-phenylpyrrolidin-1-yl)quinoline;
(8) 4-(3-benzylpyrrolidin-1-yl)-2-methyl-6-phenoxyquinoline;
(9) 4-[3-(4-methoxyphenyl)pyrrolidin-1-yl]-2-methyl-6-phenoxyquinoline;
(10) 4-[3-(4-chlorophenyl)pyrrolidin-1-yl]-2-methyl-6-phenoxyquinoline;
(11) [1-(2-methyl-6-phenoxyquinolin-4-yl)-pyrrolidin-3-yl] phenylamine;
(12) N[2-methyl-4-(3-phenylpyrrolidin-1-yl)quinolin-6-yl]benzamide;
(13) N-[2-methyl-4-(3-phenylpyrrolidin-1-yl)-quinolin-6-yl]-2-phenylacetamide;
(14) 4-chloro-N-[2-methyl-4-(3-phenylpyrrolidin-1-yl) quinolin-6-yl]benzamide;
(15) 4-methoxy-N-[2-methyl-4-(3-phenylpyrrolidin-1-yl) quinolin-6-yl]benzamide;
(16) 2-methyl-N-[2-methyl-4-(3-phenylpyrrolidin-1-yl) quinolin-6-yl]benzamide;
(17) pyrazine-2-carboxylic acid [2-methyl-4-(3-phenylpyrrolidin-1-yl)quinolin-6-yl]amide;
(18) 1H-pyrazole-4-carboxylic acid [2-methyl-4-(3-phenylpyrrolidin-1-yl)quinolin-6-yl]amide;
(19) furan-2-carboxylic acid [2-methyl-4-(3-phenylpyrrolidin-1-yl)quinolin-6-yl]amide;
(20) N-[2-methyl-4-(3-phenylpyrrolidin-1-yl)quinolin-6-yl] nicotinamide;
(21) 3-methyl-3H-imidazole-4-carboxylic acid [2-methyl-4-(3-phenylpyrrolidin-1-yl)quinolin-6-yl]amide;
(22) 5-methyl-1H-pyrazole-3-carboxylic acid [2-methyl-4-(3-phenylpyrrolidin-1-yl)-quinolin-6-yl]amide;
(23) pyridazine-4-carboxylic acid [2-methyl-4-(3-phenylpyrrolidin-1-yl)-quinolin-6-yl]amide;
(24) 2-(4-methoxyphenyl)-N-[2-methyl-4-(3-phenylpyrrolidin-1-yl)quinolin-6-yl]acetamide;
(25) 2-(4-chlorophenyl)-N-[2-methyl-4-(3-phenylpyrrolidin-1-yl)quinolin-6-yl]acetamide;
(26) 3,5-dimethyl-isoxazole-4-carboxylic acid [2-methyl-4-(3-phenylpyrrolidin-1-yl)quinolin-6-yl]amide;
(27) 2-(3-methyl-isoxazol-5-yl)-N-[2-methyl-4-(3-phenyl-pyrrolidin-1-yl)-quinolin-6-yl]-acetamide;
(28) N-[2-methyl-4-(3-phenylpyrrolidin-1-yl)quinolin-6-yl] benzenesulfonamide;
(29) benzyl-[2-methyl-4-(3-phenylpyrrolidin-1-yl)quinolin-6-yl]amine;
(30) (R- or S-)Benzyl-[2-methyl-4-(3-phenylpyrrolidin-1-yl) quinolin-6-yl]amine;
(31) (S- or R-)Benzyl-[2-methyl-4-(3-phenylpyrrolidin-1-yl) quinolin-6-yl]amine;
(32) (4-methoxybenzyl)-[2-methyl-4-(3-phenylpyrrolidin-1-yl)quinolin-6-yl]amine;
(33) 4-{[2-methyl-4-(3-phenylpyrrolidin-1-yl)quinolin-6-ylamino]methyl}benzonitrile;
(34) 1-[2-methyl-4-(3-phenylpyrrolidin-1-yl)quinolin-6-yl] pyrrolidin-2-one;
(35) N[2-methyl-4-(3-phenylpyrrolidin-1-yl)quinolin-6-yl]-3-phenyl propionamide;
(36) 5-methyl-isoxazole-3-carboxylic acid [2-methyl-4-(3-phenylpyrrolidin-1-yl)-quinolin-6-yl]amide;
(37) pyridine-2-carboxylic acid [2-methyl-4-(3-phenylpyrrolidin-1-yl)quinolin-6-yl]amide;
(38) N-[4-(3-benzylpyrrolidin-1-yl)-2-methylquinolin-6-yl] benzamide;
(39) 2-methyl-6-phenoxy-4-(3-phenylpyrrolidin-1-yl)quinoline;
(40(a)) 4-((R or S)-3-benzylpyrrolidin-1-yl)-2-methyl-6-phenoxyquinoline;
(40(b)) 4-((S or R)-3-benzylpyrrolidin-1-yl)-2-methyl-6-phenoxyquinoline;
(41(a)) 4-[(R or S)-3-(4-methoxyphenyl)pyrrolidin-1-yl]-2-methyl-6-phenoxy-quinoline;
(41(b)) 4-[(S or R)-3-(4-methoxyphenyl)pyrrolidin-1-yl]-2-methyl-6-phenoxy-quinoline;
(42(a)) 5-methyl-1H-pyrazole-3-carboxylic acid [2-methyl-4-((R or S)-3-phenyl-pyrrolidin-1-yl)-quinolin-6-yl] amide;
(42(b)) 5-methyl-1H-pyrazole-3-carboxylic acid [2-methyl-4-((S or R)-3-phenyl-pyrrolidin-1-yl)-quinolin-6-yl] amide;
(43(a)) N-[4-((R or S)-3-benzylpyrrolidin-1-yl)-2-methylquinolin-6-yl]benzamide;
(43(b)) N-[4-((S or R)-3-benzylpyrrolidin-1-yl)-2-methylquinolin-6-yl]benzamide,
and pharmaceutically-acceptable salts and/or solvates thereof.

As well as having activity against fungi and bacteria, compounds of formula I (e.g. compounds of formula Ia or Ib) may also have activity against other organisms, such as protozoa. Therefore, according to further aspects of the invention, there is provided:

(i) the use of a compound of formula I, Ia or Ib, as hereinbefore defined, for the preparation of a medicament for the treatment or prevention of a protozoal disease;
(ii) a method of treating or preventing a protozoal disease in a mammal, the method comprising administering to said mammal an effective amount of a compound of formula I, Ia or Ib, as hereinbefore defined;
(iii) a compound of formula I, Ia or Ib for use in the treatment or prevention of a protozoal disease;
(iv) use (e.g. ex vivo use) of a compound of formula I, Ia or Ib for killing protozoa.

In these aspects of the invention, the compound of formula I, Ia or Ib may be one in which $R^2$ does not represent $Het^4$ (e.g. pyrrolidin-1-yl) when E represents N.

When used to treat or prevent a protozoal disease, the compounds of formula I, Ia or Ib may be formulated as described below (i.e. included in a pharmaceutical formulation or a topical pharmaceutical composition comprising a compound of formula I, Ia or Ib in admixture with a pharmaceutically acceptable adjuvant, diluent or carrier).

When used herein, the terms "protozoa" (and derivatives thereof, such as "protozoal disease") includes references to organisms (or infections due to organisms) of the following classes and specific types:
Leishmania (e.g. *Leishmania donovanii*);
Plasmodium spp.;
Trypanosoma spp.;
Giardia lamblia;
coccidia (e.g. *Cryptosporidium parvum*, *Isospora belli*);
Toxoplasma (e.g. *Toxoplasma gondii*);
Balantidium coli;
amoeba (e.g. *Entamoeba*, such as *Entamoeba histolytica*, *Entamoeba coli*, *Entamoeba hartmanni* and *Entamoeba polecki*); and
Microsporidia (e.g. *Enterocylozoon bieneusi*, *Encephalitozoon hellem*, *Encephalitozoon cuniculi* and *Septata intestinalis*).

Particular conditions that the compounds of formula I, Ia or Ib can be used to treat include Leishmaniasis, malaria, trypanosomiasis, toxoplasmosis, giardiasis, balantidiasis, amoebiasis (amoebic dysentery), cryptosporidiosis, isosporiasis and microsporidiosis.

Compounds of formula I (including compounds of formulae Ia and Ib) may be prepared in accordance with techniques known to those skilled in the art, for example as described hereinafter.

Thus, according to a further aspect of the invention there is provided a process for the preparation of a compound of formula I (e.g. a compound of formula Ia or Ib), which comprises:

(a) reaction of a compound of formula II,

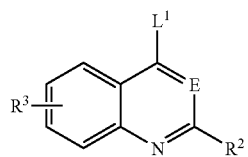

wherein $L^1$ represents a suitable leaving group (e.g. halo, such as chloro), and E, $R^2$ and $R^3$ are as hereinbefore defined, with a compound of formula III,

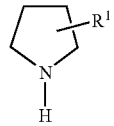

wherein $R^1$ is as hereinbefore defined, for example under conditions known to those skilled in the art, such as by reaction at elevated temperature (i.e. from 70 to 250° C., for example as achieved through microwave heating), and optionally at elevated pressure (i.e. above 1 atmosphere), in the presence of a suitable organic solvent, such as a $C_{2-4}$ alkylene glycol (e.g. ethylene glycol) or a mono- or di-$C_{1-4}$ alkyl ether of a $C_{2-4}$ alkylene glycol (e.g. ethoxyethanol), and optionally in the presence of an appropriate base (for instance, the compound of formula II may be reacted with between 1 and 3 equivalents (e.g. from 2 to 2.5 equivalents) of the compound of formula III at elevated temperature (e.g. above 180° C., such as from 200 to 240° C.), wherein the reaction mixture is optionally heated by use of microwaves, in the presence of a suitable high-boiling solvent (e.g. ethoxyethanol));

(b) for compounds of formula I in which E represents CH, reaction of a compound of formula IV,

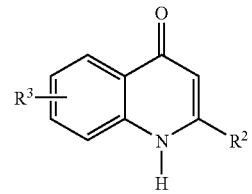

wherein $R^2$ and $R^3$ are as hereinbefore defined, with a compound of formula III, as hereinbefore defined, for example under conditions known to those skilled in the art, such as at ambient or elevated temperature (e.g. 40 to 200° C.) in the presence of a silylating agent (e.g. hexamethyldisilazane) and optionally in the presence of an appropriate catalyst (e.g. an ammonium salt such as ammonium sulfate);

(c) for compounds of formula I in which $R^3$ represents or includes a —N(H)C(O)$R^{8i}$ substituent, coupling of a corresponding compound of formula I in which $R^3$ represents or includes a —NH$_2$ substituent with a compound of formula V, $$R^{8i}C(O)L^2 \qquad V$$

wherein $L^2$ represents a leaving group (such as OH, halo (such as chloro or bromo) or —OC(O)$R^{8i}$) and $R^{8i}$ is as hereinbefore defined, for example under conditions known to those skilled in the art (such as: (i) when $L^2$ represents OH, in the presence of a coupling agent (e.g. oxalyl chloride in DMF; EDC; DCC; HBTU; HATU; PyBOP; or TBTU, which latter six agents can optionally be employed in conjunction with a catalyst such as HOBt, HOAt or HOSu), an appropriate base (e.g. pyridine, DMAP, TEA, 2,4,6-collidine or DIPEA) and a suitable organic solvent (e.g. DCM, MeCN, EtOAc or DMF); or (ii) when $L^2$ represents halo or OC(O)$R^{8i}$, in the presence of an appropriate base (e.g. pyridine, DMAP, TEA, 2,4,6-collidine or DIPEA) and a suitable organic solvent (e.g. DCM, MeCN, EtOAc or DMF));

(d) for compounds of formula I in which $R^3$ represents or includes a —N(H)S(O)$_2R^{8f}$ substituent, coupling of a corresponding compound of formula I in which $R^3$ represents or includes a —NH$_2$ substituent with a compound of formula VI, $$R^{8f}S(O)_2L^3 \qquad VI$$

wherein $L^3$ represents a leaving group (e.g. halo (such as chloro) or OS(O)$_2R^{8f}$) and $R^{8f}$ is as hereinbefore defined, for example under conditions known to those skilled in the art, such as in the presence of a suitable solvent (e.g. DCM) and an appropriate base (e.g. pyridine);

(e) for compounds of formula I in which $R^3$ represents or includes a —N(H)$R^{8h}$ substituent, wherein $R^{8h}$ is optionally substituted $C_{1-10}$ alkyl, reaction of a corresponding compound of formula I in which $R^3$ represents or includes a —$NH_2$ substituent with a compound of formula VII, $$R^{8h1}CHO \qquad \text{VII}$$

wherein $R^{8h1}$ represents H or $C_{1-9}$ alkyl, which latter group is optionally substituted as defined above in respect of $R^{8h}$, in the presence of a suitable reducing agent (e.g. sodium cyanoborohydride or sodium triacetoxyborohydride), for example under conditions known to those skilled in the art, such as at ambient temperature in the presence of a catalytic quantity of a carboxylic acid (e.g. a $C_{2-4}$ alkanoic acid, such as acetic acid) and an appropriate solvent (e.g. 1,2-dichloroethane);

(f) for compounds of formula I in which $R^3$ represents or includes an —$OR^{8a}$ substituent, wherein $R^{8a}$ is optionally substituted $C_{1-10}$ alkyl, coupling of a corresponding compound of formula I in which $R^3$ represents or includes an —OH substituent with a compound of formula VIII, $$R^{8a1}L^3 \qquad \text{VIII}$$

wherein $R^{8a1}$ represents a $C_{1-10}$ alkyl group that is optionally substituted as defined above in respect of $R^{8a}$ and $L^3$ is as hereinbefore defined, for example under conditions known to those skilled in the art, such as at ambient or elevated temperature (e.g. 120° C.), wherein the reaction mixture is optionally heated by use of microwaves, in the presence of a base (e.g. an alkali metal hydride, such as sodium hydride, or an alkali metal carbonate, such as caesium carbonate) and a suitable solvent (e.g. DMF); or (g) for compounds of formula I in which $R^1$ represents —N(H)—$R^{4a}$, wherein $R^{4a}$ represents aryl, reaction of a compound of formula IX,

IX wherein E, $R^2$ and $R^3$ are as hereinbefore defined, with a compound of formula X, $$R^{4a1}L^3 \qquad \text{X}$$

wherein $R^{4a1}$ represents aryl, and $L^3$ and aryl are as hereinbefore defined, in the presence of a palladium cross-coupling catalyst (e.g. tris-(dibenzylideneacetone)-dipalladium), for example under conditions known to those skilled in the art, such as at elevated temperature (e.g. 150° C.), wherein the reaction mixture is optionally heated by use of microwaves, in the presence of a suitable phosphine (e.g. 2-dicyclohexyl-phosphino-2'-dimethylaminobiphenyl), an appropriate base (e.g. sodium tert-butoxide) and an organic solvent (e.g. toluene).

Compounds of formula II in which $L^1$ represents halo may be prepared by reacting a corresponding compound of formula IV, as hereinbefore defined, with a suitable halogenating reagent (e.g. phosphorous oxychloride), for example under conditions known to those skilled in the art, such as at ambient or elevated temperature (e.g. 100 to 120° C.), optionally in the presence of a suitable organic solvent (e.g. toluene or xylene).

Compounds of formula II in which $R^3$ represents a —$NH_2$ substituent may be prepared by reduction of a corresponding compound of formula II in which $R^3$ represents a —$NO_2$ substituent, for example by catalytic hydrogenation in the presence of a suitable catalyst (such as Pd/C, $Pt_2O$ or Raney nickel) under conditions known to those skilled in the art, such as at ambient temperature in the presence of a suitable organic solvent (e.g. ethanol).

Compounds of formula II in which $R^3$ represents a —$NO_2$ substituent may be prepared according to or by analogy with procedures known to those skilled in the art (e.g. those described in *J. Chem. Soc.* 1367 (1949)), such as by reaction of a corresponding compound of formula II in which $R^3$ represents H with a suitable nitrating agent (e.g. a mixture of nitric and sulfuric acids), for example under conditions known to those skilled in the art, such as at ambient or elevated temperature (e.g. 50 to 75° C.).

Compounds of formula III in which $R^1$ is a single substituent at the 3-position of the pyrrolidine ring may be prepared by methods known to those skilled in the art (e.g. according to or by analogy with relevant methods disclosed in: *J. Org. Chem.* 55, 270 (1990); *Synthesis* 1023 (1991); *J. Am. Chem. Soc.* 124 (2002); *J. Org. Chem.* 64, 4273 (1999); *Synlett* 2092 (2002); *Med. Chem. Res.* 7, 76 (1997); or *J. Org. Chem.* 60, 4743 (1995)), or by one of the following methods.

(i) Reduction of a corresponding compound of formula XI,

XI wherein $R^1$ is as hereinbefore defined, in the presence of a suitable reducing agent (e.g. lithium aluminium hydride), for example under conditions known to those skilled in the art, such as at ambient or elevated temperature (e.g. 50 to 75° C.) in the presence of a suitable organic solvent (e.g. tetrahydrofuran).

(ii) Reaction of a corresponding compound of formula XII,

XII wherein $L^3$ and $R^1$ are as hereinbefore defined, with ammonia or a compound of formula XIII, $$R^a\text{—}NH_2 \qquad \text{XIII}$$

wherein $R^a$ represents an appropriate protective group (e.g. —$CH_2Ph$ or —OH), for example under conditions known to those skilled in the art, such as at ambient or elevated temperature (e.g. 50 to 65° C.) in the presence of a suitable organic solvent (e.g. tetrahydrofuran) and an appropriate base (e.g. Hunig's base or 4-dimethylaminopyridine), followed (if necessary) by removal of the protective group $R^a$ under conditions known by those skilled in the art (e.g. by catalytic hydrogenation using Pd/C as the catalyst, for example at ambient or elevated temperature (e.g. 50 to 65° C.) in the presence of a suitable organic solvent, such as ethanol or methanol).

Compounds of formula IV may be prepared by reacting a compound of formula XIV,

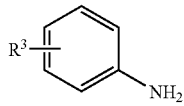

XIV wherein $R^3$ is as hereinbefore defined with a compound of formula XV,

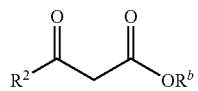

XV wherein $R^b$ is $C_{1-4}$ alkyl (such as ethyl), in the presence of an acid (e.g. polyphosphoric acid), for example under conditions known to those skilled in the art, such as at ambient or elevated temperature (e.g. 90 to 105° C.), in the presence of a suitable organic solvent (e.g. dioxane).

Compounds of formula IV may alternatively be prepared by cyclisation of a compound of formula XVI or a compound of formula XVII,

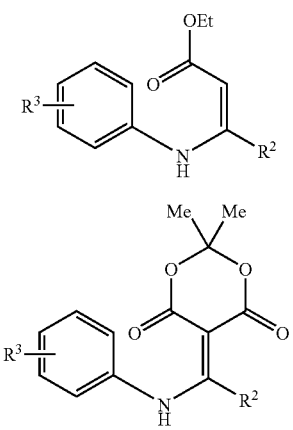

XVI

XVII wherein $R^2$ and $R^3$ are as hereinbefore defined, for example under conditions known to those skilled in the art, such as at elevated temperature (e.g. from 70 to 250° C., for example as achieved through microwave heating) in the presence of a suitable solvent (e.g. dichlorobenzene or diphenyl ether).

Compounds of formula XI may be prepared by reaction of a corresponding compound of formula XVIII,

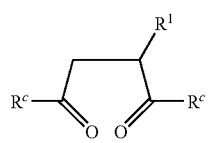

XVIII wherein $R^c$ represents halo, OH or $C_{1-9}$ alkoxy, with a compound of formula XIII as hereinbefore defined, for example under conditions known to those skilled in the art. For example, when $R^c$ represents OH the reaction may be carried out in the presence of a suitable coupling reagent and optionally in the presence of a suitable base, an appropriate solvent and/or a catalyst (e.g. 1-hydroxybenzotriazole hydrate). Alternatively, when $R^c$ represents halo (e.g. chloro), the reaction may be carried out, for example, at ambient temperature (or below) in the presence of a suitable base and/or an appropriate solvent.

In connection with the reaction between compounds of formulae XVIII and XIII, suitable coupling reagents include, for example:

1,1'-carbonyldiimidazole; N,N'-dicyclohexylcarbodiimide, 1-(3-dimethylamino-propyl)-3-ethylcarbodiimide (or hydrochloride thereof); N,N'-disuccinimidyl carbonate; benzotriazol-1-yloxytris(dimethylamino)phosphonium hexafluoro-phosphate; 2-(1H-benzotriazol-1-yl)-1,1,3,3-tetramethyluronium hexafluorophosphate; benzotriazol-1-yloxytris-pyrrolidinophosphonium hexafluorophosphate; bromo-tris-pyrrolidino-phosphonium hexafluorophosphate; 2-(1H-benzotriazol-1-yl)-1,1,3,3-tetramethyluronium tetrafluorocarbonate; 1-cyclohexylcarbodiimide-3-propyloxymethyl polystyrene; O-(7-azabenzotriazol-1-yl)-N,N,N',N'-tetramethyluronium hexafluorophosphate; and O-benzotriazol-1-yl-N,N,N',N'-tetramethyluronium tetrafluoroborate.

Further, suitable bases include, for example, sodium hydride, sodium bicarbonate, potassium carbonate, pyridine, triethylamine, dimethylaminopyridine, diisopropylamine, sodium hydroxide, potassium tert-butoxide and/or lithium diisopropylamide. Also, appropriate solvents that may be mentioned include tetrahydrofuran, pyridine, toluene, dichloromethane, chloroform, acetonitrile, dimethylformamide, trifluoromethylbenzene, dioxane or triethylamine.

Compounds of formula XII, wherein $L^3$ represents $OS(O)_2R^{8f}$ may be prepared by:

reduction of a corresponding compound of formula XVIII in which Fe represents $C_{1-9}$ alkoxy in the presence of a suitable reducing agent (e.g. lithium aluminium hydride or diisobutylaluminium hydride), for example under conditions known to those skilled in the art, such as at ambient or elevated temperature (e.g. 50 to 70° C.) in the presence of a suitable organic solvent (e.g. tetrahydrofuran); followed by reaction of the resulting diol with a compound of formula XIX

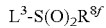 $L^3\text{-S(O)}_2R^{8f}$        XIX wherein $L^3$ and $R^{8f}$ are as hereinbefore defined, for example under conditions known to those skilled in the art, such as at ambient or reduced temperature (e.g. 0 to 5° C.) in the presence of a suitable organic solvent (e.g. tetrahydrofuran or dichloromethane) and an appropriate base (e.g. triethylamine or 4-dimethylaminopyridine).

Compounds of formula XVI may be prepared by reacting a corresponding compound of formula XIV, as hereinbefore defined, with a compound of formula XV as hereinbefore defined, for example under conditions known to those skilled in the art, such as at ambient or elevated temperature (e.g. 100 to 120° C.), optionally in the presence of a solvent.

Compounds of formula XVII may be prepared according to or by analogy with procedures known to those skilled in the art (e.g. those described in *Synthesis* 482 (1987)), such as by reaction of a corresponding compound of formula XIV, as hereinbefore defined, with a compound of formula XX,

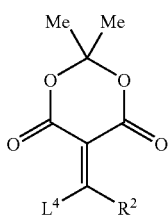

XX wherein L⁴ represents a suitable leaving group (e.g. ethylthio) and R² is as hereinbefore defined, for example under conditions known to those skilled in the art, such as at ambient or elevated temperature (e.g. 100 to 120° C.), optionally in the presence of a suitable solvent.

Compounds of formula XVIII in which R¹ is —CH₂-aryl and $R^c$ represents $C_{1-9}$ alkoxy may be prepared by reaction of a corresponding compound of formula XXI,

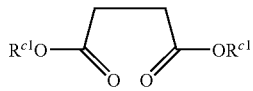

XXI wherein $R^{C1}$ represents $C_{1-9}$ alkoxy, with a compound of formula XXII, aryl-CHO        XXII wherein aryl is as hereinbefore defined, for example under conditions known to those skilled in the art, such as at ambient or elevated temperature (e.g. 60 to 80° C.) in the presence of an appropriate base (e.g. t-BuOK) and a suitable organic solvent (e.g. t-butanol), followed by reduction of the resultant alkenyl intermediate, for example by catalytic hydrogenation under conditions known to those skilled in the art, such as at ambient or elevated temperature (e.g. 50 to 65° C.) in the presence of a catalyst (e.g. Pd/C) and a suitable organic solvent (e.g. ethanol or methanol).

Compounds of formula XVIII in which R¹ is —CH₂-aryl and $R^c$ represents OH may by reaction of a corresponding compound of formula XXIII,

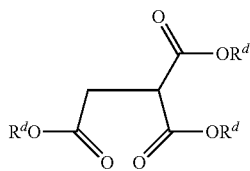

XXIII wherein each $R^d$ independently represents $C_{1-9}$ alkyl, with a compound of formula XXIV, aryl-CH₂-L³        XXIV wherein aryl and L³ are as hereinbefore defined, for example under conditions known to those skilled in the art, such as at ambient or elevated temperature (e.g. 40 to 120° C.) in the presence of an appropriate base (e.g. K₂CO₃, NaOH, NaH, triethylamine or 4-dimethylaminopyridine) and a suitable organic solvent (e.g. DMF, tetrahydrofuran, dichloromethane or ethanol), followed by hydrolysis of the three ester groups (i.e. conversion of each $R^d$ to H) and mono-decarboxylation, for example under conditions known to those skilled in the art, such as at elevated temperature (e.g. 50 to 65° C.) in the presence of an appropriate aqueous acid (e.g. sulfuric or hydrochloric acid) and a suitable organic solvent (e.g. ethanol or methanol).

Compounds of formula XVIII in which $R^c$ represents $C_{1-9}$ alkoxy may be prepared by reaction of a compound of formula XXV

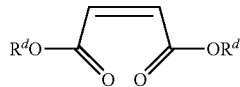

XXV wherein $R^d$ is as hereinbefore defined, with a compound of formula XXVI,

R¹-halo        XXVI wherein R¹ and halo are as hereinbefore defined, for example under conditions known to those skilled in the art, such as at ambient or elevated temperature (e.g. 60 to 120° C.) in the presence of an appropriate palladium-based catalyst for Heck coupling and a suitable organic solvent (e.g. dimethylformamide, toluene, acetonitrile or tetrahydrofuran), and optionally in the presence of a suitable base (e.g. K₂CO₃, Ag₂CO₃, NaOAc or triethylamine), and/or a co-catalyst (e.g. n-Bu₄NBr or NaI), followed by catalytic hydrogenation of the resultant alkenyl intermediate, for example under conditions known to those skilled in the art, such as at ambient or elevated temperature (e.g. 50 to 65° C.) in the presence of a suitable hydrogenation catalyst (e.g. Pd/C, [(R)- or (S)-DI-PAMP]RhCl, or [(R)- or (S)-BINAP]Ru(OAc)₂) and an appropriate organic solvent (e.g. ethanol or methanol).

The palladium-based catalyst for Heck coupling may comprise a source of palladium(0) (e.g. Pd(OAc)₂, Pd(OCOCF₃)₂(PPh₃)₂, Pd(dba)₂, Pd(PPh₃)₄) and, optionally, a suitable ligand for coordinating to palladium (e.g. PPh₃, P(Oi-Pr)₃ or tri-(o-tolyl)phosphine).

Compounds of formulae II, III, IV, V, VI, VII, VIII, IX, X, XII, XIII, XIV, XV, XIX, XX, XXI, XXII, XXIII, XXIV, XXV and XXVI are either commercially available, are known in the literature, or may be obtained by analogy with the processes described herein, or by conventional synthetic procedures, in accordance with standard techniques, from readily available starting materials using appropriate reagents and reaction conditions.

Substituents on alkyl, alkenyl, alkynyl, cycloalkyl, cycloalkenyl, aryl and heterocyclic groups in compounds of formulae I, II, III, IV, V, VI, VII, VIII, IX, X, XI, XII, XIII, XIV, XV, XVI, XVII, XVIII, XIX, XX, XXI, XXII, XXIII, XXIV, XXV and XXVI may be introduced and/or interconverted using techniques well known to those skilled in the art by way of standard functional groups interconversions, in accordance with standard techniques, from readily available starting materials using appropriate reagents and reaction conditions. For example, benzyloxy may be converted to hydroxy, etc.

Compounds of formula I may be isolated from their reaction mixtures using conventional techniques. For example, compounds of formula I may be isolated by conversion to an acid (e.g. hydrochloric acid) salt (e.g. by way of addition of acid to the crude product) and then recrystallisation of the salt from a suitable solvent (e.g. methanol or, particularly, ethanol). Alternatively, the salt can simply be washed with or slurried in the presence such a suitable solvent in order to isolate the pure acid salt of the compound of formula I.

In accordance with the present invention, pharmaceutically acceptable derivatives of compounds of formula I also include "protected" derivatives, and/or compounds that act as prodrugs, of compounds of formula I.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography. The various stereoisomers may be isolated by separation of a racemic or other mixture of the compounds using conventional, e.g. HPLC techniques. Alternatively the desired optical isomers may be made by reaction of the appropriate optically active starting materials under conditions which will not cause racemisation or epimerisation, or by derivatisation (for example with a homochiral acid), followed by separation of the diastereomeric derivatives by conventional means (e.g. fractional crystallisation, HPLC, chromatography over silica). All stereoisomers are included within the scope of the invention.

It will be appreciated by those skilled in the art that in the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino include tert-butyloxycarbonyl and benzyloxycarbonyl.

The protection and deprotection of functional groups may take place before or after coupling, or before or after any other reaction in the above-mentioned schemes.

Protecting groups may be removed in accordance with techniques that are well known to those skilled in the art and as described hereinafter.

Persons skilled in the art will appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is described in "Protective Groups in Organic Chemistry", edited by J W F McOmie, Plenum Press (1973), and "Protective Groups in Organic Synthesis", 3$^{rd}$ edition, T. W. Greene & P. G. M. Wutz, Wiley-Interscience (1999).

Protected derivatives of compounds of formula I may be converted chemically to compounds of the invention using standard deprotection techniques (e.g. hydrogenation). The skilled person will also appreciate that certain compounds of formula I may also be referred to as being "protected derivatives" of other compounds of formula I.

Those skilled in the art will also appreciate that certain compounds of formula I will be useful as intermediates in the synthesis of certain other compounds of formula I.

When used in the above-described method of treatment, the compounds of formula I (e.g. compounds of formula Ia or Ib) may be formulated for administration to a patient. In this respect, according to a still further aspect of the invention there is provided a pharmaceutical formulation including a compound of formula I (e.g. compounds of formula Ia or, particularly, Ib), in admixture with a pharmaceutically acceptable adjuvant, diluent or carrier.

The above-mentioned medicaments, (components of) combination products and pharmaceutical formulations may be prepared according to methods known to those skilled in the art, for example by mixing the compounds of formulae I, Ia or Ib with excipient or excipients.

When formulated with excipients, the compounds of formulae I, Ia or Ib may be present in the above-mentioned medicaments, (components of) combination products and pharmaceutical formulations in a concentration from 0.1 to 99.5% (such as from 0.5 to 95%) by weight of the total mixture.

When administered to patients by way of any of the above-mentioned medicaments, (components of) combination products and pharmaceutical formulations, compounds of formulae I, Ia or Ib will normally be administered orally, by any parenteral route or via inhalation.

In the case of animals, compounds of formulae I, Ia or Ib can also be administered by incorporation of the compound of formulae I, Ia or Ib into feed or drinking water.

One preferred route of administration of compounds of the invention is oral.

Suitable daily doses of the compounds of the invention in prophylactic and/or therapeutic treatment of mammals (e.g. humans) include, for example, 0.001-100 mg/kg body weight at peroral administration and 0.001-50 mg/kg body weight at parenteral administration.

In a particular embodiment of the invention, compounds of formulae I, Ia or Ib are administered topically. Thus, according to the invention there is provided:

(I) a topical pharmaceutical composition comprising a compound of formula I, Ia or Ib in admixture with a pharmaceutically acceptable adjuvant, diluent or carrier;

(II) a combination product for topical administration comprising
  (A) a compound of formula I, Ia or Ib, as hereinbefore defined, and
  (B) a conventional antimicrobial agent, as hereinbefore defined, wherein each of components (A) and (B) is formulated in admixture with a pharmaceutically-acceptable adjuvant, diluent or carrier.

When used herein, the term "topical" includes references to formulations that are adapted for application to body surfaces (e.g. the skin or mucous membranes). Mucous membranes that may be mentioned in this respect include the mucosa of the vagina, the penis, the urethra, the bladder, the anus, the mouth (including the mucosa of the cheek, the soft palate, the under surface of tongue and the floor of the mouth), the nose, the throat (including the mucosa of the pharynx, the larynx, the trachea and the esophagus), the bronchi, the lungs, the eye and the ear.

In relation to (II) above, the combination product provides for the administration of component (A) in conjunction with component (B), and may thus be presented either as separate topical formulations, wherein at least one of those formulations comprises component (A) and at least one comprises component (B), or may be presented (i.e. formulated) as a combined topical preparation (i.e. presented as a single topical formulation including component (A) and component (B)).

Topical compositions, which are useful for treating disorders of the skin or of membranes (e.g. membranes accessible by digitation, such as membranes of the mouth, vagina, cervix, anus and rectum), include creams, ointments, lotions, sprays, gels and sterile aqueous solutions or suspensions. As such, topical compositions include those in which the active ingredient(s) is (are) dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components (for example, when the formulation is an aqueous gel, components in addition to water) selected from the following list:

- a solubilising agent or solvent (e.g. a βcyclodextrin, such as hydroxypropyl β-cyclodextrin, or an alcohol or polyol such as ethanol, propylene glycol or glycerol);
- a thickening agent (e.g. hydroxyethylcellulose, hydroxypropylcellulose, carboxymethylcellulose or carbomer);
- a gelling agent (e.g. a polyoxyethylene-polyoxypropylene copolymer);
- a preservative (e.g. benzyl alcohol, benzalkonium chloride, chlorhexidine, chlorbutol, a benzoate, potassium sorbate or EDTA or salt thereof); and
- pH buffering agent(s) (such as a mixture of dihydrogen phosphate and hydrogen phosphate salts, or a mixture of citric acid and a hydrogen phosphate salt).

The amount of compound of formulae I, Ia or Ib used in topical compositions or combination products will depend, inter alia, upon the particular nature of the composition or combination product, as well as its intended use. In any event, those skilled in the art will be able to determine, by routine and non-inventive methods, amounts of compound of formulae I, Ia or Ib that can be employed. Typically, however, the compound of formulae I, Ia or Ib will be present in the topical composition or combination product at from 0.01 to 25% by weight (e.g. from 0.1 to 10% by weight, such as from 0.1 to 5% by weight or, particularly, from 0.5 to 3% (e.g. 2% or 1%) by weight) of the composition or product.

Particular topical compositions that may be mentioned are those that comprise a compound of formula I (e.g. at 0.5 to 3%, such as 2% or 1%, by weight) and:
(a) water;
(b) one or more polar, non-aqueous solvents (e.g. an alcohol or polyol such as ethanol, propylene glycol and/or glycerol);
(c) a preservative (e.g. benzyl alcohol);
(d) a thickening agent (e.g. hydroxyethylcellulose); and, optionally
(e) pH buffering agent(s) (such as a mixture of dihydrogen phosphate and hydrogen phosphate salts).

In particular compositions, and depending, inter alia, upon the amount of compound of formula I present (typically, the higher the amount of the compound of formula I, the larger the amount of polar, non-aqueous solvents required to solublise the compound):

(i) water may be present at from 55 to 75% (e.g. from 60 to 72.5%) by weight;
(ii) the one or more polar, non-aqueous solvents may (together) be present at from 15 to 40% (e.g. from 24 to 35%) by weight;
(iii) glycerol, if used, may be present at from 5 to 25% (e.g. from 15 to 20%) by weight;
(iv) ethanol, if used, may be present at from 3 to 10% (e.g. from 5 to 8%) by weight;
(v) propylene glycol, if used, may be present at from 2 to 15% (e.g. from 4 to 6%) by weight;
(vi) the preservative may be present at from 0.1 to 3% (e.g. about 1%) by weight;
(vii) the thickening agent may be present at from 1 to 5% (e.g. about 2% by weight).

In further particular topical compositions, the pH buffering agent(s) may, if employed and when dissolved in the water component of the composition, provide a pH in the range of 5 to 7 (e.g. about pH 5.5).

Methods of producing topical pharmaceutical compositions such as creams, ointments, lotions, sprays and sterile aqueous solutions or suspensions are well known in the art. Suitable methods of preparing topical pharmaceutical compositions are described, for example in WO 95/10999, U.S. Pat. No. 6,974,585, WO 2006/048747, as well as in documents cited in any of these references.

Topical pharmaceutical compositions and combination products according to the present invention may be used to treat a variety of skin or membrane disorders, such as infections of the skin or membranes (e.g. e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described hereinbefore, (e.g. any of the *Staphylococci, Streptococci, Mycobacteria* or *Pseudomonas* organisms mentioned hereinbefore, such as *S. aureus* (e.g. Methicillin resistant *S. aureus* (MRSA))).

Particular bacterial conditions that may be treated by topical pharmaceutical compositions and combination products according to the present invention also include the skin- and membrane-related conditions disclosed hereinbefore, as well as: acne vulgaris; acne rosacea; rosacea (including erythematotelangiectatic rosacea, papulopustular rosacea, phymatous rosacea and ocular rosacea); erysipelas; erythrasma; eethyma; eethyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); intertrigo; atopic eczma with staphylococcal carriage; as well as infected eczma, burns, abrasions and skin wounds.

Particular fungal conditions that may be treated by topical pharmaceutical compositions and combination products according to the present invention also include the skin- and membrane-related conditions disclosed hereinbefore, as well as: candidiasis (e.g. oropharyngeal candidiasis, vaginal candidiasis or balanitis); sporotrichosis; ringworm (e.g. tinea pedis, tinea cruris, tinea capitis, tinea unguium or tinea corporis); tinea versicolor; and infections with *Trichophyton, Microsporum, Epidermophyton* or *Pityrosporum ovale* (*Malassezia furfur*) fungi.

In addition to the above, the topical compositions and combination products according to the present invention may be used to effect clearance (e.g. prophylactic clearance) of:
(a) Staphylococci (e.g. MRSA);
(b) Propionibacteria, such as *Propionibacterium acnes*; or
(c) fungi (such as *Candida albicans, Cryptococcus neoformans, Histoplasma capsulatum, Epidermophyton floccosum, Malassezia* (e.g. *Malassezia furfur*) or, particularly, *Trichophyton* (e.g. *Trichophyton violaceum, Trichophyton mentagrophytes* or, particularly, *Trichophyton rubrum*), from the skin or membranes of a patient in need of such clearance.

In the case of Staphylococci the clearance may be effected particularly from the skin (e.g. before surgery or insertion of medical equipment such as i.v. needles, catheters and tracheostomy or feeding tubes), nose (e.g. anterior nares), wounds or atopic eczma (atopic dermatitis).

Thus, according to a further aspect of the invention, there is provided a method for treating any of the conditions and infections mentioned above in connection with topical compositions, or of effecting clearance of microorganisms as described above, the method comprising administering to a patient in need thereof an effective amount of a topical composition as hereinbefore defined, or a combination product as hereinbefore defined.

Similarly, there is provided a topical composition as hereinbefore defined, or a combination product for topical administration as hereinbefore defined for use in the treatment of any of the conditions and infections mentioned above in connection with topical compositions, or in effecting clearance of microorganisms as described above.

The microorganisms killed by application of the topical composition or combination product may be clinically latent. Thus, the invention also encompasses a method of killing clinically latent microorganisms in a mammal infected with such latent microorganisms, the method comprising administering to said mammal a microbicidally effective amount of a topical composition according to the first aspect of the invention, or a combination product according to the second aspect of the invention.

When employed to treat a microbial infection, the compounds of formulae I, Ia or Ib, whether administered on their own or in combination with a conventional antimicrobial agent, are preferably administered in a smaller number of doses than is necessary for the treatment of the same microbial infection utilising conventional antimicrobial agents only (e.g. in less than 7, 6, 5, 4, or 3 doses, such as in 2 doses or, particularly, 1 dose).

In this respect, a still further aspect of the invention provides a method of reducing the dose of conventional antimicrobial agent required to treat a microbial infection, the method comprising co-administering a compound of formula I, Ia or Ib.

Compounds of formulae I, Ia or Ib have the advantage that they may be used to kill clinically latent microorganisms. Further, in treating microbial infections, compounds of formulae I, Ia or Ib may possess the further advantage that they allow for a shorter period of therapy (either alone or in combination with a conventional antimicrobial agent), thus increasing patient compliance (through, for example, the need to take fewer or smaller doses of antimicrobial agents) and/or minimising the risk of generating sub-populations of microorganisms that are (genetically) resistant to conventional antimicrobial agents.

Additionally, compounds according to the invention may have the advantage that they may be more efficacious than, be less toxic than, have a broader range of activity than, be more potent than, produce fewer side effects than, or have other useful pharmacological properties over compounds known in the prior art.

Biological Tests

Test procedures that may be employed to determine the biological (e.g. bactericidal or antibacterial) activity of the compounds of formulae I, Ia or Ib include those known to persons skilled in the art for determining:
(a) bactericidal activity against stationary-phase or "persister" bacteria (i.e. "clinically latent" bacteria); and
(b) antibacterial activity against log phase bacteria.

In relation to (b) above, methods for determining activity against log phase bacteria include a determination, under standard conditions (i.e. conditions known to those skilled in the art, such as those descried in WO 2005/014585, the disclosures of which document are hereby incorporated by reference), of Minimum Inhibitory Concentration ("MIC") or Minimum Bactericidal Concentration ("MBC") for a test compound.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound. Specific examples of such methods are described below.

Protocol for Pyogenic Bacteria

Bacterial Strains

The strains used for screening are shown in the following table.

| *Staphylococcus aureus* (Oxford) | Gram positive | Reference strain |
|---|---|---|
| *Escherichia coli* K12 | Gram negative | Reference strain |
| *Enterococcus* | Gram positive | Clinical isolate |
| *Pseudomonas* | Gram negative | Clinical isolate |
| Methicillin resistant *S. aureus* (MRSA) | Gram positive | Clinical isolate |
| *Klebsiella aerogrenes* | Gram negative | Clinical isolate |
| *E. coli* | Gram negative | Clinical isolate |
| *Streptococcus pneumoniae* | Gram positive | Reference strain |
| *Streptococcus pyogenes* Group A Streptococci | Gram positive | Reference strain |
| Group B streptococci (*Streptococcus agalactiae*) | Gram positive | Reference strain |
| *Streptococcus viridans* | Gram positive | Reference strain |
| *Haemophilus influenzae* | Gram negative | Reference strain |
| Coagulase negative *staphylococcus* (CNS) | Gram positive | Reference strain |
| *Propionibacterium acnes* | Gram positive | Reference strain (NCTC 737) |

Growth of Bacteria

The bacteria (except for streptococci and *H. influenzae* and *P. acnes*) were grown in 10 mL of nutrient broth (No. 2 (Oxoid)) overnight at 37° C., with continuous shaking at 120 rpm. Streptococci and *H. influenzae* were grown overnight in Todd-Hewitt broth (Sigma) without shaking. *P. acnes* was grown overnight in 10 mL of nutrient broth without shaking. The overnight cultures were diluted (1000×) in 100 mL of growth medium and then incubated with or without shaking for 10 days. Viability of the bacteria was estimated by colony forming unit (CFU) counts at 2 hours intervals at the first 24 hours and at 12-24 hours afterwards. From serial 10-fold dilutions of the experimental cultures, 100 µL samples were added to triplicate plates of nutrient agar plates (Oxoid) and blood agar plates (Oxoid). Colony forming units (CFU) were counted after incubation of the plates at 37° C. for 24 hours. CFU counts of *P. acnes* were estimated after the plates were incubated under anaerobic conditions for 48 hours.

Log-phase cultures: The above-described overnight cultures were diluted (1000×) with iso-sensitest broth. The cultures were then incubated at 37° C. with shaking for 1-2 hours to reach log CFU 6, except for streptococci, *H. influenzae* and *P. acnes*, which were incubated at 37° C. without shaking. These cultures were served as log-phase cultures.

Stationary phase cultures: Cultures incubated for more than 24 hours are in stationary phase. For drug screening, 5-6 day old stationary phase cultures are used as shown in FIG. 1 (the periods between two arrows). The cultures were diluted with phosphate buffered saline to log 6, which were used to incubate with testing compounds.

Measurements of Bactericidal Activity Against Log-phase Cultures

Different concentrations of each test compound were incubated with the log-phase cultures in 96 well plates for various periods of time (2, 4, 6, 12, 24 hours). Bactericidal activity was then examined by taking a spectrophotometer reading (using a plate reader) of the resulting cultures, as well as by CFU counts as described above.

Measurements of Bactericidal Activity Against Stationary-phase Cultures

Different concentrations of each test compound were incubated with stationary phase cultures (5-6 day cultures) in 96 well plates for 24 or 48 hours. Bactericidal activity was then determined by taking CFU counts of the resulting cultures, as described above.

Measurements of Bactericidal Activity Against Persistent Bacteria

An antibiotic (e.g. gentamicin) was added to 5-6 day stationary-phase cultures to the final concentration of 50 to 100 µg/mL for 24 hours. After 24 hours of antibiotic treatment, the cells are washed 3 times with phosphate buffered saline (PBS), and then resuspended in PBS. The surviving bacterial cells are used as persisters. Viability is estimated by CFU counts. The persisters were then used in measurements of bactericidal activity for test compounds.

Different concentrations of each test compound were incubated with the (persister) cell suspension in 96 well plates for various periods of time (24 and 48 hours). Bactericidal activity was then determined by taking CFU counts of the resulting cultures, as described above.

Protocol for *M. tuberculosis*
Growth of *M. tuberculosis*

*M. tuberculosis* H37Rv was grown in 10 mL of Middlebrook 7H9 broth containing 0.05% Tween 80 supplemented with 10% ADC without disturbing for up to 100 days. In order to obtain evenly dispersed cultures prior to experimental treatment, clumps in the cultures were broken up by vortexing the cultures in the presence of 2 mm glass beads (Philip Harris Scientific, Staffordshire, UK) for 2 minutes, followed by sonication in a water bath sonicator (Branson Ultrasonic B. V.) for 5 minutes. The numbers of viable *M. tuberculosis* in the cultures were determined by colony forming unit (CFU) counts on Middlebrook 7H11 agar. Serials of 10-fold dilutions of the cultures are made in Middlebrook 7H9 broth with 0.05% (v/v) Tween 80 but without ADC. Then, 100 µL of samples was added to one-third segments of the agar plates in duplicate. The plates were incubated in polythene bags for 3 weeks at 37° C.

Measurements of Bactericidal Activity Against Log-phase Cultures

Different concentrations of each test compound were incubated with log-phase cultures (4 day cultures) for various time periods (4, 8, 16, 24 days). Bactericidal activity was then determined by taking CFU counts of the resulting cultures, as described above.

Measurements of Bactericidal Activity Against Stationary-phase Cultures and Persistent Bacteria Model 1—Stationary-phase cultures. Different concentrations of each test compound were incubated with the sonicated 100-day cultures, each concentration to a separate 10 mL culture. After incubation for 5 days, counts of viable CFU were determined by inoculating a pair of 7H11 plates with 100 µL of 10-fold serial dilutions of the resulting cultures.

Model 2—Persistent bacteria selected by rifampicin. Rifampicin (100 mg/L) was added to each of a set of sonicated 100-day cultures, which cultures were then incubated for 5 days. After the first day of incubation, no colonies could be obtained on plates inoculated from the culture. After washing twice with PBS by centrifugation, fresh (and rifampicin-free) 7H9 medium was added to make up the volume to 10 mL and the test compound was added in the same concentrations as in model 1. After further incubation for 7 days, CFU counts were determined by inoculating 1 mL from each container onto a 7H11 plate. These plates were then incubated for 2 weeks and the very small colonies were counted and marked. After a further 2 weeks of incubation, any additional unmarked colonies (i.e. those that grew slowly) were added to the counts. Control studies have shown that plate counts begin to yield colonies on subculture after about 4 days of incubation of the rifampicin-free cultures.

Model 3. The procedure is similar to model 2, but only different concentrations of the test compound was added to the 100-day culture at three days after the rifampicin treatment. At the end of the 7-day incubation period (4 days with candidate drugs plus rifampicin), all cultures were washed, replacing with medium free of test compound, and then were incubated for a further 7 days before CFU counts were determined.

Protocol for *Candida albicans*

*Candida albicans*, a clinical isolate was used. The strain was grown in 10 mL of Potato dextrose broth medium (Sigma-Aldrich) at 24° C., with continuous shaking at 120 rpm for 24 hours. Then, 1 mL of the culture was inoculated in 100 mL of fresh broth medium, which was incubated at the same conditions for 6 days.

Log-phase cultures: The above-described 24 hour culture was diluted (100×) with potato glucose broth medium. The cultures were then incubated at 24° C. with shaking for 20-24 hours served as log-phase cultures. The log phase cultures were diluted with fresh broth medium to CFU log 6, which were used to test the activities of compounds.

Stationary phase cultures: For drug screening, 5-6 day old stationary phase cultures were used. The stationary phase cultures were diluted with phosphate buffered saline to CFU log 6, which were used to examine the activities of test compounds.

Measurements of Activity Against Log-phase Cultures

Different concentrations of each test compound were incubated with the log-phase cultures in 96 well plates for various periods of time (2, 4, 6, 12, 24 hours). The activity of drugs was then examined by taking a spectrophotometer reading (using a plate reader) of the resulting cultures, as well as by CFU counts as described above.

Measurements of Activity Against Stationary-phase Cultures

Different concentrations of each test compound were incubated with stationary phase cultures (5-6 day cultures) in 96 well plates for 24 or 48 hours. The activity was then determined by taking CFU counts of the resulting cultures, as described above.

Skin (Topical) Models

In addition to in vitro testing against stationary- and log-phase bacteria, compounds of formulae I, Ia or Ib may also be tested in various in vivo models, including those known to those skilled in the art. For example, for determination of compound activity against bacteria in or on the skin, protocols that may be followed include those described in *Antimicrobial Agents and Chemotherapy* 49(8), 3435-41 (2005), as well as the following.

Mouse Superficial Skin Bacterial Model (Intact Skin)

ICR or BALB/c mice aged 6-8 weeks were obtained from Harlan UK. The mice were anaesthetized by intraperitoneal injection of 200 µL of ketamine hydrochloride/xylazine solution. Fur on the back of the mouse was removed using an electrical clipper. A 2 cm$^2$ (2 cm×1 cm) area of skin was marked with a marker pen. The marked skin area was swabbed 3 times using a disposable swab in order to examine the bacterial numbers on the skin. The bacteria on the swab were spread on blood agar plates (Oxoid™).

Log-phase or stationary phase bacterial or yeast cultures were used. The cultures were concentrated by centrifugation to obtain 10$^9$ to 10$^{10}$ CFU/mL. The cell pellet was resuspended with nutrient broth or PBS and glycerol (50%). 15-20 µL of the cell suspension was added to the skin area (2 cm$^2$) which gave 10$^{6-7}$ CFU on the skin. The skin was allowed to dry for about 15 min. Solutions of test compound at different concentrations were applied on the skin area for different periods of time.

Bacterial or yeast numbers on the skin were estimated as follows: After the mouse was euthanised, the skin at the marked area was cut and added to a 2 mL tube containing 1 mL water and glass beads (1 mm). The skin was homogenised using a reciprocal shaker (Hybaid Ltd, UK) for 45 seconds (speed setting 6.5) or votexing for 1 min. Residual test compound was removed by washing 3 times with water or PBS (if the test compound precipitated in the buffer system, water alone was used for washing). CFU counts were performed after a serial of 10 fold dilution of the homogenates. 100 µL samples were added to one third of blood agar plates (Oxoid™) in duplicate. Colony forming units (CFU) were then counted using aCoLye (a colony counter) after incubation of the bacterial plates at 37° C. for 24 hours or yeast plates at 24° C. for 48 hours.

Mouse Superficial Skin Infection Model (Tape-stripping Infection Model)

ICR or BALB/c mice aged 6-8 weeks were obtained from Harlan UK. The mice were anaesthetized by intraperitoneal injection of 200 µL of ketamine hydrochloride/xylazine solution. The fur of the mice on the back was removed by electric clipper. An area of 2 cm$^2$ skin was tape-stripped using autoclave tape. The skin was stripped 10 times in succession. After this procedure, the skin became visibly damaged and was characterized by reddening and glistening but no regular bleeding. Buprenorphine was given during the anaesthetic period and every 12 hours for up to 3 days to reduce prolonged pain. After stripping of the skin, a bacterial infection was initiated by placing 10 µL of bacterial cell suspension containing 10$^7$ cells from overnight or stationary phase cultures on the damaged skin area. At 0 and 4 hours after infection, 3 mice were killed to estimate the CFU counts on the skin. After 24 hours, solutions of test compound at different concentrations were applied on the skin area for different periods of time. The experiments were terminated 18 h after the last topical treatment.

Bacterial numbers of the wounds were estimated as follows: After the mouse was been euthanised, the wounds, approximately 2 cm$^2$ were cut and added to a 2 mL tube containing 1 mL water and glass beads (1 mm). The skin was homogenised using a reciprocal shaker (Hybaid Ltd, UK) for 45 seconds (speed setting 6.5). Residual test compound was removed by washing 3 times with water. CFU counts were performed after a serial of 10 fold dilution of the homogenates. 100 µL samples were added to one third of blood agar plates (Oxoid™) in duplicate. Colony forming units (CFU) were counted using aCoLye (a colony counter) after incubation of the plates at 37° C. for 24 hours.

The invention is illustrated, but in no way limited, by the following examples and by reference to the figures, which present data relating, inter alia, to the biological studies described above.

KEY

Figure 1:
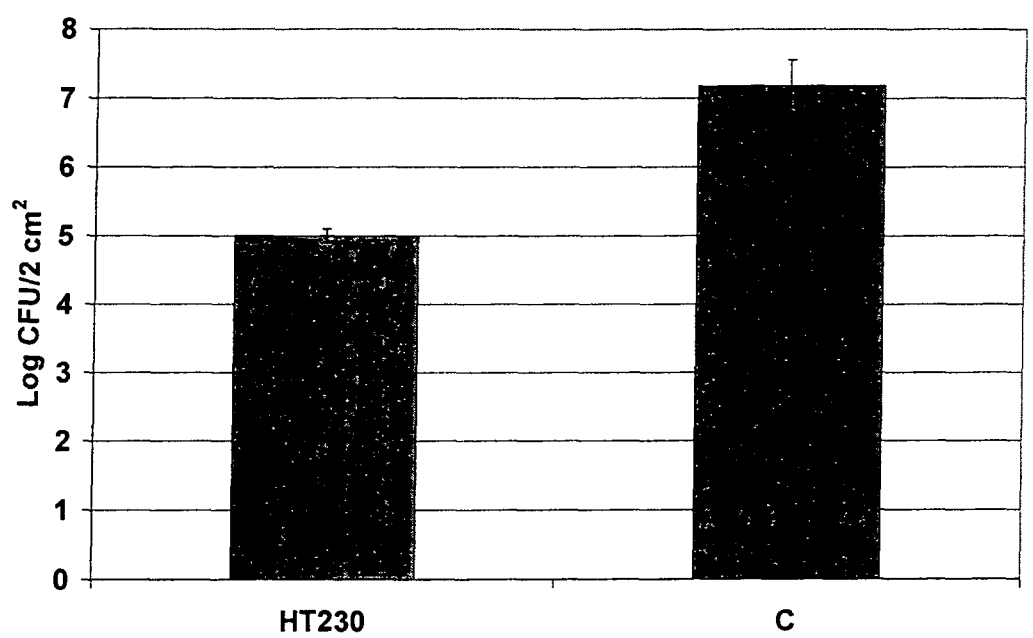
FIG. 1 illustrates the effect of HT230 against stationary phase *Staphylococcus aureus* on infected mouse skin. The compound HT230 was administered as a solution in water, solublised with 10% (by weight) of hydroxypropyl β-cyclodextrin.
Figure 2:
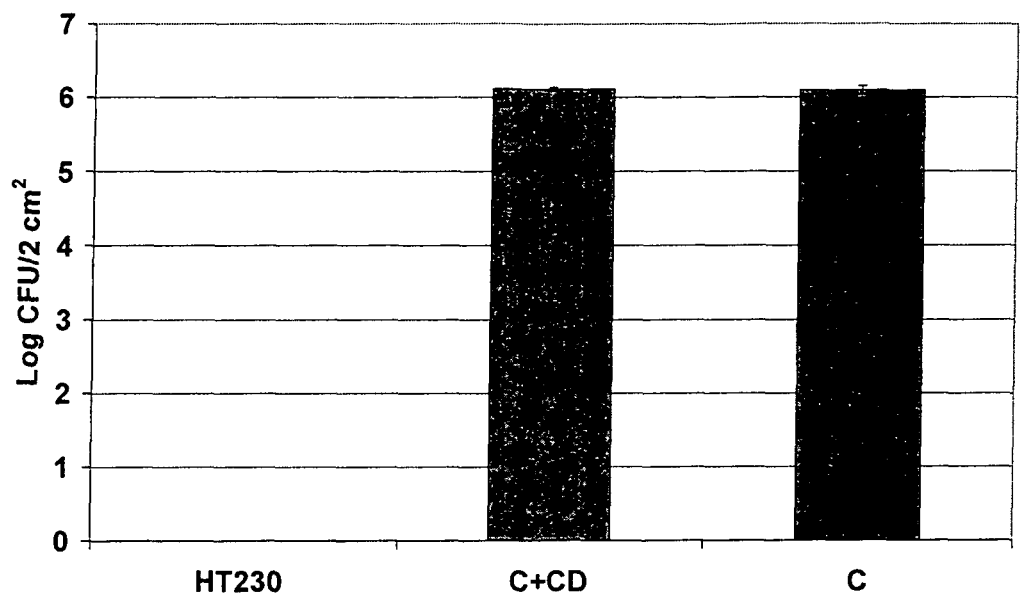
FIG. 2 illustrates the effect of HT230 against stationary phase *Staphylococcus aureus* on mouse intact skin. The compound HT230 was administered as a solution in water, solublised with 10% (by weight) of hydroxypropyl β-cyclodextrin.
Figure 3:
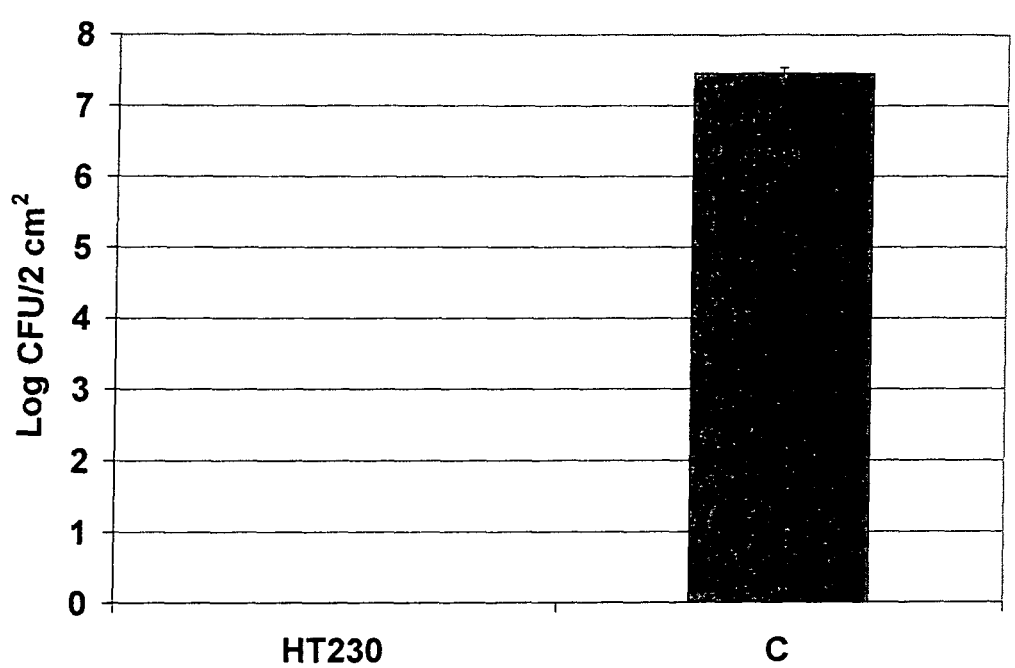
FIG. 3 illustrates the effect of HT230 against stationary phase *Candida albicans* on intact mouse skin. The compound HT230 was administered as a solution in water, solublised with 10% (by weight) of hydroxypropyl β-cyclodextrin.

HT230: 4-(3-benzylpyrrolidin-1-yl)-2-methyl-6-phenoxyquinoline
C: control (no treatment)
C+CD: a control group treated (by topical administration) with the solvent system employed to dissolve HT230 (i.e. an aqueous solution of 10% (by weight) hydroxypropyl β-cyclodextrin).

EXAMPLES

General Experimental Procedures $^1$H NMR spectra were recorded at ambient temperature using either a Varian Unity Inova (400 MHz) spectrometer or a Bruker Advance DRX (400 MHz) spectrometer, both with a triple resonance 5 mm probe. Chemical shifts are expressed in ppm relative to tetramethylsilane. The following abbreviations have been used: s=singlet, d=doublet, dd=double doublet, t=triplet, q=quartet, m=multiplet.

High Pressure Liquid Chromatography—Mass Spectrometry (LCMS) experiments to determine retention times and associated mass ions were performed using the following methods:

Method A: Experiments performed on a Micromass Platform LCT spectrometer with positive ion electrospray and single wavelength UV 254 nm detection using a Higgins Clipeus C18 5 micron 100×3.0 mm column and a 1 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Micromass Platform ZQ Quadrupole spectrometer with positive ion electrospray and single wavelength UV 254 nm detection using a Higgins Clipeus C18 5 micron 100×3.0 mm column and a 1 mL/minute flow rate. The initial solvent system was 95% solvent A and 5% solvent B for the first minute followed by a gradient up to 5% solvent A and 95% solvent B over the next 14 minutes. The final solvent system was held constant for a further 5 minutes.

Microwave experiments were carried out using either a Personal Chemistry Smith Synthesizer™ or Emrys Optimizer™ which use a single-mode resonator and dynamic field tuning, both of which give reproducibility and control. Temperatures from 40-250° C. can be achieved, and pressures of up to 20 bar can be reached.

Preparative HPLC was carried out using a 150×20.6 mm 7 micron Genesis $C_{18}$ column eluting at 10 ml/min with a gradient of water/MeCN (+0.1% formic acid or 0.1% trifluoroacetic acid). The fractions containing the desired product were concentrated. In some cases the compound was then converted to the hydrochloride salt by treatment with 1M hydrochloric acid, followed by evaporation.

Preparative chiral HPLC was carried out, unless otherwise specified, using a 250×20.6 mm 5 micron Chiralpak IA column eluting at 18 mL/min with a mixture of diethylamine (0.1%) and ethanol (7%) in heptane.

PREPARATIONS

Preparation 1

6-Benzyloxy-4-chloro-2-methyl-quinoline (i) 3-(4-Benzyloxyphenylamino)but-2-enoic acid ethyl ester 4-Benzyloxyaniline (10 g) and ethyl acetoacetate (6.9 g) were heated at 120° C. for 3 hours. The residue was purified by chromatography on silica eluting with a mixture of dichloromethane, and pentane. The desired fractions were concentrated and the sample evaporated to give the sub-title compound (7.8 g).

$^1$H NMR ($D_6$-DMSO) δ 10.2 (s, 1H), 7.5-7.3 (m, 7H), 7.2 (d, 2H), 7.0 (d, 2H), 5.2 (s, 1H), 4.1 (q, 2H), 1.8 (s, 3H), 1.4 (t, 3H)

(ii) 6-Benzyloxy-4-hydroxy-2-methylquinoline 3-(4-Benzyloxyphenylamino)but-2-enoic acid ethyl ester (3.1 g; see step (i) above) in dichlorobenzene (12 mL) was heated in a microwave at 220° C. for 45 minutes. The reaction mixture was diluted with pentane and the resulting precipitate was filtered, washed with pentane and dried to give 6-benzyloxy-4-hydroxy-2-methyl-quinoline.

$^1$H NMR ($D_6$-DMSO) δ 7.6 (s, 1H), 7.5-7.3 (m, 8H), 5.7 (s, 1H), 5.2 (s, 2H), 2.3 (s, 3H)

(iii) 6-Benzyloxy-4-chloro-2-methyl-quinoline

6-Benzyloxy-4-hydroxy-2-methylquinoline (2.6 g; see step (ii) above) in phosphorus oxychloride (40 mL) was heated at reflux for 3.5 hours. The mixture was then added carefully to ice/water and solid sodium carbonate added until the solution reached pH 8.0. The mixture was extracted with ethyl acetate, washed with water, dried (MgSO$_4$), filtered and evaporated. The resulting solid was triturated with diethyl ether to give the title compound (6.4 g) as a white solid.

$^1$H NMR (CDCl$_3$) δ 8.0 (d, 1H), 7.5-7.4 (m, 8H), 5.2 (s, 2H), 2.7 (s, 3H)

Preparation 2

4-Chloro-2-methyl-6-(pyridin-3-ylmethoxy)quinoline

4-Chloro-6-iodo-2-methylquinoline (0.61 g; see Preparation 6(ii) below), 3-pyridyl-carbinol (0.26 g), copper (I) iodide (0.038 g), caesium carbonate (0.78 g), 1,10-phenanthroline (0.072 g) in toluene (3 mL) was heated in a microwave at 160° C. for 40 minutes. The reaction mixture was diluted with water and extracted with ethyl acetate, washed with water, dried (MgSO$_4$), filtered and evaporated. The residue was purified by chromatography on silica eluting with a mixture of methanol and dichloromethane. Evaporation of the desired fractions gave the title compound as a pale pink solid.

$^1$H NMR (CDCl$_3$) δ 8.7 (s, 1H), 8.6 (d, 1H), 7.9 (d, 1H), 7.8 (d, 1H), 7.5 (s, 1H), 7.4 (d, 1H), 7.3 (m, 2H), 5.3 (s, 2H), 2.7 (s, 3H)

Preparation 3

4-Chloro-2-methyl-6-phenoxyquinoline (i) 4-Hydroxy-2-methyl-6-phenoxyquinoline

The sub-title compound was prepared using procedures analogous to those described in Preparation 6(i) below, but using 4-phenoxyaniline in place of 4-iodoaniline.

$^1$H NMR ($D_6$-DMSO) δ 7.5 (d, 1H), 7.4 (m, 5H), 7.2 (t, 1H), 7.1 (d, 2H), 2.3 (s, 3H)

(ii) 4-Chloro-2-methyl-6-phenoxyquinoline

The title compound was prepared using procedures analogous to those described in Preparation 1(iii) above, but using 4-hydroxy-2-methyl-6-phenoxyquinoline (see step (i) above) in place of 6-benzyloxy-4-hydroxy-2-methylquinoline.

$^1$H NMR (CDCl$_3$) δ 8.0 (d, 1H), 7.6 (s, 1H), 7.5 (d, 1H), 7.4 (m, 3H), 7.2 (t, 1H), 7.1 (d, 2H), 2.7 (s, 3H)

Preparation 4

Benzyl-(4-chloro-2-methylquinolin-6-yl)amine (i) N-(4-Hydroxy-2-methylquinolin-6-yl)acetamide The sub-title compound was prepared using procedures analogous to those described in Preparation 6(i) below, but using 4-aminoacetanilide in place of 4-iodoaniline.

$^1$H NMR ($D_6$-DMSO) δ 10.2 (s, 1H), 8.2 (s, 1H), 7.8 (d, 1H), 7.4 (d, 1H), 5.8 (s, 1H), 3.4 (s, 3H), 2.3 (s, 3H)

(ii) 6-Amino-4-chloroquinoline

N-(4-Hydroxy-2-methylquinolin-6-yl)acetamide (0.05 g; see step (i) above), methanol (2 mL) and 5 N hydrochloric acid (6 mL) was refluxed for 90 minutes. The reaction mixture was evaporated and the residue dissolved in ethyl acetate and sodium carbonate solution. The organic phase was washed with water, dried (Na$_2$SO$_4$), filtered and concentrated to give the sub-title compound as a pale yellow solid.

$^1$H NMR ($D_6$-DMSO) δ 7.7 (d, 1H), 7.4 (s, 1H), 7.2 (d, 1H), 7.0 (s, 1H), 5.8 (s, 2H), 2.5 (s, 3H)

(iii) Benzyl-(4-chloro-2-methylquinolin-6-yl)amine

6-Amino-4-chloroquinoline (0.1 g; see step (ii) above), benzaldehyde (0.055 g) and sodium tnacetoxyborohydride (0.22 g) in 1,2-dichloroethane was stirred overnight. The mixture was diluted with dichloromethane and washed with water then dried (MgSO$_4$), filtered and evaporated. The residue was purified by chromatography on silica eluting with a mixture of ethyl acetate and pentane. The desired fractions were concentrated and the sample evaporated to dryness to give the title compound as an oil.

$^1$H NMR (CDCl$_3$) δ 7.8 (d, 1H), 7.5-7.2 (m, 6H), 7.2 (d, 1H), 7.1 (s, 1H), 4.5 (s, 2H), 2.6 (s, 3H)

Preparation 5

N-(4-Chloro-2-methylquinolin-6-yl)benzamide (i) N-(4-Hydroxy-2-methylquinolin-6-yl)benzamide
The sub-title compound was prepared using procedures analogous to those described in Preparation 6(i) below, but using N-(4-aminophenyl)benzamide in place of 4-iodoaniline.
(ii) N-(4-Chloro-2-methylquinolin-6-yl)benzamide
The title compound was prepared using procedures analogous to those described in Preparation 1(iii) above, but using N-(4-hydroxy-2-methylquinolin-6-yl)benzamide (see step (i) above) in place of 6-benzyloxy-4-hydroxy-2-methylquinoline.

$^1$H NMR (D$_6$-DMSO) δ 10.6 (s, 1H), 8.7 (s, 1H), 8.2 (d, 1H), 8.0-7.5 (m, 5H), 5.6 (s, 1H), 2.6 (s, 3H)

Preparation 6

1-(4-Chloro-2-methylquinolin-6-yl)pyrrolidin-2-one (i) 4-Hydroxy-6-iodo-2-methylquinoline
4-Iodoaniline (25 g), ethyl acetoacetate (17.8 g) and polyphosphoric acid (112.5 g) in dioxane (500 mL) were refluxed for 20 hours. The reaction was diluted with water (2 L) and solid sodium carbonate added until the solution reached pH 10.0. The resulting precipitate was isolated by filtration, washed with water and dried under vacuum. Trituration with ether gave the sub-title compound (10 g) as a white solid.

$^1$H NMR (CDCl$_3$) δ 8.3 (s, 1H), 7.8 (d, 1H), 7.3 (d, 1H), 5.9 (s, 1H), 2.3 (s, 3H)

(ii) 4-Chloro-6-iodo-2-methylquinoline
4-Hydroxy-6-iodo-2-methylquinoline (10 g; see step (i) above) in phosphorous oxychloride (70 mL) was heated at 80° C. for 1 hour. The reaction mixture was then cautiously added to ice/water and solid sodium carbonate until the solution reached pH 8.0. The mixture was extracted with ethyl acetate, washed with water, dried (MgSO$_4$), filtered and evaporated. The resulting solid was triturated with diethyl ether to give the sub-title compound (6.4 g) as a white solid.

$^1$H NMR (CDCl$_3$) δ 8.5 (s, 1H), 8.0 (d, 1H), 7.7 (d, 1H), 7.4 (s, 1H), 2.7 (s, 3H)

(iii) 1-(4-Chloro-2-methylquinolin-6-yl)pyrrolidin-2-one
4-Chloro-6-iodo-2-methylquinoline (0.61 g; see step (ii) above), 2-pyrrolidinone (0.24 g), copper (I) iodide (0.038 g), potassium phosphate (0.5 g) and N,N'-dimethylethylenediamine (0.035 g) in dimethylformamide (3 mL) were heated in a microwave at 100° C. for 1 hour. The reaction mixture was diluted with 1 N sodium hydroxide and extracted with ethyl acetate, washed with water, dried (MgSO$_4$), filtered and evaporated. The residue was purified by chromatography on silica eluting with a mixture of dichloromethane, and methanol. The desired fractions were concentrated and the sample evaporated to dryness. Trituration from ether gave the title compound as a white powder (0.2 g).

$^1$H NMR (CDCl$_3$) δ 8.4 (d, 1H), 8.1 (s, 1H), 8.0 (d, 1H), 7.4 (s, 1H), 4.0 (t, 2H), 2.7 (s, 3H), 2.6 (t, 2H), 2.3 (q, 2H)

Preparation 7

2-Methyl-6-nitro-4-(3-phenylpyrrolidin-1-yl)quinoline

4-Chloro-2-methyl-6-nitroquinoline (0.2 g), 3-phenylpyrrolidine (0.14 g) and diisopropyl-ethylamine (0.27 mL) in 2-ethoxyethanol (4 mL) was heated in a microwave to 200° C. for 15 minutes. The reaction mixture was diluted with water and extracted with dichloromethane, washed with water, dried (Na$_2$SO$_4$), filtered and evaporated to give a yellow oil. The residue was purified by chromatography on silica, eluting with a mixture of dichloromethane, ethanol and ammonia (200:8:1). The desired fractions were concentrated to give the title compound as an orange oil.

$^1$H NMR (CDCl$_3$) δ 9.3 (s, 1H), 8.4 (d, 1H), 8.0 (s, 1H), 7.4-7.3 (m, 5H) 6.5 (s, 1H), 4.2-3.5 (m, 5H) 2.7 (s, 3H), 2.6 (m, 1H), 2.4 (m, 1H)

EXAMPLES

Example 1

6-Chloro-2-methyl-4-(3-phenylpyrrolidin-1-yl)quinoline 4,6-Dichloro-2-methylquinoline (0.1 g) and 3-phenylpyrrolidine (0.15 g) in 2-ethoxy-ethanol (1.5 mL) was heated in a microwave at 240° C. for 10 minutes. The mixture was diluted with water and extracted with ethyl acetate, washed with water, dried (MgSO$_4$), filtered and evaporated. The residue was purified by chromatography on silica, eluting with a mixture of methanol and dichloromethane. Evaporation of the desired fractions gave the title compound as a white solid.

$^1$H NMR (CDCl$_3$) δ 8.1 (s, 1H), 7.8 (d, 1H), 7.5 (d, 1H), 7.4 (t, 2H), 7.3 (m, 3H), 6.4 (s, 1H), 4.0 (t, 1H), 3.9 (m, 1H), 3.8 (m, 2H), 3.5 (m, 1H), 2.6 (s, 3H), 2.4 (m, 1H), 2.3 (m, 1H)

LCMS (Method A), Retention time 7.90 minutes; (M+H$^+$) 323

Example 2

6-Benzyloxy-2-methyl-4-(3-phenylpyrrolidin-1-yl)quinoline

The title compound was prepared using procedures analogous to those described in Example 1 above, but using 6-benzyloxy-4-chloro-2-methyl-quinoline (see Preparation 1 above) in place of 4,6-dichloro-2-methylquinoline.

$^1$H NMR (CDCl$_3$) δ 8.0 (m, 1H), 7.5 (s, 1H), 7.4-7.2 (m, 11H), 6.4 (s, 1H), 5.1 (s, 2H), 3.9 (t, 1H), 3.8 (m, 1H), 3.7 (m, 2H), 3.5 (m, 1H), 2.6 (s, 3H), 2.4 (m, 1H), 2.2 (m, 1H)

LCMS (Method 7), retention time 8.9 minutes; M$^+$=396 (M+H$^+$)

Example 3

2-Methyl-4-(3-phenylpyrrolidin-1-yl)-6-(pyridin-3-ylmethoxy)quinoline hydrochloride The free base was prepared using procedures analogous to those described in Example 1 above, but using 4-chloro-2-methyl-6-(pyridin-3-ylmethoxy)quinoline (see Preparation 2 above) in place of 4,6-dichloro-2-methylquinoline. The title compound (corresponding hydrochloride salt) was obtained by treating the free base with hydrochloric acid, followed by evaporation of the solvent.

¹H NMR (D₆-DMSO) δ 14.0 (s, 1H), 8.8 (s, 1H), 8.6 (s, 1H), 8.1 (d, 1H), 8.0 (d, 1H), 7.9 (s, 1H), 7.7 (d, 1H), 7.5 (m, 1H), 7.4 (m, 4H), 7.3 (m, 1H), 6.7 (s, 1H), 5.4 (s, 2H), 4.3 (t, 1H), 4.1 (m, 2H), 3.9 (t, 1H), 3.6 (m, 1H), 2.6 (s, 3H), 2.4 (m, 1H), 2.2 (m, 1H)

LCMS (Method B), Retention time 6.13 minutes (M+H⁺) 396

Example 4

6-(4-Methanesulfonylbenzyloxy)-2-methyl-4-(3-phenylpyrrolidin-1-yl)quinoline

2-Methyl-4-(3-phenylpyrrolidin-1-yl)quinolin-6-ol (0.05 g; see Example 42 below), 1-bromomethyl-4-methanesulfonylbenzene (0.08 g), caesium carbonate (0.1 g) in DMF (2 mL) was heated in a microwave at 120° C. for 15 minutes. The reaction mixture was diluted with water and extracted with dichloromethane, washed with water, dried (MgSO₄), filtered and evaporated to give an oil. The residue was purified by chromatography on silica, eluting with a mixture of dichloromethane, and methanol. Evaporation of the desired fractions gave the title compound as a pale yellow solid.

¹H NMR (CDCl₃) δ 8.0-7.8 (m, 3H), 7.6 (d, 2H), 7.5 (s, 1H), 7.4-7.2 (m, 6H), 6.5 (s, 1H), 5.2 (d, 2H), 3.9-3.6 (m, 4H), 3.5 (m, 1H), 3.0 (s, 3H), 2.6 (s, 3H), 2.4 (m, 1H), 2.2 (m, 1H)

LCMS (Method A); Retention time 7.77 minutes (M+H⁺) 473

Example 5

6-(4-Methoxybenzyloxy)-2-methyl-4-(3-phenylpyrrolidin-1-yl)quinoline

2-Methyl-4-(3-phenylpyrrolidin-1-yl)quinolin-6-ol (0.05 g; see Example 42 below) was stirred with sodium hydride (60% dispersion in mineral oil; 0.035 g) in DMF (2 mL) for 15 minutes, after which 4-methoxybenzyl bromide (0.12 g) was added. After 18 hours, the reaction mixture was diluted with water and extracted with dichloromethane, washed with water, dried (MgSO₄), filtered and evaporated to give a brown oil. The residue was purified by chromatography on silica eluting with a mixture of dichloromethane, and methanol. Evaporation of the desired fractions gave the title compound as a cream solid.

¹H NMR (CDCl₃) δ 8.6 (d, 1H), 7.6 (s, 1H), 7.4-7.2 (m, 8H), 6.8 (d, 2H), 6.2 (s, 1H), 5.1 (d, 2H), 4.1 (t, 1H), 3.9 (m, 2H), 3.8 (t, 1H), 3.7 (s, 3H), 3.6 (m, 1H), 2.8 (s, 3H), 2.5 (m, 1H), 2.3 (m, 1H)

LCMS (Method A); Retention time 8.82 minutes (M+H⁺) 425

Example 6

2-Methyl-6-phenethyloxy-4-(3-phenylpyrrolidin-1-yl)quinoline hydrochloride

The free base was prepared using procedures analogous to those described in Example 5 above, but using (2-bromoethyl)benzene in place of 4-methoxybenzyl bromide. The title compound (corresponding hydrochloride salt) was obtained by treating the free base with HCl(aq) in methanol, followed by evaporation of the solvent.

¹H NMR (D₆-DMSO) δ 13.8 (s, 1H), 7.9 (d, 1H), 7.8 (s, 1H), 7.6 (d, 1H), 7.4-7.2 (m, 10H), 6.7 (s, 1H), 4.4 (t, 2H), 4.4-3.8 (m, 4H), 3.6 (m, 1H), 3.1 (t, 2H), 2.6 (s, 3H), 2.5 (m, 1H), 2.2 (m, 1H)

LCMS (Method A); Retention time 9.1 minutes (M+H⁺) 409

Example 7

2-Methyl-6-(5-methylisoxazol-3-ylmethoxy)-4-(3-phenylpyrrolidin-1-yl)quinoline hydrochloride The free base was prepared using procedures analogous to those described in Example 5 above, but using 3-bromomethyl-5-methylisoxazole in place of 4-methoxy-benzyl bromide. The title compound (corresponding hydrochloride salt) was obtained by treating the free base with HCl(aq) in methanol, followed by evaporation of the solvent.

¹H NMR (D₆-DMSO) δ 14.1 (s, 1H), 8.0 (d, 1H), 7.9 (s, 1H), 7.7 (d, 1H), 7.4 (m, 4H), 7.3 (t, 1H), 6.7 (s, 1H), 6.4 (s, 1H), 5.4 (s, 2H), 4.4-3.9 (m, 4H), 3.6 (m, 1H), 2.6 (s, 3H), 2.5 (m, 1H), 2.4 (s, 3H), 2.2 (m, 1H)

LCMS (Method A); Retention time 8.0 minutes (M+H⁺) 400

Example 8

4-(3-Benzylpyrrolidin-1-yl)-2-methyl-6-phenoxyquinoline hydrochloride

4-Chloro-2-methyl-6-phenoxyquinoline (0.2 g; see Preparation 3 above) and 3-benzyl-pyrrolidine (0.3 g) in 2-ethoxyethanol (4 mL) were heated in a microwave to 200° C. for 20 minutes. The mixture was diluted with 1 N sodium hydroxide and extracted with ethyl acetate, dried (MgSO₄), filtered and evaporated. The residue was purified by preparative HPLC, the relevant fractions combined and evaporated to give a clear oil which was acidified with concentrated hydrochloric acid and then evaporated. Trituration with ether gave the title compound as a white powder.

¹H NMR (D₆-DMSO) δ 14.3 (s, 1H), 8.1 (d, 1H), 7.9 (s, 1H), 7.7 (d, 1H), 7.5 (t, 2H), 7.3 (t, 2H), 7.2 (m, 4H), 7.1 (d, 2H), 6.6 (s, 1H), 3.8 (m, 3H), 3.5 (m, 1H), 2.8-2.5 (m, 6H), 2.0 (m, 1H), 1.7 (m, 1H)

LCMS (Method A); Retention time 9.02 minutes (M+H⁺) 395

In an alternative preparation, 4-chloro-2-methyl-6-phenoxyquinoline (1 eq.) and 3-benzylpyrrolidine (1 eq.) were heated under a nitrogen atmosphere to 150 to 170° C. in the presence of anywhere from 3 to 4 equivalents of 2,4,6-trimethylpyridine. This provided 4-(3-benzylpyrrolidin-1-yl)-2-methyl-6-phenoxyquinoline as the free base.

Example 9

4-[3-(4-Methoxyphenyl)pyrrolidin-1-yl]-2-methyl-6-phenoxyquinoline hydrochloride The title compound was prepared using procedures analogous to either of those described in Example 8 above, but using 3-(4-methoxyphenyl)pyrrolidine in place of 3-benzylpyrrolidine.

¹H NMR (D₆-DMSO) δ 14.1 (s, 1H), 8.1 (d, 1H), 7.9 (s, 1H), 7.7 (d, 1H), 7.4 (t, 2H), 7.3 (d, 2H), 7.2 (t, 1H), 7.1 (d,

2H), 6.9 (d, 2H), 6.7 (s, 1H), 4.2 (m, 1H), 3.9 (m, 2H), 3.8 (m, 4H), 3.5 (m, 1H), 2.6 (s, 3H), 2.4 (m, 1H), 2.1 (m, 1H)

LCMS (Method B); Retention time 8.2 minutes (M+H$^+$) 411

Example 10

4-[3-(4-Chlorophenyl)pyrrolidin-1-yl]-2-methyl-6-phenoxyquinoline hydrochloride

The title compound was prepared using procedures analogous to those described in Example 8 above, but using 3-(4-chlorophenyl)pyrrolidine in place of 3-benzyl-pyrrolidine.

$^1$H NMR (D$_6$-DMSO) δ 14.2 (s, 1H), 8.1 (d, 1H), 7.9 (s, 1H), 7.7 (d, 1H), 7.4 (m, 6H), 7.2 (t, 1H), 7.1 (d, 2H), 6.7 (s, 1H), 4.2 (m, 1H), 3.9 (m, 2H), 3.8 (m, 1H), 3.5 (m, 1H), 2.6 (s, 3H), 2.4 (m, 1H), 2.1 (m, 1H)

LCMS (Method B); Retention time 8.9 minutes (M+H$^+$) 416

Example 11

[1-(2-Methyl-6-phenoxyquinolin-4-yl)pyrrolidin-3-yl]phenylamine 1-(2-Methyl-6-phenoxyquinolin-4-yl)pyrrolidin-3-ylamine (0.107 g; see Example 43 below), bromobenzene (0.058 g), 2-dicyclohexylphosphino-2'-dimethylaminobiphenyl (0.023 g), tris-(dibenzylideneacetone)dipalladium (0.03 g), sodium tert-butoxide (0.044 g) and toluene (3 mL) were heated in a microwave at 150° C. for 20 minutes. The reaction mixture was diluted with water and extracted with ethyl acetate, washed with water, dried (MgSO$_4$), filtered and evaporated to give a brown oil. The residue was purified by chromatography on silica, eluting with a mixture of dichloromethane, and methanol. Evaporation of the desired fractions gave, after trituration with ether, the title compound as a white solid.

$^1$H NMR (CDCl$_3$) δ 7.8 (d, 1H), 7.7 (s, 1H), 7.4-7.2 (m, 3H), 7.2 (t, 2H), 7.1 (t, 1H), 7.0 (d, 2H), 6.8 (t, 1H), 6.6 (d, 2H), 6.4 (s, 1H), 4.2 (m, 1H), 3.9 (q, 1H), 3.8 (m, 1H), 3.6 (m, 1H), 3.4 (m, 1H), 2.6 (s, 3H), 2.3 (m, 1H), 2.1 (m, 1H)

LCMS (Method A); Retention time 8.4 minutes (M+H$^+$) 396

Example 12

N-[2-Methyl-4-(3-phenylpyrrolidin-1-yl)quinolin-6-yl]benzamide hydrochloride

2-Methyl-6-amino-4-(3-phenylpyrrolidin-1-yl)quinoline (0.07 g; see Example 45 below), benzoyl chloride (0.035 g) and diisopropylamine (0.065 g) was stirred in dichloromethane (3 mL). The reaction mixture was diluted with 1 N sodium hydroxide and extracted with ethyl acetate, washed with water, dried (MgSO$_4$), filtered and evaporated to give a brown oil. The residue was purified by chromatography on silica eluting with a mixture of dichloromethane, and methanol. The desired fractions were concentrated, after which hydrochloric acid was added and the sample evaporated to dryness. Trituration from ether gave the title compound as a white solid (0.03 g).

$^1$H NMR (D$_6$-DMSO) δ 13.95 (s, 1H), 10.8 (s, 1H), 9.1 (s, 1H), 8.3 (d, 1H), 8.0 (m, 3H), 7.6 (m, 3H), 7.4 (m, 4H), 7.3 (t, 1H), 6.8 (s, 1H), 3.8-4-4 (m, 4H), 3.7 (m, 1H), 2.6 (s, 3H), 2.1 (m, 1H)

LCMS (Method B); Retention time 7.75 minutes (M+H$^+$) 408

Example 13

N-[2-Methyl-4-(3-phenylpyrrolidin-1-yl)quinolin-6-yl]-2-phenylacetamide

The title compound was prepared using procedures analogous to those described in Example 12 above, but using phenylacetyl chloride in place of benzoyl chloride. Also, the final product was not converted to the hydrochloride salt.

$^1$H NMR (CDCl$_3$) δ 8.95 (s, 1H), 7.8 (d, 1H), 7.2-7.5 (m, 11H), 7.1 (d, 1H), 6.4 (s, 1H), 4.0 (m, 2H), 3.9 (m, 1H), 3.8 (s, 2H), 3.7 (m, 1H), 3.5 (m, 1H), 2.6 (s, 3H), 2.5 (m, 1H), 2.1 (m, 1H)

LCMS (Method A); Retention time 8.32 minutes (M+H$^+$) 422

Example 14

4-Chloro-N-[2-methyl-4-(3-phenylpyrrolidin-1-yl)quinolin-6-yl]benzamide hydrochloride The title compound was prepared using procedures analogous to those described in Example 12 above, but using 4-chlorobenzoyl chloride in place of benzoyl chloride.

$^1$H NMR (D$_6$-DMSO) δ 10.6 (s, 1H), 9.1 (s, 1H), 8.3 (d, 1H), 8.1 (d, 2H), 7.9 (d, 1H), 7.6 (d, 2H), 7.4 (m, 4H), 7.3 (t, 1H), 6.7 (s, 1H), 4.4 (m, 1H), 4.1 (m, 2H), 4.0 (t, 1H), 3.7 (m, 1H), 2.6 (s, 3H), 2.5 (m, 1H), 2.2 (m, 1H)

LCMS (Method B); Retention time 8.50 minutes (M+H$^+$) 442

Example 15

4-Methoxy-N-[2-methyl-4-(3-phenylpyrrolidin-1-yl)quinolin-6-yl]benzamide

The title compound was prepared using procedures analogous to those described in Example 12 above, but using 4-methoxybenzoyl chloride in place of benzoyl chloride. The final product was isolated as the free base.

$^1$H NMR (D$_6$-DMSO) δ 10.6 (s, 1H), 8.8 (s, 1H), 8.0 (m, 3H), 7.7 (d, 1H), 7.4 (m, 4H), 7.3 (t, 1H), 7.1 (d, 2H), 6.5 (s, 1H), 4.0 (m, 2H), 3.9 (s, 3H), 3.7 (m, 2H), 3.5 (m, 1H), 2.3 (s, 3H), 2.4 (m, 1H), 2.2 (m, 1H)

LCMS (Method A); Retention time 8.30 minutes (M+H$^+$) 438

Example 16

2-Methyl-N-[2-methyl-4-(3-phenylpyrrolidin-1-yl)quinolin-6-yl]benzamide

The title compound was prepared using procedures analogous to those described in Example 12 above, but using 2-methylbenzoyl chloride in place of benzoyl chloride. The final product was isolated as the free base.

$^1$H NMR (D$_6$-DMSO) δ 10.5 (s, 1H), 8.0 (d, 1H), 7.7 (d, 1H), 7.5 (d, 1H), 7.4-7.2 (m, 9H), 6.5 (s, 1H), 3.9 (m, 2H), 3.8 (m, 2H), 3.5 (m, 1H), 2.6 (s, 3H), 2.3 (m, 4H), 2.2 (m, 1H)

LCMS (Method B); Retention time 8.14 minutes (M+H$^+$) 422

Example 17

Pyrazine-2-carboxylic acid [2-methyl-4-(3-phenylpyrrolidin-1-yl)quinolin-6-yl]amide hydrochloride 2-Methyl-6-amino-4-(3-phenylpyrrolidin-1-yl)quinoline (0.07 g; see Example 45 below), 2-pyrazinecarboxylic acid (0.037 g), HATU (0.113 g) and diisopropylamine (0.116 g) was stirred in N,N-dimethylformamide (4 mL) for 15 hours. The reaction mixture was diluted with 1 N sodium hydroxide and extracted with ethyl acetate, washed with water, dried (MgSO$_4$), filtered and evaporated to give a brown oil. The residue was purified by chromatography on silica, eluting with a mixture of dichloromethane, and methanol. The desired fractions were concentrated then hydrochloric acid was added and the sample evaporated to dryness. Trituration from ether gave the title compound as a white solid (0.045 g).

$^1$H NMR (D$_6$-DMSO) δ 11.0 (s, 1H), 9.4 (s, 1H), 8.95 (m, 2H), 8.9 (s, 1H), 8.1 (d, 1H), 7.7 (d, 1H), 7.4 (m, 4H), 7.3 (t, 1H), 6.5 (s, 1H), 4.0 (m, 2H), 3.8 (m, 2H), 3.6 (m, 1H), 2.5 (s, 3H), 2.4 (m, 1H), 2.1 (m, 1H)

LCMS (Method A); Retention time 7.39 minutes (M+H$^+$) 410

Example 18

1H-Pyrazole-4-carboxylic acid [2-methyl-4-(3-phenylpyrrolidin-1-yl)quinolin-6-yl]amide hydrochloride The title compound was prepared using procedures analogous to those described in Example 17 above, but using 4-pyrazolecarboxylic acid in place of 2-pyrazinecarboxylic acid.

$^1$H NMR (D$_6$-DMSO) δ 13.8 (s, 1H), 10.3 (s, 1H), 9.2 (s, 1H), 8.3 (s, 1H), 8.2 (d, 1H), 7.9 (d, 1H), 7.4 (m, 4H), 7.3 (t, 1H), 6.6 (s, 1H), 4.4 (m, 1H), 4.2 (m, 2H), 4.0 (m, 2H), 3.6 (m, 1H), 2.6 (s, 3H), 2.5 (m, 1H), 2.2 (m, 1H)

LCMS (Method B); Retention time 6.40 minutes (M+H$^+$) 398

Example 19

Furan-2-carboxylic acid [2-methyl-4-(3-phenylpyrrolidin-1-yl)quinolin-6-yl]amide hydrochloride The title compound was prepared using procedures analogous to those described in Example 17 above, but using 2-furoic acid in place of 2-pyrazinecarboxylic acid.

$^1$H NMR (D$_6$-DMSO) δ 13.7 (s, 1H), 10.6 (s, 1H), 9.2 (s, 1H), 8.5 (s, 1H), 8.2 (d, 1H), 7.9 (d, 1H), 7.8 (s, 1H), 7.4 (m, 4H), 7.3 (t, 1H), 7.1 (s, 1H), 6.7 (s, 1H), 4.4-3.8 (m, 4H), 3.7 (m, 1H), 2.6 (s, 3H), 2.5 (m, 1H), 2.2 (m, 1H)

LCMS (Method A); Retention time 7.64 minutes (M+H$^+$) 398

Example 20

N-[2-Methyl-4-(3-phenylpyrrolidin-1-yl)quinolin-6-yl] nicotinamide hydrochloride The title compound was prepared using procedures analogous to those described in Example 17 above, but using nicotinic acid in place of 2-pyrazinecarboxylic acid.

$^1$H NMR (D$_6$-DMSO) δ 14.0 (s, 1H), 11.1 (s, 1H), 9.3 (s, 1H), 9.2 (s, 1H), 8.8 (d, 1H), 8.5 (d, 1H), 8.3 (d, 1H), 8.0 (d, 1H), 7.7 (m, 1H), 7.4 (m, 4H), 7.3 (t, 1H), 6.8 (s, 1H), 4.4-3.8 (m, 4H), 2.6 (s, 3H), 2.5 (m, 1H), 2.2 (m, 1H)

LCMS (Method B); Retention time 6.74 minutes (M+H$^+$) 409

Example 21

3-Methyl-3H-imidazole-4-carboxylic acid [2-methyl-4-(3-phenylpyrrolidin-1-yl)quinolin-6-yl]amide hydrochloride The title compound was prepared using procedures analogous to those described in Example 17 above, but using 1-methyl-5-imidazolecarboxylic acid in place of 2-pyrazinecarboxylic acid.

$^1$H NMR (D$_6$-DMSO) δ 13.8 (s, 1H), 10.5 (s, 1H), 9.0 (s, 1H), 8.2 (d, 1H), 7.8 (m, 3H), 7.5-7.4 (m, 4H), 7.4 (t, 1H), 6.6 (s, 1H), 4.4-3.8 (m, 4H), 3.8 (s, 3H), 3.6 (m, 1H), 2.6 (s, 3H), 2.5 (m, 1H), 2.2 (m, 1H)

LCMS (Method B); Retention time 5.63 minutes (M+H$^+$) 412

Example 22

5-Methyl-1H-pyrazole-3-carboxylic acid [2-methyl-4-(3-phenylpyrrolidin-1-yl)-quinolin-6-yl]amide hydrochloride The title compound was prepared using procedures analogous to those described in Example 17 above, but using 5-methyl-3-pyrazolecarboxylic acid in place of 2-pyrazinecarboxylic acid.

$^1$H NMR (D$_6$-DMSO) δ 13.8 (s, 1H), 10.6 (s, 1H), 9.1 (s, 1H), 8.4 (d, 1H), 7.9 (d, 1H), 7.5-7.4 (m, 4H), 7.3 (t, 1H), 6.7 (s, 1H), 6.6 (s, 1H), 4.4-3.4 (m, 5H), 2.6 (s, 3H), 2.5 (m, 1H), 2.3 (m, 4H)

LCMS (Method B); Retention time 7.19 minutes (M+H$^+$) 412

Example 23

Pyridazine-4-carboxylic acid [2-methyl-4-(3-phenylpyrrolidin-1-yl)quinolin-6-yl]amide hydrochloride The title compound was prepared using procedures analogous to those described in Example 17 above, but using pyridazine-4-carboxylic acid in place of 2-pyrazinecarboxylic acid.

$^1$H NMR (D$_6$-DMSO) δ 13.8 (s, 1H), 11.4 (s, 1H), 9.7 (s, 1H), 9.5 (s, 1H), 9.2 (s, 1H), 8.4 (d, 1H), 8.2 (s, 1H), 8.0 (d, 1H), 7.5-7.4 (m, 4H), 7.3 (t, 1H), 6.8 (s, 1H), 4.4-3.8 (m, 4H), 3.6 (m, 1H), 2.6 (s, 3H), 2.2 (m, 1H)

LCMS (Method B); Retention time 6.52 minutes (M+H$^+$) 410

Example 24

2-(4-Methoxyphenyl)-N-[2-methyl-4-(3-phenylpyrrolidin-1-yl)quinolin-6-yl]acetamide The title compound was prepared using procedures analogous to those described in Example 17 above, but using 4-methoxyphenylacetic acid in place of 2-pyrazinecarboxylic acid.

¹H NMR (CDCl₃) δ 10.4 (s, 1H), 8.8 (s, 1H), 7.6 (m, 3H), 7.4-7.2 (m, 6H), 6.8 (d, 2H), 6.5 (s, 1H), 3.9 (m, 2H), 3.7 (m, 5H), 3.5 (m, 3H), 2.6 (s, 3H), 2.5 (m, 1H), 2.1 (m, 1H)

LCMS (Method A); Retention time 8.15 minutes (M+H⁺) 452

Example 25

2-(4-Chlorophenyl)-N-[2-methyl-4-(3-phenylpyrrolidin-1-yl)quinolin-6-yl]acetamide The title compound was prepared using procedures analogous to those described in Example 17 above, but using 4-chlorophenylacetic acid in place of 2-pyrazinecarboxylic acid.

¹H NMR (CDCl₃) δ 10.4 (s, 1H), 8.7 (s, 1H), 7.7 (s, 2H), 7.4-7.3 (m, 8H), 7.3 (t, 1H), 6.5 (s, 1H), 3.9 (m, 2H), 3.7 (m, 4H), 3.5 (m, 1H), 2.6 (s, 3H), 2.4 (m, 1H), 2.1 (m, 1H)

LCMS (Method A); Retention time 8.73 minutes (M+H⁺) 456

Example 26

3,5-Dimethyl-isoxazole-4-carboxylic acid [2-methyl-4-(3-phenylpyrrolidin-1-yl)quinolin-6-yl]amide hydrochloride The title compound was prepared using procedures analogous to those described in Example 17 above, but using 3,5-dimethylisoxazole-4-carboxylic acid in place of 2-pyrazinecarboxylic acid.

¹H NMR (D₆-DMSO) δ 13.5 (s, 1H), 10.5 (s, 1H), 9.0 (s, 1H), 8.1 (d, 1H), 7.8 (d, 1H), 7.4-7.3 (m, 4H), 7.3 (t, 1H), 6.7 (s, 1H), 4.3 (m, 1H), 4.1 (m, 2H), 3.9 (m, 1H), 3.6 (m, 1H), 2.6 (s, 3H), 2.5 (s, 3H), 2.4 (s, 3H), 2.3 (m, 1H)

LCMS (Method B); Retention time 7.42 minutes (M+H⁺) 427

Example 27

2-(3-Methyl-isoxazol-5-yl)-N-[2-methyl-4-(3-phenylpyrrolidin-1-yl)quinolin-6-yl]acetamide hydrochloride The title compound was prepared using procedures analogous to those described in Example 17 above, but using 3-methyl-5-isoxazoleacetic acid in place of 2-pyrazinecarboxylic acid.

¹H NMR (D₆-DMSO) δ 13.7 (s, 1H), 10.9 (s, 1H), 9.0 (s, 1H), 8.1 (d, 1H), 7.9 (d, 1H), 7.4-7.3 (m, 4H), 7.3 (t, 1H), 6.7 (s, 1H), 6.3 (s, 1H), 4.3 (m, 1H), 4.1 (m, 2H), 4.0 (s, 2H), 3.9 (m, 1H), 3.6 (m, 1H), 2.6 (s, 3H), 2.2 (m, 4H)

LCMS (Method A); Retention time 7.30 minutes (M+H⁺) 427

Example 28

N-[2-Methyl-4-(3-phenylpyrrolidin-1-yl)quinolin-6-yl]benzenesulfonamide hydrochloride 2-Methyl-6-amino-4-(3-phenylpyrrolidin-1-yl)quinoline (0.07 g; see Example 45 below), benzenesulfonyl chloride (0.041 g) and pyridine (0.04 g) was stirred in dichloromethane (4 mL). The reaction mixture was diluted with 1 N sodium hydroxide and extracted with ethyl acetate, washed with water, dried (MgSO₄), filtered and evaporated to give a brown oil. The residue was purified by chromatography on silica, eluting with a mixture of dichloromethane, and methanol. The desired fractions were concentrated, hydrochloric acid was added, and the sample evaporated to dryness. Trituration from ether gave the title compound as a white solid (0.035 g).

¹H NMR (D₆-DMSO) δ 10.5 (s, 1H), 7.8 (s, 1H), 7.7 (d, 2H), 7.6 (d, 1H), 7.5 (t, 1H), 7.4-7.3 (m, 9H), 6.5 (s, 1H), 3.8-3.4 (m, 5H), 2.4 (s, 3H), 2.4 (m, 1H), 2.1 (m, 1H)

LCMS (Method B); Retention time 7.53 minutes (M+H⁺) 444

Example 29

Benzyl-[2-methyl-4-(3-phenylpyrrolidin-1-yl)quinolin-6-yl]amine

Benzyl-(4-chloro-2-methylquinolin-6-yl)amine (0.041 g; see Preparation 4 above) and 3-phenylpyrrolidine in 2-ethoxyethanol (1 mL) were heated in a microwave to 240° C. for 10 minutes. The reaction mixture was diluted with water and extracted with ethyl acetate, washed with water, dried (MgSO₄), filtered and evaporated. The residue was purified by chromatography on silica, eluting with a mixture of dichloromethane, and methanol. The desired fractions were concentrated and the sample evaporated to dryness. Trituration from ether gave the title compound.

¹H NMR (CDCl₃) δ 7.8 (d, 1H), 7.4-7.2 (m, 11H), 7.1 (d, 1H), 7.0 (s, 1H), 6.4 (s, 1H), 4.4 (s, 2H), 3.7 (t, 1H), 3.6-3.3 (m, 4H), 2.6 (s, 3H), 2.3 (m, 1H), 2.1 (m, 1H)

LCMS (Method A); Retention time 8.9 minutes (M+H⁺) 394

Example 30

(R- or S-)Benzyl-[2-methyl-4-(3-phenylpyrrolidin-1-yl)quinolin-6-yl]amine

Benzyl-[2-methyl-4-(3-phenyl-pyrrolidin-1-yl)quinolin-6-yl]amine (see Example 29 above) was purified by chiral HPLC, eluting with a gradient of acetonitrile/water containing 0.1% formic acid. The title compound of Example 30 eluted from the column first. The solvent was removed from the relevant samples to give the separated enantiomer as a yellow powder.

¹H NMR (CDCl₃) δ 7.8 (d, 1H), 7.4-7.2 (m, 11H), 7.1 (d, 1H), 7.0 (s, 1H), 6.4 (s, 1H), 4.4 (s, 2H), 3.7 (t, 1H), 3.6-3.3 (m, 4H), 2.6 (s, 3H), 2.3 (m, 1H), 2.1 (m, 1H)

LCMS (Method A); Retention time 8.6 minutes (M+H⁺) 394

Example 31

(S- or R-)Benzyl-[2-methyl-4-(3-phenylpyrrolidin-1-yl)quinolin-6-yl]amine

The title compound of Example 31 was prepared according to the procedure outlined in Example 30 above, and was the second compound eluted from the column. The solvent was removed from the relevant samples to give the separated enantiomer as a yellow powder.

¹H NMR (CDCl₃) δ 7.9 (d, 1H), 7.4-7.2 (m, 11H) 7.1 (d, 1H), 7.0 (s, 1H), 6.4 (s, 1H), 4.4 (s, 2H), 3.7 (t, 1H), 3.6-3.3 (m, 4H), 2.6 (s, 3H), 2.3 (m, 1H), 2.1 (m, 1H)

LCMS (Method A); Retention time 8.8 minutes (M+H⁺) 394

Example 32

(4-Methoxybenzyl)-[2-methyl-4-(3-phenylpyrrolidin-1-yl)quinolin-6-yl]amine

2-Methyl-6-amino-4-(3-phenylpyrrolidin-1-yl)quinoline (0.08 g; see Example 45 below), 4-methoxybenzaldehyde (0.071 g), sodium triacetoxyborohydride (0.165 g) and acetic acid (0.05 mL) in 1,2-dichloroethane (5 mL) was refluxed for 4 hours. The reaction mixture was diluted with 1 N sodium hydroxide and extracted with ethyl acetate, washed with water, dried (MgSO$_4$), filtered and evaporated. The residue was purified by chromatography on silica, eluting with a mixture of dichloromethane, and methanol. The desired fractions were concentrated and the sample evaporated to dryness. Trituration from ether gave the title compound as a white powder (0.01 g).

$^1$H NMR (CDCl$_3$) δ 7.8 (d, 1H), 7.4-7.2 (m, 7H), 7.1 (d, 2H), 6.8 (d, 2H), 6.4 (s, 1H), 4.4 (s, 2H), 3.8 (m, 1H), 3.7 (s, 3H), 3.7-3.4 (m, 4H), 2.6 (s, 3H), 2.3 (m, 1H), 2.1 (m, 1H)

LCMS (Method B); Retention time 8.42 minutes (M+H$^+$) 424

Example 33

4-{[2-Methyl-4-(3-phenylpyrrolidin-1-yl)quinolin-6-ylamino]methyl}benzonitrile

The title compound was prepared using procedures analogous to those described in Example 32 above, but using 4-cyanobenzaldehyde in place of 2-pyrazinecarboxylic acid.

$^1$H NMR (D$_6$-DMSO) δ 7.6-7.5 (m, 4H), 7.4 (t, 2H), 7.3-7.2 (m, 3H), 7.1 (d, 1H), 6.7 (s, 1H), 6.6 (t, 1H), 6.4 (s, 1H), 4.4 (m, 2H), 3.6-3.2 (5H) 2.4 (s, 3H), 2.2 (m, 1H), 2.1 (m, 1H)

LCMS (Method A); Retention time 8.23 minutes (M+H$^+$) 419

Example 34

1-[2-Methyl-4-(3-phenylpyrrolidin-1-yl)quinolin-6-yl]pyrrolidin-2-one

A mixture of 1-(4-chloro-2-methylquinolin-6-yl)pyrrolidin-2-one (0.2 g; see Preparation 6 above) and 3-phenylpyrrolidine (0.282 g) in 2-ethoxyethanol was heated in a microwave at 250° C. for 20 minutes. The reaction mixture was diluted with 1 N sodium hydroxide and extracted with ethyl acetate, washed with water, dried (MgSO$_4$), filtered and evaporated. Trituration from ether gave the title compound as a white powder (0.08 g).

$^1$H NMR (D$_6$-DMSO) δ 8.6 (s, 1H), 7.8 (d, 1H), 7.7 (d, 1H), 7.4-7.3 (m, 4H), 7.2 (t, 1H), 6.5 (s, 1H), 3.9 (m, 4H), 3.7 (t, 2H), 3.5 (m, 1H), 2.5 (m, 1H), 2.4 (m, 1H), 2.1 (m, 1H)

LCMS (Method B); Retention time 6.7 minutes (M+H$^+$) 372

Example 35

N-[2-Methyl-4-(3-phenylpyrrolidin-1-yl)quinolin-6-yl]-3-phenyl propionamide

The title compound was prepared using procedures analogous to those described in Example 12 above, but using 3-phenylpropionyl chloride in place of benzoyl chloride. The final product was isolated as the free base.

$^1$H NMR (D$_6$-DMSO) δ 10.4 (s, 1H), 10.1 (s, 1H), 8.7 (s, 1H), 7.7 (s, 2H), 7.4-7.1 (m, 9H), 6.5 (s, 1H), 3.9 (m, 1H), 3.7 (m, 2H), 3.5 (m, 1H), 2.8 (t, 2H), 2.6 (t, 2H), 2.5 (s(3H), 2.4 (m, 1H), 2.2 (m, 1H)

LCMS (Method B); Retention time 8.18 minutes (M+H$^+$) 436

Example 36

5-Methyl-isoxazole-3-carboxylic acid [2-methyl-4-(3-phenylpyrrolidin-1-yl)-quinolin-6-yl]amide The title compound was prepared using procedures analogous to those described in Example 17 above, but using 5-methyl-3-isoxazolecarboxylic acid in place of 2-pyrazinecarboxylic acid. The final product was isolated as the free base.

$^1$H NMR (D$_6$-DMSO) δ 10.7 (s, 1H), 8.8 (s, 1H), 8.0 (d, 1H), 7.7 (d, 1H), 7.5-7.3 (m, 4H), 7.3 (m, 1H), 6.7 (s, 1H), 6.5 (s, 1H), 3.9 (m, 2H), 3.7 (t, 2H), 3.5 (m, 1H), 2.5 (m, 6H), 2.4 (m, 1H), 2.2 (m, 1H)

LCMS (Method A); Retention time 7.90 minutes (M+H$^+$) 413

Example 37

Pyridine-2-carboxylic acid [2-methyl-4-(3-phenylpyrrolidin-1-yl)quinolin-6-yl]amide hydrochloride The title compound was prepared using procedures analogous to those described in Example 17 above, but using pyridine-2-carboxylic acid in place of 2-pyrazinecarboxylic acid.

$^1$H NMR (D$_6$-DMSO) δ 14.0 (s, 1H), 11.3 (s, 1H), 9.2 (s, 1H), 8.9 (d, 1H), 8.5 (d, 1H), 8.2 (d, 1H), 8.1 (t, 1H), 8.0 (d, 1H), 7.7 (m, 1H), 7.5-7.4 (m, 4H), 7.3 (t, 1H), 6.7 (s, 1H), 4.4-4.0 (m, 4H), 3.6 (m, 1H), 2.6 (s, 3H), 2.2 (m, 1H)

LCMS (Method A); Retention time 7.95 minutes (M+H$^+$) 409

Example 38

N-[4-(3-Benzylpyrrolidin-1-yl)-2-methylquinolin-6-yl]benzamide

The title compound was prepared using procedures analogous to those described in Example 1 above, but using N-(4-chloro-2-methylquinolin-6-yl)benzamide (see Preparation 5 above) in place of 4,6-dichloro-2-methylquinoline and 3-benzylpyrrolidine in place of 3-phenylpyrrolidine.

$^1$H NMR (D$_6$-DMSO) δ 10.5 (s, 1H), 8.9 (s, 1H), 8.0 (m, 2H), 7.9 (d, 1H), 7.7 (d, 1H), 7.5-7.4 (m, 3H), 7.3 (m, 4H), 7.2 (m, 1H), 6.4 (s, 1H), 3.8 (m, 3H), 3.5 (t, 1H), 2.8 (m, 2H), 2.5 (m, 1H), 2.4 (s, 3H), 2.1 (m, 1H), 1.7 (m, 1H)

LCMS (Method B); Retention time 8.19 minutes (M+H$^+$) 422

In an alternative preparation, the title compound was obtained by heating N-(4-chloro-2-methylquinolin-6-yl)benzamide (1 eq.) and 3-benzylpyrrolidine (1 eq.) together under a nitrogen atmosphere to 150 to 170° C. in the presence of anywhere from 3 to 4 equivalents of 2,4,6-trimethylpyridine.

Example 39

2-Methyl-6-phenoxy-4-(3-phenylpyrrolidin-1-yl) quinoline hydrochloride

The title compound was prepared using procedures analogous to those described in Example 8 above, but using 3-phenylpyrrolidine in place of 3-benzylpyrrolidine.

$^1$H NMR (D$_6$-DMSO) δ 14.0 (s, 1H), 8.0 (d, 1H), 7.9 (s, 1H), 7.7 (d, 1H), 7.4-7.2 (m, 7H), 7.2 (t, 1H), 7.1 (d, 2H), 6.7 (s, 1H), 4.2 (m, 1H), 3.9 (m, 2H), 3.8 (m, 1H), 3.5 (m, 1H), 2.7 (s, 3H), 2.5 (m, 1H), 2.1 (m, 1H)

LCMS (Method B); Retention time 8.7 minutes (M+H$^+$) 381

Example 40

The free base form of the title compound of Example 8 was subjected to analytical chiral HPLC under the following conditions.
Column: 250×4.6 mm Chiralpak™ IB 5 μm
Mobile phase: heptane/isopropanol/diethylamine 70/30/0.1
Flow rate: 1 mL/min
Detection: UV 250 nm
Temperature: 25° C.

The analytical HPLC revealed two major products:
(a) retention time 7.59 minutes (49.63% of total area under curve); and
(b) retention time 12.94 minutes (50.30% of total area under curve).

Using this information, 100 mg of the free base form of the title compound of Example 8 was subjected to preparative HPLC under the following conditions.
Column: 250×20 mm Chiralpak™ IB 5 μm
Mobile phase: heptane/isopropanol/diethylamine 70/30/0.1
Flow rate: 20 mL/min
Detection: UV 250 nm
Temperature: 25° C.

The first— and second-eluting products (enantiomers) were collected separately, providing:
(a) 40.5 mg of the first eluting enantiomer (retention time 7.6 minutes); and
(b) 41.4 mg of the second eluting enantiomer (retention time 12.9 minutes).

(a) 4-((R- or S-)-3-benzylpyrrolidin-1-yl)-2-methyl-6-phenoxyquinoline

The first-eluting enantiomer.
Analysis of this product by analytical HPLC (under the conditions for analytical chiral HPLC indicated above) showed the following:
Product: retention time 7.51 minutes (99.96% total area under curve);
Minor impurity: retention time 6.48 minutes (0.03% total area under curve).
Calculated enantiomeric excess >99.5%;
$^1$H NMR: identical spectrum to the racemate (see Example 8 above).

(b) 4-((S- or R-)-3-benzylpyrrolidin-1-yl)-2-methyl-6-phenoxyquinoline

The first-eluting enantiomer.
Analysis of this product by analytical HPLC (under the conditions for analytical chiral HPLC indicated above) showed the following:
Product: retention time 12.86 minutes (99.95% total area under curve);
Minor impurity: retention time 7.18 minutes (0.05% total area under curve).
Calculated enantiomeric excess >99.5%;
$^1$H NMR: identical spectrum to the racemate (see Example 8 above).

Example 41

The free base form of the title compound of Example 9 was subjected to analytical chiral HPLC under the following conditions.
Column: 250×4.6 mm Chiralpak™ IA 5 μm
Mobile phase: heptane/isopropanol/ethylenediamine 70/30/0.1
Flow rate: 1 mL/min
Detection: UV 280 nm
Temperature: 25° C.

The analytical HPLC revealed two products:
(a) retention time 8.63 minutes (50.58% of total area under curve); and
(b) retention time 10.42 minutes (49.42% of total area under curve).

Using this information, 100 mg of the free base form of the title compound of Example 9 was subjected to preparative HPLC under the following conditions.
Column: 250×30 mm Chiralpak™ AD-H 5 μm
Mobile phase: heptane/isopropanol/diethylamine 70/30/0.1
Flow rate: 42.5 mL/min
Detection: UV 250 nm
Temperature: 25° C.

The first- and second-eluting products (enantiomers) were collected separately, providing:
(a) 50.1 mg of the first eluting enantiomer (retention time 8.6 minutes); and
(b) 50.3 mg of the second eluting enantiomer (retention time 10.4 minutes).

(a) 4-[(R- or S-)-3-(4-methoxyphenyl)pyrrolidin-1-yl]-2-methyl-6-phenoxyquinoline The first-eluting enantiomer.
Analysis of this product by analytical HPLC (under the conditions for analytical chiral HPLC indicated above) showed the following:
Product: retention time 8.50 minutes (100.00% total area under curve).
Calculated enantiomeric excess >99.5%;
$^1$H NMR: identical spectrum to the racemate (see Example 9 above).

(b) 4-[(S- or R-)-3-(4-methoxyphenyl)pyrrolidin-1-yl]-2-methyl-6-phenoxyquinoline The second-eluting enantiomer.
Analysis of this product by analytical HPLC (under the conditions for analytical chiral HPLC indicated above) showed the following:
Product: retention time 10.38 minutes (100.00% total area under curve).
Calculated enantiomeric excess >99.5%;
$^1$H NMR: identical spectrum to the racemate (see Example 9 above).

Example 42

The free base form of the title compound of Example 22 was subjected to analytical chiral HPLC under the following conditions.

Column: 250×4.6 mm Chiralpak™ IA 5 μm
Mobile phase: heptane/ethanol/ethylenediamine 70/30/0.1
Flow rate: 1 mL/min
Detection: UV 280 nm
Temperature: 25° C.

The analytical HPLC revealed two products:
(a) retention time 10.47 minutes (50.20% of total area under curve); and
(b) retention time 14.15 minutes (49.80% of total area under curve).

Using this information, 100 mg of the free base form of the title compound of Example 22 was subjected to preparative HPLC under the following conditions.
Column: 250×20 mm Chiralpak™ IA 5 μm
Mobile phase: heptane/ethanol/diethylamine 80/20/0.1
Flow rate: 20 mL/min
Detection: UV 290 nm
Temperature: 25° C.

The first- and second-eluting products (enantiomers) were collected separately, providing:
(a) 52.1 mg of the first eluting enantiomer (retention time 10.5 minutes); and
(b) 44.0 mg of the second eluting enantiomer (retention time 14.1 minutes).

(a) 5-methyl-1H-pyrazole-3-carboxylic acid [2-methyl-4-((R- or S-)-3-phenyl-pyrrolidin-1-O-quinolin-6-yl]amide The first-eluting enantiomer.
Analysis of this product by analytical HPLC (under the conditions for analytical chiral HPLC indicated above) showed the following:
Product: retention time 10.44 minutes (99.95% total area under curve);
Minor impurity: retention time 14.30 minutes (0.05% total area under curve).
Calculated enantiomeric excess >99.5%;
$^1$H NMR: identical spectrum to the racemate (see Example 22 above).

(b) 5-methyl-1H-pyrazole-3-carboxylic acid [2-methyl-4-((S- or R-)-3-phenyl-pyrrolidin-1-yl)-quinolin-6-yl]amide The second-eluting enantiomer.
Analysis of this product by analytical HPLC (under the conditions for analytical chiral HPLC indicated above) showed the following:
Product: retention time 14.04 minutes (99.95% total area under curve);
Minor impurity: retention time 10.62 minutes (0.05% total area under curve).
Calculated enantiomeric excess >99.5%;
$^1$H NMR: identical spectrum to the racemate (see Example 22 above).

Example 43

The title compound of Example 38 was subjected to analytical chiral HPLC under the following conditions.
Column: 250×4.6 mm Chiralpak™ IC 5 μm
Mobile phase: heptane/isopropanol/ethylenediamine 75/25/0.1
Flow rate: 1 mL/min
Detection: UV 280 nm
Temperature: 25° C.

The analytical HPLC revealed two products:
(a) retention time 14.28 minutes (49.52% of total area under curve); and
(b) retention time 17.56 minutes (50.48% of total area under curve).

Using this information, 100 mg of the title compound of Example 38 was subjected to preparative HPLC under the following conditions.
Column: 250×50 mm Chiralpak™ IC 5 μm
Mobile phase: heptane/isopropanol/diethylamine 75/25/0.1
Flow rate: 100 mL/min
Detection: UV 250 nm
Temperature: 25° C.

The first- and second-eluting products (enantiomers) were collected separately, providing:
(a) 44.8 mg of the first eluting enantiomer (retention time 14.3 minutes); and
(b) 43.4 mg of the second eluting enantiomer (retention time 17.6 minutes).

(a) N-[4-((R- or S-)-3-benzylpyrrolidin-1-yl)-2-methylquinolin-6-yl]benzamide

The first-eluting enantiomer.
Analysis of this product by analytical HPLC (under the conditions for analytical chiral HPLC indicated above) showed the following:
Product: retention time 14.16 minutes (100.00% total area under curve).
Calculated enantiomeric excess >99.5%;
$^1$H NMR: identical spectrum to the racemate (see Example 38 above).

(b) N-[4-((S- or R-)-3-benzylpyrrolidin-1-yl)-2-methylquinolin-6-yl]benzamide

The second-eluting enantiomer.
Analysis of this product by analytical HPLC (under the conditions for analytical chiral HPLC indicated above) showed the following:
Product: retention time 17.52 minutes (99.85% total area under curve);
Minor impurity: retention time 14.40 minutes (0.15% total area under curve).
Calculated enantiomeric excess >99.5%;
$^1$H NMR: identical spectrum to the racemate (see Example 38 above).

Example 44

2-Methyl-4-(3-phenylpyrrolidin-1-yl)quinolin-6-ol

6-Benzyloxy-2-methyl-4-(3-phenylpyrrolidin-1-yl) quinoline (0.3 g; see Example 2 above) and palladium on carbon (10%; 0.2 g) in ethanol (8 mL) was stirred under hydrogen for 3 hours. The mixture was filtered and then concentrated to give the title compound as a yellow oil, which was used without further purification.

Example 45

1-(2-Methyl-6-phenoxyquinolin-4-yl)pyrrolidin-3-ylamine (i) [1-(2-Methyl-6-phenoxyquinolin-4-yl)-pyrrolidin-3-yl] carbamic acid tert-butyl ester The sub-title compound was prepared using procedures analogous to those described in Example 8 above, but using 3-(tert-butyloxycarbonylamino)pyrrolidine in place of 3-benzylpyrrolidine. The product was used directly in the next step.

(ii) 1-(2-Methyl-6-phenoxyquinolin-4-yl)pyrrolidin-3-ylamine

The product from step (i) above was treated with trifluoroacetic acid in dichloromethane (1:1) to give, after evaporation, the title compound as an orange oil, which was used without further purification.

Example 46

2-Methyl-6-amino-4-(3-phenylpyrrolidin-1-yl)quinoline

2-Methyl-6-nitro-4-(3-phenylpyrrolidin-1-yl)quinoline (0.29 g; see Preparation 7 above) and palladium on carbon (10%, 0.2 g) in ethanol (10 mL) and dichloromethane (4 mL) was stirred under a hydrogen atmosphere for 3 hours. The reaction mixture was filtered and concentrated to give the title compound as a thick yellow oil, which was used without further purification.

Example 47

Compounds of Examples 1 to 46 above were found to possess activity in biological tests described above. Biological activity that was determined included a log kill, at 20, or 5 μg/mL of test compound, of above 0.5 (e.g. above 3) against log phase, stationary phase and/or persister bacteria of the types *Staph. aureus*, methicillin-resistant *Staph. aureus* (MRSA), Coagulase negative *staphylococcus* (CNS), *Streptococcus pneumoniae*, *Streptococcus pyogenes*, *Streptococcus agalactiae*, *Enterococcus*, *E. coli*, *Candida albicans*, *Propionibacterium acnes* and *Mycobacterium tuberculosis*.

Indeed, the following compounds had the activity indicated.

(a) The compound of Example 6, when tested against *Staph. aureus* stationary phase bacteria at 5 μg/mL of test compound, displayed a log kill of 6.16.
(b) The compound of Example 8, when tested at 10 μg/mL of test compound, displayed:
  (i) a log kill of 6.34 against methicillin-resistant *Staph. aureus* stationary phase bacteria;
  (ii) a log kill of 0.97 against *Streptococcus agalactiae* stationary phase bacteria;
  (iii) a log kill of 3.70 against stationary phase *Candida albicans*; and
  (iv) a log kill of 5.76 and 2.26 against, respectively, stationary phase and persister *Mycobacterium tuberculosis*.
(c) The compound of Example 9, when tested against *Streptococcus pyogenes* stationary phase bacteria at 20 μg/mL of test compound, displayed a log kill of 6.42.
(d) The compound of Example 22, when tested at 5 μg/mL of test compound, displayed:
  (i) a log kill of 5.99 against Coagulase negative *staphylococcus* stationary phase bacteria; and
  (ii) a log kill of 3.22 against *Enterococcus* stationary phase bacteria.
(e) The compound of Example 39, when tested at 10 μg/mL of test compound, displayed:
  (i) a log kill of 7.32 against *Streptococcus pneumoniae* stationary phase bacteria;
  (ii) a log kill of 6.80 against *E. coli* K12 stationary phase bacteria; and
  (iii) a log kill of 6.34 against *Propionibacterium acnes* stationary phase bacteria.
(f) Both enantiomers of Example 40, as well as both enantiomers of Example 43, when tested at 20 μg/mL of test compound, displayed:
  (i) a log kill of 6.26 against *Staph. aureus* stationary phase bacteria;
  (ii) a log kill of 6.22 against MRSA stationary phase bacteria; and
  (iii) a log kill of 6.27 against stationary phase *Candida albicans*.
(g) Both enantiomers of Example 41, as well as both enantiomers of Example 42, when tested at 5 μg/mL of test compound, displayed:
  (i) a log kill of 6.26 against *Staph. aureus* stationary phase bacteria; and
  (ii) a log kill of 6.22 against MRSA stationary phase bacteria.

Abbreviations
br=broad (in relation to NMR)
d=doublet (in relation to NMR)
DCC=dicyclohexyl carbodiimide
DCE=1,2-dichloroethane
DCM=dichloromethane
DEAD=diethylazodicarboxylate
DIPEA=diisopropylethylamine
DMAP=4-(N,N-dimethyl amino) pyridine
DMF=dimethylformamide
DMSO=dimethylsulfoxide
EDC=1-(3-dimethylaminopropyl)-3-ethylcarbodiimide hydrochloride
EDTA=ethylenediaminetetraacetic acid
HATU=O-(azabenzotriazol-1-yl)-N,N,N',N'-tetramethyluronium hexafluorophosphate
HBTU=[N,N,N',N'-tetramethyl-O-(benzotriazol-1-yl)uronium hexafluorophosphate]
HEC=hydroxyethylcellulose
HOAt=1-hydroxy-7-azabenzotriazole
HOBt=1-hydroxybenzotriazole
HOSu=N-hydroxysuccinimide
HPLC=high performance liquid chromatography
LC=liquid chromatography
m=multiplet (in relation to NMR)
MBC=minimum bactericidal concentration
Me=methyl
min.=minute(s)
MIC=minimum inhibitory concentration
MS=mass spectroscopy
NMR=nuclear magnetic resonance
PyBOP=(benzotriazol-1-yloxy)tripyrrolidinophosphonium hexafluorophosphate
q=quartet (in relation to NMR)
s=singlet (in relation to NMR)
t=triplet (in relation to NMR)
TBTU=[N,N,N',N'-tetramethyl-O-(benzotriazol-1-yl)uronium tetrafluoroborate]
TEA=triethylamine Prefixes n-, s-, i-, t- and tert- have their usual meanings: normal, secondary, iso, and tertiary.

The invention claimed is:
1. A compound, for use in the treatment of a bacterial, protozoal, or fungal infection in a mammal infected with such an infection, wherein the compound is:
2-methyl-6-phenethyloxy-4-(3-phenylpyrrolidin-1-yl) quinoline;
4-(3-benzylpyrrolidin-1-yl)-2-methyl-6-phenoxyquinoline;

4-[3-(4-methoxyphenyl)pyrrolidin-1-yl]-2-methyl-6-phenoxyquinoline hydrochloride;
5-methyl-1H-pyrazole-3-carboxylic acid[2-methyl-4-(3-phenylpyrrolidin-1-yl)-quinolin-6-yl]amide;
N-[4-(3-benzylpyrrolidin-1-yl)-2-methylquinolin-6-yl] benzamide,
or a pharmaceutically-acceptable salt.

2. A compound, for use in the treatment of a bacterial, protozoal, or fungal infection in a mammal infected with such an infection, wherein the compound is:
(1) 6-chloro-2-methyl-4-(3-phenylpyrrolidin-1-yl)quinoline;
(2) 6-benzyloxy-2-methyl-4-(3-phenylpyrrolidin-1-yl) quinoline;
(3) 2-methyl-4-(3-phenylpyrrolidin-1-yl)-6-(pyridin-3-yl methoxy)quinoline;
(4) 6-(4-methanesulfonylbenzyloxy)-2-methyl-4-(3-phenylpyrrolidin-1-yl)quinoline;
(5) 6-(4-methoxybenzyloxy)-2-methyl-4-(3-phenylpyrrolidin-1-yl)quinoline;
(6) 2-methyl-6-phenethyloxy-4-(3-phenylpyrrolidin-1-yl) quinoline;
(7) 2-methyl-6-(5-methylisoxazol-3-ylmethoxy)-4-(3-phenylpyrrolidin-1-yl)quinoline;
(8) 4-(3-benzylpyrrolidin-1-yl)-2-methyl-6-phenoxyquinoline;
(9) 4-[3-(4-methoxyphenyl)pyrrolidin-1-yl]-2-methyl-6-phenoxyquinoline;
(10) 4-[3-(4-chlorophenyl)pyrrolidin-1-yl]-2-methyl-6-phenoxyquinoline;
(11) [1-(2-methyl-6-phenoxyquinolin-4-yl)-pyrrolidin-3-yl]phenylamine;
(12) N-[2-methyl-4-(3-phenylpyrrolidin-1-yl)quinolin-6-yl]benzamide;
(13) N-[2-methyl-4-(3-phenylpyrrolidin-1-yl)-quinolin-6-yl]-2-phenylacetamide;
(14) 4-chloro-N-[2-methyl-4-(3-phenylpyrrolidin-1-yl) quinolin-6-yl]benzamide;
(15) 4-methoxy-N-[2-methyl-4-(3-phenylpyrrolidin-1-yl) quinolin-6-yl]benzamide;
(16) 2-methyl-N-[2-methyl-4-(3-phenylpyrrolidin-1-yl) quinolin-6-yl]benzamide;
(17) pyrazine-2-carboxylic acid[2-methyl-4-(3-phenylpyrrolidin-1-yl)quinolin-6-yl]amide;
(18) 1 H-pyrazole-4-carboxylic acid[2-methyl-4-(3-phenylpyrrolidin-1-yl)quinolin-6-yl]amide;
(19) furan-2-carboxylic acid[2-methyl-4-(3-phenylpyrrolidin-1-yl)quinolin-6-yl]amide;
(20) N-[2-methyl-4-(3-phenylpyrrolidin-1-yl)quinolin-6-yl]nicotinamide;
(21) 3-methyl-3H-imidazole-4-carboxylic acid[2-methyl-4-(3-phenylpyrrolidin-1-yl)quinolin-6-yl]amide;
(22) 5-methyl-1 H-pyrazole-3-carboxylic acid[2-methyl-4-(3-phenylpyrrolidin-1-yl)-quinolin-6-yl]amide;
(23) pyridazine-4-carboxylic acid[2-methyl-4-(3-phenylpyrrolidin-1-yl)-quinolin-6-yl]amide;
(24) 2-(4-methoxyphenyl)-N-[2-methyl-4-(3-phenylpyrrolidin-1-yl)quinolin-6-yl]acetamide;
(25) 2-(4-chlorophenyl)-N-[2-methyl-4-(3-phenylpyrrolidin-1-yl)quinolin-6-yl]acetamide;
(26) 3,5-dimethyl-isoxazole-4-carboxylic acid[2-methyl-4-(3-phenylpyrrolidin-1-yl)quinolin-6-yl]amide;
(27) 2-(3-methyl-isoxazo 1-5-yl)-N-[2-methyl-4-(3-phenyl-pyrrolid i n-1-yl)-quinolin-6-yl]acetamide;
(28) N-[2-methyl-4-(3-phenylpyrrolidin-1-yl)quinolin-6-yl]benzenesulfonamide;
(29) benzyl-[2-methyl-4-(3-phenylpyrrolidin-1-yl)quinolin-6-yl]amine;
(30) (R- or S-) benzyl[2-methyl-4-(3-phenylpyrrolidin-1-yl)quinolin-6-yl]amine;
(31) (S- or R-) benzyl[2-methyl-4-(3-phenylpyrrolidin-1-yl)quinolin-6-yl]amine;
(32) (4-methoxybenzyl)-[2-methyl-4-(3-phenylpyrrolidin-1-yl)quinolin-6-yl]amine;
(33) 4-{[2-methyl-4-(3-phenylpyrrolidin-1-yl)quinolin-6-ylamino]methyl}benzonitrile;
(34) 1-[2-methyl-4-(3-phenylpyrrolidin-1-yl)quinolin-6-yl]pyrrolidin-2-one;
(35) N-[2-methyl-4-(3-phenylpyrrolidin-1-yl)quinolin-6-yl]-3-phenyl propionamide;
(36) 5-methyl-isoxazole-3-carboxylic acid[2-methyl-4-(3-phenylpyrrolidin-1-yl) -quinolin-6-yl]amide;
(37) pyridine-2-carboxylic acid[2-methyl-4-(3-phenylpyrrolidin-1-yl)quinolin-6-yl]amide;
(38) N-[4-(3-benzylpyrrolidin-1-yl)-2-methylquinolin-6-yl]benzamide; or
(39) 2-methyl-6-phenoxy-4-(3-phenylpyrrolidin-1-yl) quinoline;
or pharmaceutically-acceptable salts or solvates thereof.

3. A formulation for use in the treatment of a bacterial, protozoal, or fungal infection in a mammal infected with such an infection comprising a compound of formula I,
wherein the compound of formula I is represented by the structure

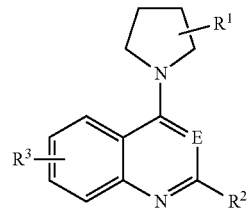

wherein
E represents CH;
$R^1$ represents —X—$R^{4a}$ a substituent at the 3-position of the pyrrolidinyl ring;
X represents
(a) a direct bond, or
(b) N(H);
$R^{4a}$ represents
(a) $C_{1-12}$ alkyl, which alkyl group is substituted by one or more substituents selected from phenyl (which latter group is optionally substituted by one or more substituents selected from halo, CN, $C_{1-3}$ alkyl or $OR^{10a}$), or
(b) phenyl (which latter group is optionally substituted by one or more substituents selected from halo, CN, $C_{1-3}$ alkyl or $OR^{10a}$);
$R^2$ represents $C_{1-2}$ alkyl;
$R^3$ represents a substituent on the fused benzene ring at the 6-position of the quinoline ring system, selected from
(a) halo,
(b) $OR^{8a}$,
(c) $N(H)S(O)_2R^{8f}$,
(d) $N(H)(R^{8h})$,
(e) $N(H)C(O)R^{8i}$,
(f) $C(O)N(H)R^{8i}$, or
(g) $Het^6$;
$R^{8a}$, $R^{8f}$, $R^{8h}$, and $R^{8i}$ independently represent, at each occurrence, (a) $C_{1-4}$ alkyl optionally substituted by phenyl (which latter group is optionally substituted by one or more substituents selected from halo, CN, $C_{1-2}$ alkyl, methoxy, ethoxy and $S(O)_2$—$C_{1-2}$ alkyl)) or $Het^7$), (b) phenyl (which latter group is optionally substituted by one or more substituents selected from halo, CN, $C_{1-2}$ alkyl, methoxy, ethoxy and $S(O)_2$—$C_{1-2}$ alkyl)) or (c) $Het^9$;

$R^{10a}$ represents $C_{1-4}$ alkyl, $Het^6$ represents a 5- or 6-membered, fully saturated heterocyclic group containing one nitrogen atom (which atom forms the point of attachment of the $Het^6$ group to the rest of the molecule) and, optionally, one further heteroatom selected from oxygen and nitrogen, which heterocyclic group may be substituted by one or more substituents selected from halo, methyl, and =O;

$Het^7$ and $Het^9$ independently represent 5- or 6-membered aromatic heterocyclic groups containing one to three heteroatoms selected from oxygen, nitrogen and/or sulfur, which heterocyclic groups may be substituted by one or more substituents selected from halo, CN and $C_{1-2}$ alkyl, and a conventional sterilising agent, or a salt and/or solvate thereof.

4. A combination product for use in the treatment of a bacterial, protozoal, or fungal infection in a mammal infected with such an infection comprising (A) a compound of formula I, wherein the compound of formula I is represented by the structure

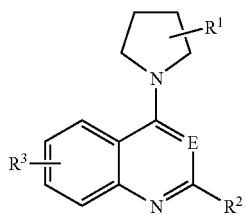

wherein

E represents CH;

$R^1$ represents -X-$R^{4a}$ a substituent at the 3-position of the pyrrolidinyl ring;

X represents (a) a direct bond, or (b) N(H);

$R^{4a}$ represents (a) $C_{1-12}$ alkyl, which alkyl group is substituted by one or more substituents selected from phenyl (which latter group is optionally substituted by one or more substituents selected from halo, CN, $C_{1-3}$ alkyl or $OR^{10a}$), or (b) phenyl (which latter group is optionally substituted by one or more substituents selected from halo, CN, $C_{1-3}$ alkyl or $OR^{10a}$);

$R^2$ represents $C_{1-2}$ alkyl;

$R^3$ represents a substituent on the fused benzene ring at the 6-position of the quinoline ring system, selected from (a) halo, (b) $OR^{8a}$, (c) $N(H)S(O)2R^{8f}$, (d) $N(H)(R^{8h})$, (e) $N(H)C(O)R^{8i}$, (f) $C(O)N(H)R^{8i}$, or (g) $Het^6$;

$R^{8a}$, $R^{8f}$, $R^{8h}$, and $R^{8i}$ independently represent, at each occurrence, (a) $C_{1-4}$ alkyl optionally substituted by phenyl (which latter group is optionally substituted by one or more substituents selected from halo, CN, $C_{1-2}$ alkyl, methoxy, ethoxy and $S(O)_2$—$C_{1-2}$ alkyl)) or $Het^7$), (b) phenyl (which latter group is optionally substituted by one or more substituents selected from halo, CN, $C_{1-2}$ alkyl, methoxy, ethoxy and $S(O)_2$—$C_{1-2}$ alkyl)) or (c) $Het^9$;

$R^{10a}$ represents $C_{1-4}$ alkyl, $Het^6$ represents a 5- or 6-membered, fully saturated heterocyclic group containing one nitrogen atom (which atom forms the point of attachment of the $Het^6$ group to the rest of the molecule) and, optionally, one further heteroatom selected from oxygen and nitrogen, which heterocyclic group may be substituted by one or more substituents selected from halo, methyl, and =O;

$Het^7$ and $Het^9$ independently represent 5- or 6-membered aromatic heterocyclic groups containing one to three heteroatoms selected from oxygen, nitrogen and/or sulfur, which heterocyclic groups may be substituted by one or more substituents selected from halo, CN and $C_{1-2}$ alkyl and (B) a conventional antimicrobial agent, wherein each of components (A) and (B) is formulated in admixture with a pharmaceutically-acceptable adjuvant, diluent or carrier.

5. A combination product according to claim 4, wherein the conventional antimicrobial agent is a penicillin (optionally combined with a β-lactamase inhibitor), a cephalosporin, a monobactam, a carbapenem (optionally combined with a renal enzyme inhibitor), a 1-oxa-β-lactam, a tetracycline, an aminoglycoside, a macrolide, a ketolide, a lincosamine, clindamycin, clindamycin 2-phosphate, a phenicol, a steroid, a glycopeptide, an oxazolidinone, a streptogramin (or a combination of streptogramins), a polymyxin, a lysostaphin, an actinomycin, actinonin, 7-aminoactinomycin D, antimycin A, antipain, bacitracin, cyclosporin A, echinomycin, a gramicidin, myxothiazol, nisin, paracelsin, valinomycin, viomycin, a lipopeptide, a sulfonamide (optionally in combination with trimethoprim), trimethoprim, isoniazid, rifampicin, rifabutin, pyrazinamide, ethambutol, streptomycin, dapsone, clofazimine, a nitroimidazole, a nitrofuran, a quinolone, azaserine, bestatin, D-cycloserine, 1,10-phenanthroline, 6-diazo-5-oxo-L-norleucine, L-alanyl-L-1-aminoethyl-phosphonic acid, an aureolic acid, a benzochinoide a coumarin-glycoside, an epipolythiodixopiperazine, cerulenin a glucosamine, staurosporine, a macrolactam, a taxoid, a statin, a polyphenolic acid, lasalocid A, lonomycin A, monensin, nigericin, salinomycin, fusaric acid, blasticidine S, nikkomycin, nourseothricin, puromycin, adenine 9-β-D-arabinofuranoside, 5-azacytidine, cordycepin, formycin A, tubercidin, tunicamycin, methenamine (hexamine), piericidin A, stigmatellin, actidione, anisomycin, apramycin, coumermycin A1, L(+)-lactic acid, a cytochalasin, emetine, ionomycin, an azole antifungal, a polyene antifungal, griseofulvin, caspofungin or flucytosine (which latter two agents are optionally employed in combination) or an allylamine antifungal.

6. A combination product according to claim 4, which product is a pharmaceutical formulation including a compound of formula I and a conventional antimicrobial agent, together in admixture with a pharmaceutically-acceptable adjuvant, diluent or carrier.

7. A combination product according to claim 4, which product is a kit of parts comprising components:

(I) a pharmaceutical formulation including a compound of formula I in admixture with a pharmaceutically-acceptable adjuvant, diluent or carrier; and (II) a pharmaceutical formulation including a conventional antimicrobial agent, in admixture with a pharmaceutically-acceptable adjuvant, diluent or carrier, which components (I) and (II) are each provided in a form that is suitable for administration in conjunction with the other.

8. A combination product as defined in claim 4 for use in the treatment of a microbial or fungal infection in a mammal infected with such an infection.

9. A combination product as defined in claim 4 for use in the treatment of a bacterial or fungal infection in a mammal infected with such an infection.

10. A combination product as claimed in claim 4, wherein the product or formulation is for topical administration.

11. A formulation comprising a compound selected from the group consisting of:
(1) 6-chloro-2-methyl-4-(3-phenylpyrrolidin-1-yl)quinoline;
(2) 6-benzyloxy-2-methyl-4-(3-phenylpyrrolidin-1-yl)quinoline;
(3) 2-methyl-4-(3-phenylpyrrolidin-1-yl)-6-(pyridin-3-ylmethoxy)quinoline;
(4) 6-(4-methanesulfonylbenzyloxy)-2-methyl-4-(3-phenylpyrrolidin-1-yl)quinoline;
(5) 6-(4-methoxybenzyloxy)-2-methyl-4-(3-phenylpyrrolidin-1-yl)quinoline;
(6) 2-methyl-6-phenethyloxy-4-(3-phenylpyrrolidin-1-yl)quinoline;
(7) 2-methyl-6-(5-methylisoxazol-3-ylmethoxy)-4-(3-phenylpyrrolidin-1-yl)quinoline;
(8) 4-(3-benzylpyrrolidin-1-yl)-2-methyl-6-phenoxyquinoline;
(9) 4-[3-(4-methoxyphenyl)pyrrolidin-1-yl]-2-methyl-6-phenoxyquinoline;
(10) 4-[3-(4-chlorophenyl)pyrrolidin-1-yl]-2-methyl-6-phenoxyquinoline;
(11) [1-(2-methyl-6-phenoxyquinolin-4-yl)-pyrrolidin-3-yl]phenylamine;
(12) N-[2-methyl-4-(3-phenylpyrrolidin-1-yl)quinolin-6-yl]benzamide;
(13) N-[2-methyl-4-(3-phenylpyrrolidin-1-yl)-quinolin-6-yl]-2-phenylacetamide;
(14) 4-chloro-N-[2-methyl-4-(3-phenylpyrrolidin-1-yl)quinolin-6-yl]benzamide;
(15) 4-methoxy-N-[2-methyl-4-(3-phenylpyrrolidin-1-yl)quinolin-6-yl]benzamide;
(16) 2-methyl-N-[2-methyl-4-(3-phenylpyrrolidin-1-yl)quinolin-6-yl]benzamide;
(17) pyrazine-2-carboxylic acid[2-methyl-4-(3-phenylpyrrolidin-1-yl)quinolin-6-yl]amide;
(18) 1 H-pyrazole-4-carboxylic acid[2-methyl-4-(3-phenylpyrrolidin-1-yl)quinolin-6-yl]amide;
(19) furan-2-carboxylic acid[2-methyl-4-(3-phenylpyrrolidin-1-yl)quinolin-6-yl]amide;
(20) N-[2-methyl-4-(3-phenylpyrrolidin-1-yl)quinolin-6-yl]nicotinamide;
(21) 3-methyl-3H-imidazole-4-carboxylic acid[2-methyl-4-(3-phenylpyrrolidin-1-yl)quinolin-6-yl]amide;
(22) 5-methyl-1 H-pyrazole-3-carboxylic acid[2-methyl-4-(3-phenylpyrrolidin-1-yl) -quinolin-6-yl]amide;
(23) pyridazine-4-carboxylic acid[2-methyl-4-(3-phenylpyrrolidin-1-yl)-quinolin-6-yl]amide;
(24) 2-(4-methoxyphenyl)-N-[2-methyl-4-(3-phenylpyrrolidin-1-yl)quinolin-6-yl]acetamide;
(25) 2-(4-chlorophenyl)-N-[2-methyl-4-(3-phenylpyrrolidin-1-yl)quinolin-6-yl]acetamide;
(26) 3,5-dimethyl-isoxazole-4-carboxylic acid [2-methyl-4-(3-phenylpyrrolidin-1-yl)quinolin-6-yl]amide;
(27) 2-(3-methyl-isoxazo 1-5-yl)-N-[2-methyl-4-(3-phenyl-pyrrolid i n-1-yl)-quinolin-6-yl]acetamide;
(28) N-[2-methyl-4-(3-phenylpyrrolidin-1-yl)quinolin-6-yl]benzenesulfonamide;
(29) benzyl-[2-methyl-4-(3-phenylpyrrolidin-1-yl)quinolin-6-yl]amine;
(30) (R- or S-) benzyl [2-methyl-4-(3-phenylpyrrolidin-1-yl)quinolin-6-yl]amine;
(31) (S- or R-) benzyl [2-methyl-4-(3-phenylpyrrolidin-1-yl)quinolin-6-yl]amine;
(32) (4-methoxybenzyl)-[2-methyl-4-(3-phenylpyrrolidin-1-yl)quinolin-6-yl]amine;
(33) 4-{[2-methyl-4-(3-phenylpyrrolidin-1-yl)quinolin-6-ylamino]methyl}benzonitrile;
(34) 1-[2-methyl-4-(3-phenylpyrrolidin-1-yl)quinolin-6-yl]pyrrolidin-2-one;
(35) N-[2-methyl-4-(3-phenylpyrrolidin-1-yl)quinolin-6-yl]-3-phenyl propionamide;
(36) 5-methyl-isoxazole-3-carboxylic acid[2-methyl-4-(3-phenylpyrrolidin-1-yl) -quinolin-6-yl]amide;
(37) pyridine-2-carboxylic acid[2-methyl-4-(3-phenylpyrrolidin-1-yl)quinolin-6-yl]amide;
(38) N-[4-(3-benzylpyrrolidin-1-yl)-2-methylquinolin-6-yl]benzamide;
(39) 2-methyl-6-phenoxy-4-(3-phenylpyrrolidin-1-yl)quinoline; and
(40) 4-[3-(4-methoxyphenyl)pyrrolidin-1-yl]-2-methyl-6-phenoxyquinoline hydrochloride;

or pharmaceutically-acceptable salts or solvates thereof and a conventional sterilising agent, or a salt and/or solvate thereof.

12. A combination product comprising
(A) a compound selected from the group consisting of:
(1) 6-chloro-2-methyl-4-(3-phenylpyrrolidin-1-yl)quinoline;
(2) 6-benzyloxy-2-methyl-4-(3-phenylpyrrolidin-1-yl)quinoline;
(3) 2-methyl-4-(3-phenylpyrrolidin-1-yl)-6-(pyridin-3-ylmethoxy)quinoline;
(4) 6-(4-methanesulfonylbenzyloxy)-2-methyl-4-(3-phenylpyrrolidin-1-yl)quinoline;
(5) 6-(4-methoxybenzyloxy)-2-methyl-4-(3-phenylpyrrolidin-1-yl)quinoline;
(6) 2-methyl-6-phenethyloxy-4-(3-phenylpyrrolidin-1-yl)quinoline;
(7) 2-methyl-6-(5-methylisoxazol-3-ylmethoxy)-4-(3-phenylpyrrolidin-1-yl)quinoline;
(8) 4-(3-benzylpyrrolidin-1-yl)-2-methyl-6-phenoxyquinoline;
(9) 4-[3-(4-methoxyphenyl)pyrrolidin-1-yl]-2-methyl-6-phenoxyquinoline;
(10) 4-[3-(4-chlorophenyl)pyrrolidin-1-yl]-2-methyl-6-phenoxyquinoline;
(11) [1-(2-methyl-6-phenoxyquinolin-4-yl)-pyrrolidin-3-yl]phenylamine;
(12) N-[2-methyl-4-(3-phenylpyrrolidin-1-yl)quinolin-6-yl]benzamide;
(13) N-[2-methyl-4-(3-phenylpyrrolidin-1-yl)-quinolin-6-yl]-2-phenylacetamide;
(14) 4-chloro-N-[2-methyl-4-(3-phenylpyrrolidin-1-yl)quinolin-6-yl]benzamide;
(15) 4-methoxy-N-[2-methyl-4-(3-phenylpyrrolidin-1-yl)quinolin-6-yl]benzamide;

(16) 2-methyl-N-[2-methyl-4-(3-phenylpyrrolidin-1-yl)quinolin-6-yl]benzamide;
(17) pyrazine-2-carboxylic acid[2-methyl-4-(3-phenylpyrrolidin-1-yl)quinolin-6-yl]amide;
(18) 1 H-pyrazole-4-carboxylic acid[2-methyl-4-(3-phenylpyrrolidin-1-yl)quinolin-6-yl]amide;
(19) furan-2-carboxylic acid[2-methyl-4-(3-phenylpyrrolidin-1-yl)quinolin-6-yl]amide;
(20) N-[2-methyl-4-(3-phenylpyrrolidin-1-yl)quinolin-6-yl]nicotinamide;
(21) 3-methyl-3H-imidazole-4-carboxylic acid[2-methyl-4-(3-phenylpyrrolidin-1-yl)quinolin-6-yl]amide;
(22) 5-methyl-1 H-pyrazole-3-carboxylic acid[2-methyl-4-(3-phenylpyrrolidin-1-yl)-quinolin-6-yl]amide;
(23) pyridazine-4-carboxylic acid[2-methyl-4-(3-phenylpyrrolidin-1-yl)-quinolin-6-yl]amide;
(24) 2-(4-methoxyphenyl)-N-[2-methyl-4-(3-phenylpyrrolidin-1-yl)quinolin-6-yl]acetamide;
(25) 2-(4-chlorophenyl)-N-[2-methyl-4-(3-phenylpyrrolidin-1-yl)quinolin-6-yl]acetamide;
(26) 3,5-dimethyl-isoxazole-4-carboxylic acid[2-methyl-4-(3-phenylpyrrolidin-1-yl)quinolin-6-yl]amide;
(27) 2-(3-methyl-isoxazo 1-5-yl)-N-[2-methyl-4-(3-phenyl-pyrrolid i n-1-yl)-quinolin-6-yl]acetamide;
(28) N-[2-methyl-4-(3-phenylpyrrolidin-1-yl)quinolin-6-yl]benzenesulfonamide;
(29) benzyl-[2-methyl-4-(3-phenylpyrrolidin-1-yl)quinolin-6-yl]amine;
(30) (R- or S-) benzyl[2-methyl-4-(3-phenylpyrrolidin-1-yl)quinolin-6-yl]amine;
(31) (S- or R-) benzyl[2-methyl-4-(3-phenylpyrrolidin-1-yl)quinolin-6-yl]amine;
(32) (4-methoxybenzyl)-[2-methyl-4-(3-phenylpyrrolidin-1-yl)quinolin-6-yl]amine;
(33) 4-{[2-methyl-4-(3-phenylpyrrolidin-1-yl)quinolin-6-ylamino]methyl}benzonitrile;
(34) 1-[2-methyl-4-(3-phenylpyrrolidin-1-yl)quinolin-6-yl]pyrrolidin-2-one;
(35) N-[2-methyl-4-(3-phenylpyrrolidin-1-yl)quinolin-6-yl]-3-phenyl propionamide;
(36) 5-methyl-isoxazole-3-carboxylic acid[2-methyl-4-(3-phenylpyrrolidin-1-yl)-quinolin-6-yl]amide;
(37) pyridine-2-carboxylic acid[2-methyl-4-(3-phenylpyrrolidin-1-yl)quinolin-6-yl]amide;
(38) N-[4-(3-benzylpyrrolidin-1-yl)-2-methylquinolin-6-yl]benzamide;
(39) 2-methyl-6-phenoxy-4-(3-phenylpyrrolidin-1-yl)quinoline; and
(40) 4-[3-(4-methoxyphenyl)pyrrolidin-1-yl]-2-methyl-6-phenoxyquinoline hydrochloride;
or pharmaceutically-acceptable salts or solvates thereof, and
(B) a conventional antimicrobial agent,
wherein each of components (A) and (B) is formulated in admixture with a pharmaceutically-acceptable adjuvant, diluent or carrier.

13. A combination product according to claim 12, wherein the conventional antimicrobial agent is a penicillin (optionally combined with a β-lactamase inhibitor), a cephalosporin, a monobactam, a carbapenem (optionally combined with a renal enzyme inhibitor), a 1-oxa-β-lactam, a tetracycline, an aminoglycoside, a macrolide, a ketolide, a lincosamine, clindamycin, clindamycin 2-phosphate, a phenicol, a steroid, a glycopeptide, an oxazolidinone, a streptogramin (or a combination of streptogramins), a polymyxin, a lysostaphin, an actinomycin, actinonin, 7-aminoactinomycin D, antimycin A, antipain, bacitracin, cyclosporin A, echinomycin, a gramicidin, myxothiazol, nisin, paracelsin, valinomycin, viomycin, a lipopeptide, a sulfonamide (optionally in combination with trimethoprim), trimethoprim, isoniazid, rifampicin, rifabutin, pyrazinamide, ethambutol, streptomycin, dapsone, clofazimine, a nitroimidazole, a nitrofuran, a quinolone, azaserine, bestatin, D-cycloserine, 1,10-phenanthroline, 6-diazo-5-oxo-L-norleucine, L-alanyl-L-1-aminoethyl-phosphonic acid, an aureolic acid, a benzochinoide a coumarin-glycoside, an epipolythiodixopiperazine, cerulenin a glucosamine, staurosporine, a macrolactam, a taxoid, a statin, a polyphenolic acid, lasalocid A, lonomycin A, monensin, nigericin, salinomycin, fusaric acid, blasticidine S, nikkomycin, nourseothricin, puromycin, adenine 9-β-D-arabinofuranoside, 5-azacytidine, cordycepin, formycin A, tubercidin, tunicamycin, methenamine (hexamine), piericidin A, stigmatellin, actidione, anisomycin, apramycin, coumermycin A1, L(+)-lactic acid, a cytochalasin, emetine, ionomycin, an azole antifungal, a polyene antifungal, griseofulvin, caspofungin or flucytosine (which latter two agents are optionally employed in combination) or an allylamine antifungal.

14. A combination product according to claim 12, which product is a pharmaceutical formulation including a compound of Component (A) and a conventional antimicrobial agent, together in admixture with a pharmaceutically-acceptable adjuvant, diluent or carrier.

15. A combination product according to claim 12, which product is a kit of parts comprising components:
(I) a pharmaceutical formulation including a compound of Component (A) in admixture with a pharmaceutically-acceptable adjuvant, diluent or carrier; and
(II) a pharmaceutical formulation including a conventional antimicrobial agent, in admixture with a pharmaceutically-acceptable adjuvant, diluent or carrier,
which components (I) and (II) are each provided in a form that is suitable for administration in conjunction with the other.

16. A combination product as defined in claim 12 for use in the treatment of a microbial or fungal infection in a mammal infected with such an infection.

17. A combination product as defined in claim 12 for use in the treatment of a bacterial or fungal infection in a mammal infected with such an infection.

18. A combination product as claimed in claim 12, wherein the product or formulation is for topical administration.

* * * * *